United States Patent
Kim

(10) Patent No.: US 11,015,179 B2
(45) Date of Patent: *May 25, 2021

(54) PEPTIDE HAVING ANTI-VIRAL EFFECT AND COMPOSITION CONTAINING SAME

(71) Applicants: GemVax & KAEL CO., LTD., Daejeon (KR); Sang Jae Kim, Seoul (KR)

(72) Inventor: Sang Jae Kim, Seoul (KR)

(73) Assignee: GemVax & KAEL Co., Ltd., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/739,483

(22) PCT Filed: Jul. 4, 2016

(86) PCT No.: PCT/KR2016/007192
§ 371 (c)(1),
(2) Date: Dec. 22, 2017

(87) PCT Pub. No.: WO2017/003267
PCT Pub. Date: Jan. 5, 2017

(65) Prior Publication Data
US 2019/0032032 A1 Jan. 31, 2019

(30) Foreign Application Priority Data

Jul. 2, 2015 (KR) .................. 10-2015-0094840
Aug. 17, 2015 (KR) .................. 10-2015-0115671

(51) Int. Cl.
| | | |
|---|---|---|
| C12N 9/12 | (2006.01) | |
| A61P 31/20 | (2006.01) | |
| A61P 31/14 | (2006.01) | |
| A61P 31/18 | (2006.01) | |
| A61K 38/10 | (2006.01) | |
| A61K 38/16 | (2006.01) | |
| A61K 38/17 | (2006.01) | |
| A61P 31/12 | (2006.01) | |
| A23L 33/18 | (2016.01) | |
| A61K 9/00 | (2006.01) | |
| A61K 49/00 | (2006.01) | |
| A61K 38/00 | (2006.01) | |

(52) U.S. Cl.
CPC ............ *C12N 9/1276* (2013.01); *A23L 33/18* (2016.08); *A61K 9/0056* (2013.01); *A61K 38/10* (2013.01); *A61K 38/16* (2013.01); *A61K 38/17* (2013.01); *A61K 49/0043* (2013.01); *A61K 49/0056* (2013.01); *A61P 31/12* (2018.01); *A61P 31/14* (2018.01); *A61P 31/18* (2018.01); *A61P 31/20* (2018.01); *C12Y 207/07049* (2013.01); *A23V 2002/00* (2013.01); *A61K 38/00* (2013.01)

(58) Field of Classification Search
None
See application file for complete search history.

(56) References Cited

U.S. PATENT DOCUMENTS

| | | |
|---|---|---|
| 6,967,211 B2 | 11/2005 | Inoue |
| 7,030,211 B1 | 4/2006 | Gaudernack et al. |
| 7,786,084 B2 | 8/2010 | Benner et al. |
| 7,794,723 B2 | 9/2010 | Gaudernack et al. |
| 8,828,403 B2 | 9/2014 | Filaci et al. |
| 8,933,197 B2 | 1/2015 | Bogin et al. |
| 9,023,987 B2 | 5/2015 | Chung et al. |
| 9,540,419 B2 | 1/2017 | Kim et al. |
| 9,572,858 B2 | 2/2017 | Kim et al. |
| 9,907,837 B2 | 3/2018 | Kim et al. |
| 9,907,838 B2 | 3/2018 | Kim et al. |
| 9,937,240 B2 | 4/2018 | Kim et al. |
| 10,039,811 B2 | 8/2018 | Kim et al. |
| 2002/0042401 A1 | 4/2002 | Ferguson et al. |
| 2003/0027769 A1 | 2/2003 | Scialdone et al. |
| 2003/0143228 A1 | 7/2003 | Chen et al. |
| 2006/0106196 A1 | 5/2006 | Gaudernack et al. |
| 2007/0190561 A1 | 8/2007 | Morin et al. |
| 2008/0025986 A1 | 1/2008 | Ozes et al. |
| 2009/0136917 A1 | 5/2009 | Szalay et al. |
| 2009/0186802 A1 | 7/2009 | Alluis et al. |
| 2009/0215852 A1 | 8/2009 | Bascomb et al. |

(Continued)

FOREIGN PATENT DOCUMENTS

| | | |
|---|---|---|
| CN | 1313773 A | 9/2001 |
| CN | 102875657 * | 8/2013 |

(Continued)

OTHER PUBLICATIONS

WO2013169067 (Kim) translation of claims (Year: 2013).*
Gait and Karn, Tibtech vol. 13, pp. 430-438, 1995 (Year: 1995).*
Naider and Anglister Current Opinion in Structural Biology vol. 19, pp. 473-482, 2009 (Year: 2009).*
Gali et al. Antimicrob Agents Chemother vol. 54, pp. 5105-5114, 2010 (Year: 2010).*
Root and Steger, Current Pharmaceutical Design vol. 10, pp. 1805-1825, 2004 (Year: 2004).*
Albini, A., et al., "Cancer Prevention by Targeting Angiogenesis," Nature reviews Clinical oncology 9(9):498-509, Nature Pub Group (2012).

(Continued)

*Primary Examiner* — Shanon A. Foley
*Assistant Examiner* — Myron G Hill
(74) *Attorney, Agent, or Firm* — Clark & Elbing LLP

(57) ABSTRACT

The present specification relates to an anti-viral composition and, more particularly, to a composition that both is anti-viral and prevents and treats diseases associated with viruses, containing a peptide derived from a telomerase, thereby being effective in treating and preventing diseases associated with viruses and pathological symptoms caused by viruses. The peptide exhibits an effect of treating diseases associated with viruses by inhibiting the RNA replication of viruses, thereby being capable of providing a method that both is antiviral and prevents and treats diseases associated with viruses.

6 Claims, 48 Drawing Sheets

Specification includes a Sequence Listing.

(56) References Cited

U.S. PATENT DOCUMENTS

| | | |
|---|---|---|
| 2010/0003229 A1 | 1/2010 | Santos |
| 2011/0135692 A1 | 6/2011 | Filaci et al. |
| 2011/0150873 A1 | 6/2011 | Grainger |
| 2011/0183925 A1 | 7/2011 | Sato et al. |
| 2012/0065124 A1 | 3/2012 | Morishita et al. |
| 2012/0107271 A1 | 5/2012 | Kwong |
| 2012/0208755 A1 | 8/2012 | Leung |
| 2012/0277290 A1 | 11/2012 | Collard et al. |
| 2013/0129760 A1 | 5/2013 | Gaudernack et al. |
| 2013/0230591 A1 | 9/2013 | Fellous et al. |
| 2015/0099692 A1 | 4/2015 | Kim et al. |
| 2015/0099693 A1* | 4/2015 | Kim ............... C07K 14/4703 514/1.9 |
| 2015/0175978 A1 | 6/2015 | Kim et al. |
| 2015/0307859 A1 | 10/2015 | Kim |
| 2015/0343095 A1 | 12/2015 | Kim et al. |
| 2016/0002613 A1 | 1/2016 | Kim et al. |
| 2016/0008438 A1 | 1/2016 | Kim et al. |
| 2016/0120966 A1 | 5/2016 | Kim |
| 2016/0137695 A1 | 5/2016 | Kim |
| 2016/0151512 A1 | 6/2016 | Kim |
| 2016/0250279 A1 | 9/2016 | Kim et al. |
| 2016/0296604 A1 | 10/2016 | Kim et al. |
| 2016/0375091 A1 | 12/2016 | Kim |
| 2017/0028035 A1 | 2/2017 | Kim et al. |
| 2017/0058001 A1 | 3/2017 | Kim |
| 2017/0081376 A1 | 3/2017 | Kim et al. |
| 2017/0128557 A1 | 5/2017 | Kim et al. |
| 2017/0143806 A1 | 5/2017 | Kim et al. |
| 2017/0275603 A1 | 9/2017 | Kim et al. |
| 2017/0360870 A1 | 12/2017 | Kim |
| 2018/0036384 A1 | 2/2018 | Kim |
| 2018/0207241 A1 | 7/2018 | Kim |
| 2018/0318383 A1 | 11/2018 | Kim et al. |
| 2019/0030137 A1 | 1/2019 | Kim et al. |
| 2019/0142894 A1 | 5/2019 | Kim et al. |

FOREIGN PATENT DOCUMENTS

| | | |
|---|---|---|
| EP | 1020190 A3 | 10/2000 |
| EP | 1093381 B2 | 7/2009 |
| EP | 1817337 B1 | 1/2011 |
| JP | 2002520293 A | 7/2002 |
| JP | 2002522373 A | 7/2002 |
| JP | 2010252810 A | 11/2010 |
| JP | 2011515498 A | 5/2011 |
| JP | 2012500279 A | 1/2012 |
| JP | 2012526524 A | 11/2012 |
| JP | 5577472 B2 | 8/2014 |
| KR | 19930001915 A | 2/1993 |
| KR | 20010012613 A | 2/2001 |
| KR | 20010020601 A | 3/2001 |
| KR | 20040015087 A | 2/2004 |
| KR | 20040045400 A | 6/2004 |
| KR | 20040107492 A | 12/2004 |
| KR | 20050020987 A | 3/2005 |
| KR | 20050040517 A | 5/2005 |
| KR | 20060065588 A | 6/2006 |
| KR | 20060109903 A | 10/2006 |
| KR | 20070083218 A | 8/2007 |
| KR | 20080084818 A | 9/2008 |
| KR | 20090033878 A | 4/2009 |
| KR | 20090103957 A | 10/2009 |
| KR | 20100058541 A | 6/2010 |
| KR | 20100085527 A | 7/2010 |
| KR | 20110057049 A | 5/2011 |
| KR | 20110060940 A | 6/2011 |
| KR | 20110062943 A | 6/2011 |
| KR | 20110130943 A | 12/2011 |
| KR | 20120018188 A | 2/2012 |
| KR | 20120026408 A | 3/2012 |
| KR | 20120035150 A | 4/2012 |
| KR | 20120087885 A | 8/2012 |
| KR | 20120121196 A | 11/2012 |
| KR | 20120130896 A | 12/2012 |
| KR | 20120133661 A | 12/2012 |
| KR | 20130004949 A | 1/2013 |
| KR | 20130041896 A | 4/2013 |
| KR | 20140037698 A | 3/2014 |
| KR | 20140104288 A | 8/2014 |
| WO | WO-0002581 A1 | 1/2000 |
| WO | WO-0007565 A2 | 2/2000 |
| WO | WO-2009120914 A1 | 1/2009 |
| WO | WO-2009025871 A1 | 2/2009 |
| WO | WO-2010003520 A2 | 1/2010 |
| WO | WO-2010012850 A1 | 2/2010 |
| WO | WO-2010022125 A1 | 2/2010 |
| WO | WO-2010128807 A2 | 11/2010 |
| WO | WO-2011101173 A1 | 8/2011 |
| WO | WO-2011150494 A1 | 12/2011 |
| WO | WO 2013169067 * | 5/2013 |
| WO | WO-2013100500 A1 | 7/2013 |
| WO | WO-2013118899 A1 | 8/2013 |
| WO | WO-2013135266 A1 | 9/2013 |
| WO | WO-2013167298 A1 | 11/2013 |
| WO | WO-2013167574 A1 | 11/2013 |
| WO | WO-2013169060 A1 | 11/2013 |
| WO | WO-2013169067 A1 | 11/2013 |
| WO | WO-2013169077 A1 | 11/2013 |
| WO | WO-2014010971 A1 | 1/2014 |
| WO | WO-2014012683 A1 | 1/2014 |
| WO | WO-2014046478 A1 | 3/2014 |
| WO | WO-2014046481 A1 | 3/2014 |
| WO | WO-2014046490 A1 | 3/2014 |
| WO | WO-2014046983 A1 | 3/2014 |
| WO | WO-2014130909 A1 | 8/2014 |
| WO | WO-2014171792 A1 | 10/2014 |
| WO | WO-2014196841 A1 | 12/2014 |
| WO | WO-2014204281 A1 | 12/2014 |
| WO | WO-2015060673 A1 | 4/2015 |
| WO | WO-2015076621 A1 | 5/2015 |
| WO | WO-2015093854 A1 | 6/2015 |
| WO | WO-2015156649 A1 | 10/2015 |
| WO | WO-2015167067 A1 | 11/2015 |
| WO | WO-2016105086 A1 | 6/2016 |
| WO | WO-2016137162 A1 | 9/2016 |
| WO | WO-2017078440 A1 | 5/2017 |

OTHER PUBLICATIONS

Altschul, S.F., et al., "Basic Local Alignment Search Tool," Journal of Molecular Biology 215(3):403-410, Elsevier, England (Oct. 1990).

Auerbach, R., et al., "Angiogenesis Assays: Problems and Pitfalls," Cancer Metastasis Reviews 19(1-2):167-172, Kluwer Academic, Netherlands (2000).

Beer, T.M., et al., "Phase II Study of Weekly Docetaxel in Symptomatic Androgen-independent Prostate Cancer," Annals of Oncology 12(9):1273-1279, Oxford University Press, England (2001).

Berendsen, H.J., "A Glimpse of the Holy Grail?," Science 282(5389):642-643, American Association for the Advancement of Science, United States (1998).

Bernhardt, S.L., et al., "Telomerase Peptide Vaccination of Patients with Non-Resectable Pancreatic Cancer: A Dose Escalating Phase I/II Study," British Journal of Cancer 95(11):1474-1482, Nature Publishing Group on behalf of Cancer Research, England (2006).

Bohonowych, J.E., et al., "Comparative Analysis of Novel and Conventional HSP90 Inhibitors on HIF Activity and Angiogenic Potential in Clear Cell Renal Cell Carcinoma: Implications for Clinical Evaluation," BMC Cancer 11:520, BioMed Central, England (2011).

Bonaldi, T., et al., "Monocytic Cells Hyperacetylate Chromatin Protein HMGB1 to Redirect it Towards Secretion," The EMBO Journal 22(20):5551-5560, Wiley Blackwell, England (2003).

Brandenburg, K., et al., "Peptide-based Treatment of Sepsis," Applied Microbiology and Biotechnology 90(3):799-808, Springer International, Germany (2011).

Bruns, A.F., et al., "A Heat-shock Protein Axis Regulates VEGFR2 Proteolysis, Blood Vessel Development and Repair," PloS One 7(11):e48539, Public Library of Science, United States (2012).

(56) References Cited

OTHER PUBLICATIONS

Brunsvig, P.F., et al., "Telomerase Peptide Vaccination in NSCLC: A Phase II Trial in Stage III Patients Vaccinated after Chemoradiotherapy and an 8-year Update on a Phase I/II Trial," Clinical Cancer Research 17(21):6847-6857, The Association, United States (2011).
Calderwood, S.K., et al., "Heat Shock Proteins in Cancer: Chaperones of Tumorigenesis," Trends in Biochemical Sciences 31(3):164-172, Elsevier Trends Journals, England (2006).
Cho, Y.J., "GemVax & Kael (082270)," Hana Daetoo Securities, Company Report, Sep. 10, 2012, 9 pages.
Choi, S.G., "Recent Advances in Cancer Cachexia," Journal of Korean Oncology Nursing 11(1):20-25 (2011).
ClinicalTrials.gov, "Adjuvant Leuprolide with or without Docetaxel in High Risk Prostate Cancer After Radial Prostatectomy," Identifier NCT00283062, first received on Jan. 26, 2006, accessed at https://clinicaltrials.gov/ct2/show/study/NCT00283062, last accessed on May 12, 2017, 7 pages.
ClinicalTrials.gov, "Gemcitabine, Capecitabine, and Telomerase Peptide Vaccine GV1001 in Treating Patients With Locally Advanced and Metastatic Pancreatic Cancer," Identifier NCT00425360, accessed at https://clinicaltrials.gov/archive/NCT00425360/2007_01_22, last accessed on Apr. 7, 2017, 4 pages.
Co-pending U.S. Appl. No. 15/772,928, inventors Kim, S.J., et al., filed Nov. 3, 2016 (Not Published).
Dahlgren, K.N., et al., "Oligomeric and Fibrillar Species of Amyloid-beta Peptides Differentially Affect Neuronal Viability," Journal of Biological Chemistry 277(35):32046-32053, American Society for Biochemistry and Molecular Biology, United States (2002).
De Araujo, J.G., et al., "The Potential Use of Melatonin for Preventing Cisplatin Ototoxicity: An Insight for a Clinical Approach," Advances in Otolaryngology 2014:8 pages, Hindawi Publishing Corporation (2014).
Delves, P.J., "Allergic Rhinitis," Merck manual, accessed at http://www.merckmanuals.com/professional/immunology-allergic-disorders/allergic,-autoimmune,-and-other-hypersensitivity-disorders/allergic-rhinitis, accessed on Nov. 2, 2017, pp. 1-6.
Dementia from Merck Manual, accessed on Jul. 29, 2009, pp. 1-17.
Dempsey, N.C., et al., "Differential Heat Shock Protein Localization in Chronic Lymphocytic Leukemia," Journal of Leukocyte Biology 87(3):467-476, Society for Leukocyte Biology, United States (2010).
Dinarello, C.A., "Interleukin-1 in the Pathogenesis and Treatment of Inflammatory Diseases," Blood 117(14):3720-3732, American Society of Hematology, United States (2011).
Du, C., et al., "Conformational and Topological Requirements of Cell-permeable Peptide Function," The Journal of Peptide Research 51(3):235-243, Munksgaard, Denmark (1998).
Du, R., et al., "HIF1 alpha Induces the Recruitment of Bone Marrow-derived Vascular Modulatory Cells to Regulate Tumor Angiogenesis and Invasion," Cancer Cell 13(3):206-220, Cell Press, United States (2008).
Eisenegger, C., et al., "The Role of Testosterone in Social Interaction," Trends in Cognitive Sciences 15(6):263-271, Elsevier Science, England (2011).
Engineer, D.R. and Garcia, J.M., "Leptin in Anorexia and Cachexia Syndrome," International Journal of Peptides 2012:Article ID 287457, Hindawi Publishing Corporation, United States (2012).
"Seoul National University Bundang Hospital excited because of '000'," Clinical trials of Dream Anticancer Drug without side effects with Kael & GemVax, 4 pages, Apr. 22, 2013.
Eustace, B.K. and Jay, D.G., "Extracellular Roles for the Molecular Chaperone, Hsp90," Cell Cycle 3(9):1098-1100, Taylor & Francis, United States (2004).
Eustace, B.K. and Jay, D.G., "Functional Proteomic Screens Reveal an Essential Extracellular Role for Hsp90 Alpha in Cancer Cell Invasiveness," Nature Cell Biology 6(6):507-514, Macmillan Magazines Ltd., England (2004).
Evans, C.G., et al., "Heat Shock Protein 70 (Hsp70) as an Emerging Drug Target," Journal of Medicinal Chemistry 53(12):4585-4602, American Chemical Society, United States (2010).

Extended European Search Report for Application No. EP14808179, dated May 24, 2017, 24 pages.
Fauce, S.R., et al., "Telomerase-Based Pharmacologic Enhancement of Antiviral function of Human CD8+ T Lymphocytes," Immunology 181(10):7400-7406, American Association of Immunologists, United States (Nov. 2008).
Ferrarini, M., et al., "Unusual Expression and Localization of Heat-shock Proteins in Human Tumor Cells," International Journal of Cancer 51(4):613-619, Wiley-Liss, United States (1992).
Fire, A., et al., "Potent and Specific Genetic Interference by Double-stranded RNA in Caenorhabditis Elegans," Nature 391(6669):806-811, Nature Publishing Group, England (1998).
Fittipaldi, A., et al., "Cell Membrane Lipid Rafts Mediate Caveolar Endocytosis of HIV-1 Tat Fusion Proteins," Journal of Biological Chemistry 278(36): 34141-34149, American Society for Biochemistry and Molecular Biology, United States (2003).
Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).
Fontanes, V., et al., "A cell permeable peptide inhibits Hepatitis C Virus Replication by Sequestering IRES Transacting Factors," Virology 394(1):82-90, Academic Press, United States (Nov. 2009).
Fried, M.P., "Nonallergic Rhinitis," Merck manual, accessed at http://www.msdmanuals.com/professional/ear,-nose,-and-throat-disorders/nose-and-paranasal-sinus-disorders/nonallergic-rhinitis, accessed on Nov. 2, 2017, pp. 1-3.
Fujii, H., et al., "Telomerase Insufficiency in Rheumatoid Arthritis," Proceedings of the National Academy of Sciences USA 106(11):4360-4365, National Academy of Sciences, United States (2009).
Garcia-Carbonero, R., et al., "Inhibition of HSP90 Molecular Chaperones: Moving Into the Clinic," The Lancet Oncology 14(9):e358-e369, Lancet Publishing Group, England (2013).
GemVax Receives Report on Anti-Inflammatory Mechanism, The Asia Economy Daily, Article written on May 7, 2013.
Ghaneh, P., et al., "Biology and Management of Pancreatic Cancer," Gut 56(8):1134-1152, British Medical Association, England (2007).
Gong, W., et al., "Invasion Potential of H22 Hepatocarcinoma Cells is Increased by HMGB1-induced Tumor NF-κB Signaling via Initiation of HSP70," Oncology Reports 30(3):1249-1256, D.A. Spandidos, Greece (2013).
Granger, D.N. and Korthuis, R.J., "Physiologic Mechanisms of Postischemic Tissue Injury," Annual Review of Physiology 57:311-332, Annual Reviews, United States (1995).
Gunturu, K.S., et al., "Immunotherapy Updates in Pancreatic Cancer: Are we there yet?," Therapeutic Advances in Medical Oncology 5(1):81-89, Sage, England (2013).
Guo, R.F., et al., "Regulatory Effects of Eotaxin on Acute Lung Inflammatory Injury," Journal of Immunology 166(8):5208-5218, American Association of Immunologists, United States (2001).
Heitz, F., et al., "Twenty Years of Cell-Penetrating Peptides: From Molecular Mechanisms to Therapeutics," British Journal of Pharmacology 157(2):195-206, Wiley, England (2009).
Heldin, C.H., et al., "TGF-Beta Signalling from Cell Membrane to Nucleus through SMAD Proteins," Nature 390(6659):465-471, Nature Publishing Group, England (1997).
Henry, J.Y., et al., "Lenalidomide Enhances the Anti-prostate Cancer Activity of Docetaxel in vitro and in vivo," The Prostate 72(8):856-867, Wiley-Liss, United States (2012).
Hse, "Rheumatoid arthritis," http://www.hse.ie/portal/eng, accessed at http://www.hse.ie/portal/eng/health/az/R/Rheumatoid-arthritis/, 14 pages (2013).
Inderberg-Suso, E.M., et al., "Widespread CD4+ T-cell Reactivity to Novel hTERT Epitopes following Vaccination of Cancer Patients with a Single hTERT Peptide GV1001," Oncoimmunology 1(5):670-686, Taylor and Francis, United States (2012).
International Preliminary Report on Patentability and Written Opinion for International Application No. PCT/KR2015/014099, The International Bureau of WIPO, dated Jun. 27, 2017, 16 pages.
International Preliminary Report on Patentability and Written Opinion for International Application No. PCT/KR2016/001646, Korean Intellectual Property Office, Republic of Korea, dated May 20, 2016, 13 pages.

(56) References Cited

OTHER PUBLICATIONS

International Preliminary Report on Patentability for Application No. PCT/KR2014/004752, The International Bureau of WIPO, Switzerland, dated Nov. 1, 2016, 23 pages.
International Preliminary Report on Patentability for Application No. PCT/KR2015/003642, The International Bureau of WIPO, Switzerland, dated Oct. 12, 2016, 18 pages.
International Preliminary Report on Patentability for International Application No. PCT/KR2014/011280, The International Bureau of WIPO, Geneva, Switzerland, dated May 24, 2016, 15 pages.
International Preliminary Report on Patentability for International Application No. PCT/KR2014/012502, The International Bureau of WIPO, Geneva, Switzerland, dated Jun. 21, 2016, 22 pages.
International Preliminary Report on Patentability for International Application No. PCT/EP2013/059460, International Bureau of WIPO, Switzerland, dated Nov. 11, 2014, 5 pages.
International Preliminary Report on Patentability for International Application No. PCT/KR2013/004145, The International Bureau of WIPO, Switzerland, dated Nov. 11, 2014, 14 pages.
International Preliminary Report on Patentability for International Application No. PCT/KR2013/004176, The International Bureau of WIPO, Switzerland, dated Nov. 11, 2014, 14 pages.
International Preliminary Report on Patentability for International Application No. PCT/KR2013/006218, The International Bureau of WIPO, Switzerland, dated Jan. 13, 2015, 27 pages.
International Preliminary Report on Patentability for International Application No. PCT/KR2013/008438, The International Bureau of WIPO, Switzerland, dated Mar. 24, 2015, 10 pages.
International Preliminary Report on Patentability for International Application No. PCT/KR2013/008445, The International Bureau of WIPO, Switzerland, dated Mar. 24, 2015, 13 pages.
International Preliminary Report on Patentability for International Application No. PCT/KR2014/003425, The International Bureau of WIPO, Switzerland, dated Oct. 20, 2015, 14 pages.
International Preliminary Report on Patentability for International Application No. PCT/KR2014/005031, The International Bureau of WIPO, Switzerland, dated Dec. 8, 2015, 8 pages.
International Preliminary Report on Patentability for International Application No. PCT/KR2014/005508, The International Bureau of WIPO, Switzerland, dated Jan. 5, 2016, 14 pages.
International Preliminary Report on Patentability for International Application No. PCT/KR2014/010035, Korean Intellectual Property Office, Republic of Korea, dated Apr. 26, 2016, 13 pages.
International Preliminary Report on Patentability for International Patent Application No. PCT/KR2013/004156, the International Bureau of WIPO, Geneva, Switzerland, dated Nov. 11, 2014, 15 pages.
International Search Report and Written Opinion for International Application No. PCT/KR2016/012613, Korean Intellectual Property Office, Republic of Korea, dated Feb. 2, 2017, 14 pages.
International Search Report for Application No. PCT/KR2016/007192, dated Sep. 12, 2016, 12 pages.
International Search Report for International Application No. PCT/KR2014/003425, Korean Intellectual Property Office, Republic of Korea, dated Jul. 21, 2014, 8 pages.
International Search Report for International Application No. PCT/KR2014/011280, Korean Intellectual Property Office, Republic of Korea, dated Feb. 11, 2015, 12 pages.
International Search Report for International Application No. PCT/KR2014/012502, Korean Intellectual Property Office, Republic of Korea, dated Mar. 11, 2015, 10 pages.
International Search Report for International Application No. PCT/KR2015/014099, Korean Intellectual Property Office, Republic of Korea, dated May 4, 2016, 8 pages.
International Search Report for International Application No. PCT/KR2016/001646, Korean Intellectual Property Office, Republic of Korea, dated May 20, 2016, 8 pages.
International Search Report for International Application No. PCT/EP2013/059460, European Patent Office, Netherlands, dated Jul. 3, 2013, 5 pages.
International Search Report for International Application No. PCT/KR2013/004145, Korean Intellectual Property Office, Republic of Korea, dated Aug. 14, 2013, 10 pages.
International Search Report for International Application No. PCT/KR2013/004176, Korean Intellectual Property Office, Republic of Korea, dated Aug. 6, 2013, 10 pages.
International Search Report for International Application No. PCT/KR2013/006218, Korean Intellectual Property Office, Republic of Korea, dated Sep. 26, 2013, 8 pages.
International Search Report for International Application No. PCT/KR2013/008438, Korean Intellectual Property Office, Republic of Korea, dated Dec. 23, 2013, 8 pages.
International Search Report for International Application No. PCT/KR2013/008445, Korean Intellectual Property Office, Republic of Korea, dated Dec. 23, 2013, 10 pages.
International Search Report for International Application No. PCT/KR2013/008459, Korean Intellectual Property Office, Republic of Korea, dated Dec. 23, 2013, 8 pages.
International Search Report for International Application No. PCT/KR2014/004752, Korean Intellectual Property Office, Republic of Korea, dated Jan. 16, 2015, 10 pages.
International Search Report for International Application No. PCT/KR2014/005031, Korean Intellectual Property Office, Republic of Korea, dated Sep. 22, 2014, 6 pages.
International Search Report for International Application No. PCT/KR2014/005508, Korean Intellectual Property Office, Republic of Korea, dated Oct. 14, 2014, 8 pages.
International Search Report for International Application No. PCT/KR2014/010035, Korean Intellectual Property Office, Republic of Korea, dated Feb. 2, 2015, 8 pages.
International Search Report for International Application No. PCT/KR2015/003642, Korean Intellectual Property Office, Republic of Korea, dated Jul. 3, 2015, 8 pages.
International Search Report for International Patent Application No. PCT/KR2013/004156, Korean Intellectual Property Office, Republic of Korea, dated Aug. 14, 2013, 10 pages.
Jaattela, M., "Over-expression of Hsp70 Confers Tumorigenicity to Mouse Fibrosarcoma Cells," International Journal of Cancer 60(5):689-693, Wiley-Liss, United States (1995).
Jain, R.K., "Barriers to Drug Delivery in Solid Tumors," Scientific American 271(1):58-65, Scientific American, Inc., United States (Jul. 1994).
Jemal, A., et al., "Cancer Statistics, 2008," CA: A Cancer Journal for Clinicians 58(2):71-96, Wiley, United States (2008).
Kalnins, A., et al., "Sequence of the Lacz Gene of *Escherichia coli*," The EMBO Journal 2(4):593-597, Wiley Blackwell, England (1983).
Kawasaki, H., et al., "Detection and Evaluation of Activation of Various Cancer Antigenic Peptide-specific CTLs in Mature Dendritic Cells Used for Dendritic Cell Therapy," The21st International Congress of Personalized Medicine, Conference Program and Abstracts, Personalized Medicine Universe (Japanese edition) 4(Supplement 2): 2 pages, Oct. 17, 2015.
Kern, K.A. and Norton, J.A., "Cancer Cachexia," Journal of Parenteral and Enteral Nutrition 12(3):286-298, Sage Publications, United States (1988).
Kim, B.H., "Presbycusis: Review for its Environmental Risk Factors," Korean Journal of Otorhinolaryngology-Head and Neck Surgery 49(10):962-967, Korean Society of Otolaryngology-Head and Neck Surgery, Korea (2006).
Kim, B.K., et al., "Tumor-suppressive Effect of a Telomerase-derived Peptide by Inhibiting Hypoxia-induced HIF-1α-VEGF Signaling Axis," Biomaterials 35(9):2924-2933, Elsevier Science, Netherlands (2014).
Kim, H., et al., "Inhibition of HIV-1 Reactivation by a Telomerase-Derived Peptide in a HSP90-Dependent Manner," Scientific Reports 6: 28896, Nature Publishing Group, England (Jul. 2016).
Kim, H.O. and Lee, S.I., "Experimental Animal Models for Rheumatoid Arthritis: Methods and Applications," Journal of Rheumatic Diseases 19(4):189-195, The Korean College of Rheumatology, Republic of Korea(2012).
Kirino, T, "Delayed Neuronal Death in the Gerbil Hippocampus Following Ischemia," Brain Research 239(1):57-69, Amsterdam Elsevier/North-Holland Biomedical Press, Netherlands (May 1982).

(56) References Cited

OTHER PUBLICATIONS

Kocsis, J., et al., "Serum Level of Soluble 70-kD Heat Shock Protein is Associated With High Mortality in Patients With Colorectal Cancer Without Distant Metastasis," Cell Stress & Chaperones 15(2):143-151, Springer, Netherlands (2010).
Kokhaei, P., et al., "Telomerase (hTERT 611-626) Serves as a Tumor Antigen in B-cell Chronic Lymphocytic Leukemia and Generates Spontaneously Antileukemic, Cytotoxic T Cells," Experimental Hematology 35(2):297-304, Elsevier Science Inc., Netherlands (2007).
Kyte, J.A., "Cancer Vaccination with Telomerase Peptide GV1001," Expert Opinion on Investigational Drugs 18(5):687-694, Taylor & Francis, England (2009).
Kyte, J.A., et al., "Telomerase Peptide Vaccination Combined with Temozolomide: A Clinical Trial in Stage IV Melanoma Patients," Clinical Cancer Research 17(13):4568-4580,American Association of Cancer Research, United States (2011).
Lahdevirta, J., et al., "Elevated Levels of Circulating Cachectin/tumor Necrosis Factor in Patients with Acquired Immunodeficiency Syndrome," American Journal of Medicine 85(3):289-291, Excerpta Medica, United States (1988).
Laviano, A., et al., "Therapy Insight: Cancer Anorexia-cachexia Syndrome—When All You Can Eat is Yourself," Nature Clinical Practice. Oncology 2(3):158-165, Nature Publishing Group, England (2005).
Lee, E.K., et al., "Inhibition of Experimental Choroidal Neovascularization by Telomerase-derived Peptide GV1001," Investigative Ophthalmology & Visual Science 56(7):Abstract 2291, ARVO Annual Meeting Abstract (Jun. 2015).
Lee, S.A., et al., "A Telomerase-Derived Peptide Regulates Reactive Oxygen Species and Hepatitis C Virus RNA Replication in HCV-Infected Cells Via Heat Shock Protein 90," Biochemical and Biophysical Research Communications 471(1):156-162, Elsevier, United States (Feb. 2016).
Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).
Leem G., et al., Immunotherapy in Pancreatic Cancer; the Road Less Traveled Immunol Disord Immunotherapy, Jun. 26, 2016 (Jun. 26, 2016), p. 1000106, XP055328627, Retrieved from the Internet: (URL:http://www.omicsgroup.orgjjournalsjimmunotherapy-in-pancreatic-cancer-the-road-less-traveled-IDIT-1000104.pdf).
Liu, Q.J., et al., "Rapamycin Enhances the Susceptibility of Both Androgen-dependent and -independent Prostate Carcinoma Cells to Docetaxel," Chinese Medical Journal 123(3):356-360, Chinese Medical Association, China (2010).
Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).
Mandal, A., "Types of Fibrosis," Retrieved from the internet on Jul. 3, 2014, pp. 1-3.
Martinez, P. and Blasco, M.A., "Telomeric and Extra-telomeric Roles for Telomerase and the Telomere-binding Proteins," Nature Reviews Cancer 11(3):161-176, Nature Publishing Group, England (2011).
Massague, J., "Tgf-Beta Signal Transduction," Annual Review of Biochemistry 67:753-791, Annual Reviews, United States (1998).
Mattson, M.P., "Pathways Towards and Away From Alzheimer's Disease," Nature 430(7000):631-639, Nature Publishing Group, England (2004).
McConnell, J.D., et al., "The Effect of Finasteride on the Risk of Acute Urinary Retention and the Need for Surgical Treatment Among Men with Benign Prostatic Hyperplasia. Finasteride Long-term Efficacy and Safety Study Group," The New England Journal of Medicine 338(9):557-563, Massachusetts Medical Society, United States (1998).

Merck Manual: Respiratory Diseases, Medical Topics, accessed on Nov. 2, 2017, pp. 1-4.
Merck, "Obesity, The Merck Manual Professional Edition," accessed at https://www.merckmanuals.com/professional/nutritional-disorders/obesity-and-the-metabolic-syndrome/obesity, accessed on Oct. 6, 2014, 9 pages.
Middleton, G., et al., "Gemcitabine and Capecitabine With or Without Telomerase Peptide Vaccine GV1001 in Patients With Locally Advanced or Metastatic Pancreatic Cancer (TeloVac): an Open-label, Randomised, Phase 3 Trial," The Lancet. Oncology 15(8):829-840, Lancet Pub. Group, England (2014).
Middleton, G.W., "A Phase III Randomized Trial of Chemoimmunotherapy Comprising Gemcitabine and Capecitabine with or Without Telomerase Vaccine GV1001 in Patients with Locally Advanced or Metastatic Pancreatic Cancer," Presented at conference ASCO, (Jun. 4, 2013), XP054977010. Retrieved from the Internet: (URL: http://meetinglibrary.asco.orgjcontent/82894?media=vm).
Middleton, G.W., et al., Phase III Randomized Trial of Chemoimmunotherapy Comprising Gemcitabine and Capecitabine with or without Telomerase Vaccine GV1001 in Patients with Locally Advanced or Metastatic Pancreatic Cancer, ASCO Annual Meeting, 31:1-3, (May 31, 2013)-(Jun. 4, 2013), XP055328310.
Middleton, G.W., et al., Poster: Predictive Cytokine Biomarkers for Survival in Patients with Advanced Pancreatic Cancer Randomized to Sequential Chemoimmunotherapy Comprising Gemcitabine and Capecitabine (GemCap) Followed by the Telomerase Vaccine GV1001 Compared to Concurrent Chemoimmunotherapy in the Telovac Phase III tr, ASCO 2014, May 30, 2014 (May 30, 2014)-Jun. 3, 2014 (Jun, 3, 2014), pp. 1-1. XP055328448. Retrieved from the Internet: (URL:http://media4.asco.org/144/8599/93976/93976_poster_pvh.jpg).
Modica-Napolitano, J.S. and Singh, K.K., "Mitochondria as Targets for Detection and Treatment of Cancer," Expert Reviews in Molecular Medicine 4(9):1-19, Cambridge University Press, England (2002).
Morano, K.A., "New Tricks for an Old Dog: the Evolving World of Hsp70," Annals of the New York Academy of Sciences 1113:1-14, Blackwell, United States (2007).
Morishita, M., and Peppas, N.A., "Is the Oral Route Possible for Peptide and Protein Drug Delivery?," Drug Discovery Today 11(19-20):905-910, Elsevier Science Ltd., England (2006).
Murphy, M.E., "The Hsp70 Family and Cancer," Carcinogenesis 34(6):1181-1188, Irl Press, England (2013).
Myers, L.K., et al., "Collagen-Induced Arthritis, an Animal Model of Autoimmunity," Life Sciences 61(19):1861-1878, Elsevier, Netherlands (1997).
Nagaraju, G.P., et al., "Antiangiogenic Effects of Ganetespib in Colorectal Cancer Mediated Through Inhibition of HIF-1$\alpha$ and STAT-3," Angiogenesis 16(4):903-917, Springer, Germany (2013).
National Center for Biotechnology Information, "Hormones," MeSH Database, Bethesda, accessed at http://www.ncbi.nlm.nih.gov/mesh/68006728, accessed on May 8, 2017, 3 pages.
National Horizon Scanning Centre News on Emerging Technologies in Healthcare, GV1001 for Advanced and/or Metastatic Pancreatic Cancer, Published Apr. 2008.
National Institute of Diabetes and Digestive and Kidney Diseases, "Prostate Enlargement: Benign Prostatic Hyperplasia," accessed at https://www.niddk.nih.gov/health-information/urologic-diseases/prostate-problems/prostate-enlargement-benign-prostatic-hyperplasia, accessed Sep. 2014, 14 pages.
Nawroth, I., et al., "Intraperitoneal Administration of Chitosan/DsiRNA Nanoparticles Targeting TNF$\alpha$ Prevents Radiation-induced Fibrosis," Radiotherapy and Oncology 97(1):143-148, Elsevier Scientific Publishers, Ireland (2010).
NCBI, Reference Sequence: XP_003776612.1 (Jul. 17, 2012).
Neoptolemos J.P., et al., "Predictive 1-20 Cytokine Biomarkers for Survival in Patients With Advanced Pancreatic Cancer Randomized to Sequential Chemoimmunotherapy Comprising Gemcitabine and Capecitabine (Gemcap) Followed by the Telomerase Vaccine GV1001 Compared to Concurrent Chemoimmunotherapy in the Telovac Phase III trial," 2014 ASCO Annual Meeting, May 30, 2014 (May 39, 2014)-Jun. 3, 2014 (Jun. 3, 2014), pp. 1-3.

(56) References Cited

OTHER PUBLICATIONS

Ngo. et al., "Computational Complexity, Protein Structure Prediction, and the Levinthal Paradox," in The Protein Folding Problem and Tertiary Structure Prediction, Merz, Jr., K.M., and Le Grand, S.M., eds., pp. 491-494, Birkhauser Boston, United States (1994).

Novina, C.D. and Sharp, P.A., "The RNAi Revolution," Nature 430(6996):161-164, Nature Publishing Group, England (2004).

O'Beirne, J., et al., "Generation of Functional CD8+ T Cells by Human Dendritic Cells Expressing Glypican-3 Epitopes," in: Journal of Experimental and Clinical Cancer Research 29:48, BioMed Central, London (May 2010).

Oh, H., et al., "Telomerase Reverse Transcriptase Promotes Cardiac Muscle Cell Proliferation, Hypertrophy, and Survival," Proceedings of the National Academy of Sciences USA 98(18): 10308-10313, National Academy of Sciences, United States (2001).

Olney, J.W., et al., "Pathological Changes Induced in Cerebrocortical Neurons by Phencyclidine and Related Drugs," Science 244(4910):1360-1362, American Association for the Advancement of Science, United States (Jun. 1989).

Ortega, V.E., "Asthma," Merck manual, accessed at http://www.merckmanuals.com/professional/pulmonary-disorders/asthma-and-related-disorders/asthma, accessed on Nov. 2, 2017, pp. 1-19.

Pearson, W.R. and Lipman, D.J., "Improved Tools for Biological Sequence Comparison," Proceedings of the National Academy of Sciences of the United States of America 85(8):2444-2448, National Academy of Sciences, United States (1988).

Perez, R.G., et al., "The Beta-amyloid Precursor Protein of Alzheimer's Disease Enhances Neuron Viability and Modulates Neuronal Polarity," The Journal of Neuroscience 17(24):9407-9414, Society for Neuroscience, United States (1997).

Pfosser, A., et al., "Liposomal HSP90 Cdna Induces Neovascularization via Nitric Oxide in Chronic Ischemia," Cardiovascular Research 65(3):728-736, Oxford Journals, England (2005).

Powers, M.V., et al., "Targeting HSP70: the Second Potentially Druggable Heat Shock Protein and Molecular Chaperone?," Cell Cycle 9(8):1542-1550, Taylor & Francis, United States (2010).

Priya, S.G., et al., "Skin Tissue Engineering for Tissue Repair and Regeneration," Tissue Engineering. Part B, Reviews 14(1):105-118, Mary Ann Liebert, Inc., United States (2008).

Rana, T.M., "Illuminating the Silence: Understanding the Structure and Function of Small RNAs," Nature Reviews. Molecular Cell Biology 8(1):23-36, Nature Publishing Group, England (2007).

Rheumatoid Arthritis from Merck Manual, accessed on Apr. 21, 2016, pp. 1-18.

Rosenbloom, J., et al., "Strategies for Anti-fibrotic Therapies," Biochimica et Biophysica Acta 1832(7):1088-1103, Elsevier Pub. Co., Netherlands (2013).

Rosenstein, B.J., "Cystic Fibrosis," Merck manual, accessed at http://www.msdmanuals.com/professional/pediatrics/cystic-fibrosis-cf/cystic-fibrosis, accessed on Nov. 2, 2017, pp. 1-15.

Roubenoff, R., et al., "Adjuvant Arthritis as a Model of Inflammatory Cachexia," Arthritis and Rheumatism 40(3):534-539, Wiley-Blackwell, United States (1997).

Rowe-Rendleman, C. and Glickman, R.D., "Possible therapy for age-related macular degeneration using human telomerase," Brain Research Bulletin 62(6):549-553, Elsevier Science Inc., United States (2004).

Rudinger, J., "Characteristics of the Amino Acids as Components of a Peptide Hormone Sequence," in Peptide Hormones, Parsons, J.A., ed., University Park Press, United States (1976).

Sasada, A., et al., "A Case of Elderly Patient With Lung Cancer Efficiently Treated With Dendritic Cell Immunotherapy" The 20th International Congress of Personalized Medicine, Conference Program and Abstracts, Personalized Medicine Universe (Japanese edition) 4(Supplement 1): 2 pages, May 24, 2015.

Sayers, S., et al., "Vaxjo: A Web-based Vaccine Adjuvant Database and its Application for Analysis of Vaccine Adjuvants and their Uses in Vaccine Development," Journal of Biomedicine and Biotechnology 2012:1-13, Article ID 831486, Hindawi Publishing Corporation, United States (2012).

Schenk, D., et al., "Immunization with Amyloid-beta Attenuates Alzheimer-disease-like Pathology in the PDAPP Mouse," Nature 400(6740):173-177, Nature Publishing Group, England (1999).

Schlapbach, C., et al., "Telomerase-specific GV1001 Peptide Vaccination Fails to Induce Objective Tumor Response in Patients with Cutaneous T Cell Lymphoma," Journal of Dermatological Science 62(2):75-83, Elsevier, Netherlands (2011).

Schwarze, S.R., et al., "In Vivo Protein Transduction: Delivery of a Biologically Active Protein Into the Mouse," Science 285(5433):1569-1572, American Association for the Advancement of Science, United States (1999).

Seo, J.S., et al., "T Cell Lymphoma in Transgenic Mice Expressing the Human Hsp70 Gene," Biochemical and Biophysical Research Communications 218(2):582-587, Elsevier, United States (1996).

Shaw, V.E., et al., "Current Status of GV1001 and Other Telomerase Vaccination Strategies in the Treatment of Cancer," Expert Review of Vaccines 9(9):1007-1016, Taylor & Francis, England (2010).

Shay, J.W., and Wright, W.E., "Telomerase Therapeutics for Cancer: Challenges and New Directions," Nature Reviews. Drug Discovery 5(7):577-584, Nature Publishing Group, England (2006).

SIGMA Genosys, "Designing Custom Peptides," accessed at http://www.sigma-genosys.com/peptide_design.asp, Accessed on Dec. 16, 2004, 2 pages.

Smith, D.B. and Johnson, K.S., "Single-step Purification of Polypeptides Expressed in *Escherichia coli* as Fusions with Glutathione S-transferase," Gene 67(1):31-40, Elsevier, Netherlands (Jul. 1988).

Smith, T.F. and Waterman, M.S., "Comparison of Biosequences," Advances in Applied Mathematics 2(4):482-489, Academic Press, Inc., United States (Dec. 1981).

Song, J., et al., "Characterization and Fate of Telomerase-Expressing Epithelia during Kidney Repair," Journal of the American Society of Nephrology 22(12):2256-2265, American Society of Nephrology, United States (2011).

Southern Cross, "Rheumatoid arthritis—causes, symptoms, and treatment," https://www.southerncross.co.nz/, accessed at https://www.southerncross.co.nz/AboutTheGroup/HealthResources/MedicalLibrary/tabid/178/vw/1/itemID/124/Rheumatoid-arthritis-causes-symptoms-treatment.aspx, last reviewed on May 31, 2013, 5 pages.

Stevenson, C.L., "Advances in Peptide Pharmaceuticals," Current Pharmaceutical Biotechnology 10(1):122-137, Bentham Science Publishers, United Arab Emirates (2009).

Sun, J., et al., "Induction of Angiogenesis by Heat Shock Protein 90 Mediated by Protein Kinase Akt and Endothelial Nitric Oxide Synthase," Arteriosclerosis, Thrombosis, and Vascular biology 24(12):2238-2244, Lippincott Williams & Wilkins, United States (2004)..

Supplemental European Search Report for Application No. EP14808179, dated Jan. 10, 2017, 13 pages.

Taylor, P.C. and Feldmann, M., "Anti-TNF Biologic Agents: Still the Therapy of Choice for Rheumatoid Arthritis," Nature Reviews. Rheumatology 5(10):578-582, Macmillan Publishers Limited, England (2009).

Thompson, J.D., et al., "CLUSTAL W: Improving the Sensitivity of Progressive Multiple Sequence Alignment through Sequence Weighting, Position-specific Gap Penalties and Weight Matrix Choice," Nucleic Acids Research 22(22):4673-4680, Oxford University Press, England (Nov. 1994).

Tisdale, M.J., "Catabolic Mediators of Cancer Cachexia," Current Opinion in Supportive and Palliative Care, 2(4):256-261, Lippincott Williams & Wilkins, United States (2008).

Tisdale, M.J., "Mechanisms of Cancer Cachexia," Physiological Reviews 89(2):381-410, American Physiological Society, United States (2009).

Tomari Y. and Zamore, P.D., "Perspective: Machines for RNAi," Genes and Development 19(5):517-529, Cold Spring Harbor Laboratory Press, United States (2005).

Uehara, Y., "Natural Product Origins of Hsp90 Inhibitors," Current Cancer Drug Targets 3(5):325-330, Bentham Science Publishers, Netherlands (2003).

Van Coppenolle, F., et al., "Effects of Hyperprolactinemia on Rat Prostate Growth: Evidence of Androgeno-dependence," American

(56) References Cited

OTHER PUBLICATIONS

Journal of Physiology. Endocrinology and Metabolism 280(1):E120-E129, American Physiological Society, United States (2001).
Vanbuskirk, A., et al., "A Peptide Binding Protein Having a Role in Antigen Presentation is a Member of the HSP70 Heat Shock Family," The Journal of Experimental Medicine 170(6):1799-1809, Rockefeller University Press, United States (1989).
Varma, N., et al., "Role of hTERT and WT1 Gene Expression in Disease Progression and Imatinib Responsiveness of Patients with BCR-ABL Positive Chronic Myeloid Leukemia," in: Leukemia and Lymphoma 52(4):687-693, Informa Healthcare, London (Apr. 2011).
Vennela, B., et al., "Current and Future Strategies for Therapy of Pancreatic Cancer," International Journal of Research in Pharmacy and Medicine 2(3):728-740 (2012).
Voet, D. and Voet, J.G., "Abnormal Hemoglobins," in Biochemistry, 2nd Edition, Chapter 9, pp. 235-241, John Wiley & Sons, Inc., United States (1995).
Volloch, V.Z. and Sherman, M.Y., "Oncogenic Potential of Hsp72," Oncogene 18(24):3648-3651, Nature Publishing Group, England (1999).
Walsmith, J. and Roubenoff, R., "Cachexia in Rheumatoid Arthritis," International Journal of Cardiology 85(1):89-99, Elsevier, Netherlands (2002).
Wang, W., et al., "Alleviating the Ischemia-Reperfusion Injury of Donor Liver by Transfection of Exogenous hTERT Genes," Transplantation Proceedings 41(5):1499-1503, Elsevier Science, United States (2009).
Westin, E.R., et al., "The p53/p21(WAF/CIP) Pathway Mediates Oxidative Stress and Senescence in Dyskeratosis Congenita Cells With Telomerase Insufficiency," Antioxidants & Redox Signaling 14(6):985-997, Mary Ann Liebert, Inc., United States (2011).
Written opinion for Application No. PCT/KR2016/007192, dated Sep. 12, 2016, 16 pages.
Written Opinion for International Application No. PCT/KR2014/003425, Korean Intellectual Property Office, Republic of Korea, dated Jul. 21, 2014, 13 pages.
Written Opinion for International Application No. PCT/KR2014/011280, Korean Intellectual Property Office, Republic of Korea, dated Feb. 11, 2015, 14 pages.
Written Opinion for International Application No. PCT/KR2014/012502, Korean Intellectual Property Office, Republic of Korea, dated Mar. 11, 2015, 20 pages.
Written Opinion for International Application No. PCT/EP2013/059460, European Patent Office, Germany, dated Jul. 3, 2013, 4 pages.
Written Opinion for International Application No. PCT/KR2013/004145, Korean Intellectual Property Office, Republic of Korea, dated Aug. 14, 2013, 13 pages.
Written Opinion for International Application No. PCT/KR2013/004176, Korean Intellectual Property Office, Republic of Korea, dated Aug. 6, 2013, 13 pages.
Written Opinion for International Application No. PCT/KR2013/006218, Korean Intellectual Property Office, Republic of Korea, dated Sep. 26, 2013, 26 pages.
Written Opinion for International Application No. PCT/KR2013/008438, Korean Intellectual Property Office, Republic of Korea, dated Dec. 23, 2013, 9 pages.
Written Opinion for International Application No. PCT/KR2013/008445, Korean Intellectual Property Office, Republic of Korea, dated Dec. 23, 2013, 12 pages.
Written Opinion for International Application No. PCT/KR2013/008459, Korean Intellectual Property Office, Republic of Korea, dated Dec. 23, 2013, 9 pages.
Written Opinion for International Application No. PCT/KR2014/004752, Korean Intellectual Property Office, Republic of Korea, dated Jan. 16, 2015, 21 pages.
Written Opinion for International Application No. PCT/KR2014/005031, Korean Intellectual Property Office, Republic of Korea, dated Sep. 22, 2014, 7 pages.
Written Opinion for International Application No. PCT/KR2014/005508, Korean Intellectual Property Office, Republic of Korea, dated Oct. 14, 2014, 13 pages.
Written Opinion for International Application No. PCT/KR2014/010035, Korean Intellectual Property Office, Republic of Korea, dated Feb. 2, 2015, 11 pages.
Written Opinion for International Application No. PCT/KR2015/003642, Korean Intellectual Property Office, Republic of Korea, dated Jul. 3, 2015, 16 pages.
Written Opinion for International Patent Application No. PCT/KR2013/004156, Korean Intellectual Property Office, Republic of Korea, dated Aug. 14, 2013, 13 pages.
Wynn, T.A. and Ramalingam, T.R., "Mechanisms of Fibrosis: Therapeutic Translation for Fibrotic Disease," Nature Medicine 18(7):1028-1040, Nature Publishing Company, United States (2012).
Yankner, B.A., et al., "Neurotrophic and Neurotoxic Effects of Amyloid Beta Protein: Reversal by Tachykinin Neuropeptides," Science 250(4978):279-282, American Association for the Advancement of Science, United States (1990).
Yeh, C.H., et al., "Clinical Correlation of Circulating Heat Shock Protein 70 in Acute Leukemia," Leukemia Research 34(5):605-609, Pergamon Press, England (2010).
Yi, A., et al., "Radiation-Induced Complications after Breast Cancer Radiation Therapy: a Pictorial Review of Multimodality Imaging Findings," Korean Journal of Radiology 10(5):496-507, Korean Society of Radiology, Korea (2009).
Zhang, H., et al., "Inhibiting TGFβ1 has a Protective Effect on Mouse Bone Marrow Suppression Following Ionizing Radiation Exposure in Vitro," Journal of Radiation Research 54(4):630-636, Oxford University Press, England (2013).
Zhou, J., et al., "PI3K/Akt is Required for Heat Shock Proteins to Protect Hypoxia-inducible Factor 1 alpha From pVHL-independent Degradation," The Journal of Biological Chemistry 279(14):13596-13513, American Society for Biochemistry and Molecular Biology, United States (2004).
Hey, Y.Y and O'Neill, H.C., "Murine spleen contains a diversity of myeloid and dendritic cells distinct in antigen presenting function," Journal of Cellular and Molecular Medicine, 16(11):2611-2619, Wiley-Blackwell, England (Nov. 2012).
Petrylak D.P., "The Treatment of Hormone-Refractory Prostate Cancer: Docetaxel and Beyond," Reviews in Urology 8 (Suppl 2): S48-S55, United States (2006).
Shay, J.W., and Keith, W.N., "Targeting Telomerase for Cancer Therapeutics," in: British Journal of Cancer 98(4):677-683, Nature Publishing Group on behalf of Cancer Research UK (2008).
Tarantino, G., et al. "Spleen: a New Role for an Old Player?," World Journal of Gastroenterology, 17(33):3776-3784, Baishideng Publishing Group, United States (Sep. 2011).
Franciscus, A., "Hepatitis C Treatments in Current Clinical Development," retrieved from the internet :< http://mediatheque.lecrips.net/docs/pdf_ged/h03321.pdf>, retrieved on Mar. 6, 2020, 15 pages.
Godet, Y., et al., "Analysis of Spontaneous Tumor-Specific CD4 T-cell Immunity in Lung Cancer Using Promiscuous HLA-DR Telomerase-Derived Epitopes: Potential Synergistic Effect with Chemotherapy Response," Clinical Cancer Research 18(10): 29432953, American Association for Cancer Research, United States (2012).

* cited by examiner

FIG. 24
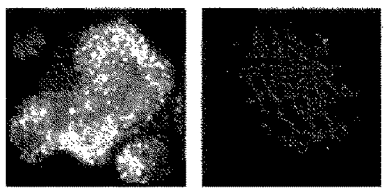
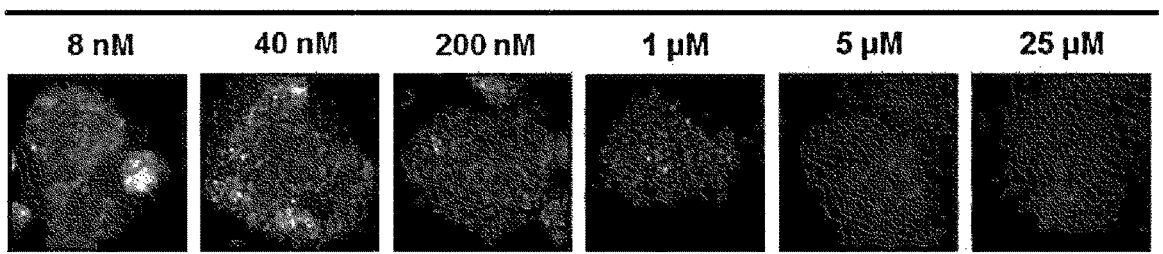
FIG. 25
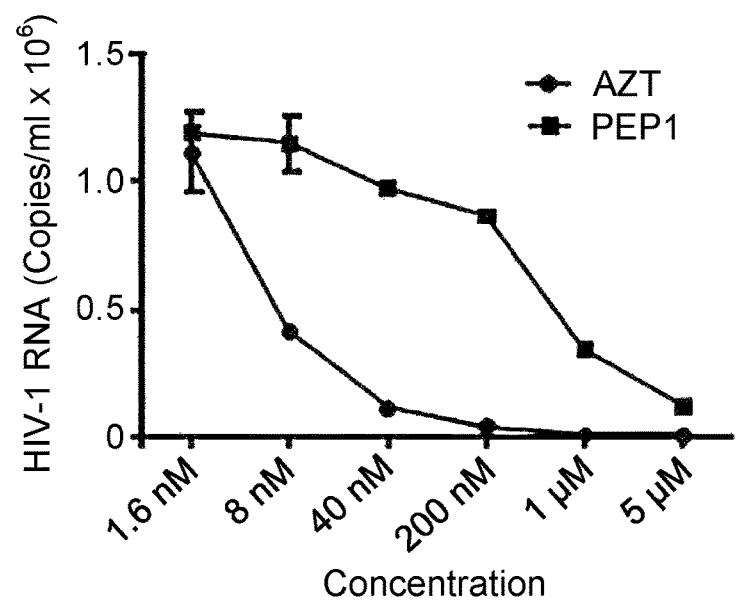

FIG. 53
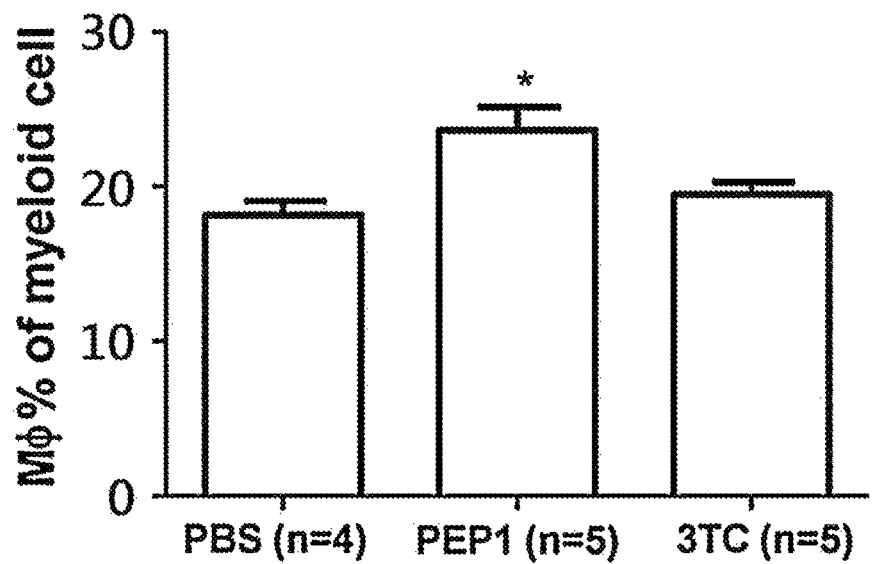
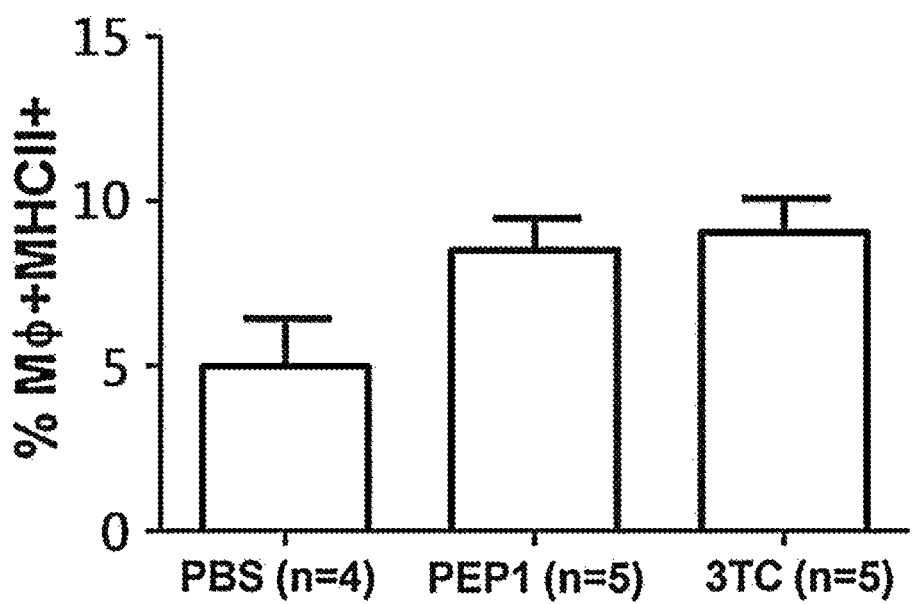

SEQUENCE LISTING

<160> NUMBER OF SEQ ID NOS: 11

<210> SEQ ID NO 1
<211> LENGTH: 16
<212> TYPE: PRT
<213> ORGANISM: Homo sapiens

<400> SEQUENCE: 1

Glu Ala Arg Pro Ala Leu Leu Thr Ser Arg Leu Arg Phe Ile Pro Lys
1               5                   10                  15

<210> SEQ ID NO 2
<211> LENGTH: 1132
<212> TYPE: PRT

<213> ORGANISM: Homo sapiens

<400> SEQUENCE: 2

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

```
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
            420                 425                 430
Gly Ser Val Ala Ala Pro Glu Glu Asp Thr Asp Pro Arg Arg Leu
        435                 440                 445
Val Gln Leu Leu Arg Gln His Ser Ser Pro Trp Gln Val Tyr Gly Phe
    450                 455                 460
Val Arg Ala Cys Leu Arg Leu Val Pro Gly Leu Trp Gly Ser
465                 470                 475                 480
Arg His Asn Glu Arg Arg Phe Leu Arg Asn Thr Lys Lys Phe Ile Ser
                485                 490                 495
Leu Gly Lys His Ala Lys Leu Ser Leu Gln Glu Leu Thr Trp Lys Met
            500                 505                 510
Ser Val Arg Asp Cys Ala Trp Leu Arg Arg Ser Pro Gly Val Gly Cys
        515                 520                 525
Val Pro Ala Ala Glu His Arg Leu Arg Glu Ile Leu Ala Lys Phe
    530                 535                 540
Leu His Trp Leu Met Ser Val Tyr Val Glu Leu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
            580                 585                 590
Leu Lys Arg Val Gln Leu Arg Glu Leu Ser Glu Ala Glu Val Arg Gln
        595                 600                 605
His Arg Glu Ala Arg Pro Ala Leu Leu Thr Ser Arg Leu Arg Phe Ile
    610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
            660                 665                 670
Pro Gly Leu Leu Gly Ala Ser Val Leu Gly Leu Asp Asp Ile His Arg
        675                 680                 685
Ala Trp Arg Thr Phe Val Leu Arg Val Arg Ala Gln Asp Pro Pro
    690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
Asn Thr Tyr Cys Val Arg Arg Tyr Ala Val Val Gln Lys Ala Ala His
            740                 745                 750
Gly His Val Arg Lys Ala Phe Lys Ser His Val Ser Thr Leu Thr Asp
        755                 760                 765
Leu Gln Pro Tyr Met Arg Gln Phe Val Ala His Leu Gln Glu Thr Ser
    770                 775                 780
Pro Leu Arg Asp Ala Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
```

```
                  820                 825                 830
Gln Gly Ser Ile Leu Ser Thr Leu Leu Cys Ser Leu Cys Tyr Gly Asp
            835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
            885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
            930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
            965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
            995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 3
<211> LENGTH: 20
<212> TYPE: DNA
<213> ORGANISM: Artificial Sequence
<220> FEATURE:
<223> OTHER INFORMATION: Forward primer

<400> SEQUENCE: 3
cgaccagtac caccatcctt                                                 20

<210> SEQ ID NO 4
<211> LENGTH: 20
<212> TYPE: DNA
<213> ORGANISM: Artificial Sequence
```

-continued

```
<220> FEATURE:
<223> OTHER INFORMATION: Reverse primer

<400> SEQUENCE: 4
agcaccttac ccaggcctat                                              20

<210> SEQ ID NO 5
<211> LENGTH: 27
<212> TYPE: DNA
<213> ORGANISM: Artificial Sequence
<220> FEATURE:
<223> OTHER INFORMATION: Sense primer

<400> SEQUENCE: 5
tgctatgtca gttccccttg gttctct                                      27

<210> SEQ ID NO 6
<211> LENGTH: 30
<212> TYPE: DNA
<213> ORGANISM: Artificial Sequence
<220> FEATURE:
<223> OTHER INFORMATION: Anti-sense primer

<400> SEQUENCE: 6
agttggagga catcaagcag ccatgcaaat                                   30

<210> SEQ ID NO 7
<211> LENGTH: 20
<212> TYPE: DNA
<213> ORGANISM: Artificial Sequence
<220> FEATURE:
<223> OTHER INFORMATION: Sense primer

<400> SEQUENCE: 7
aatcccatca ccatcttcca                                              20

<210> SEQ ID NO 8
<211> LENGTH: 20
<212> TYPE: DNA
<213> ORGANISM: Artificial Sequence
<220> FEATURE:
<223> OTHER INFORMATION: Anti-sense primer

<400> SEQUENCE: 8
tggactccac gacgtactca                                              20

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
ttgacaagaa tcctcacaat acc                                          23

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ggaggttggg gactgcgaat                                              20
```

```
<210> SEQ ID NO 11
<211> LENGTH: 16
<212> TYPE: PRT
<213> ORGANISM: Artificial Sequence
<220> FEATURE:
<223> OTHER INFORMATION: Modified SEQ ID 1
<220> FEATURE:
<221> NAME/KEY: MISC_FEATURE
<222> LOCATION: (1)..(1)
<223> OTHER INFORMATION: NH2-Glu(OtBu)
<220> FEATURE:
<221> NAME/KEY: MISC_FEATURE
<222> LOCATION: (3)..(3)
<223> OTHER INFORMATION: Arg(Pbf)
<220> FEATURE:
<221> NAME/KEY: MISC_FEATURE
<222> LOCATION: (8)..(8)
<223> OTHER INFORMATION: Thr(tBu)
<220> FEATURE:
<221> NAME/KEY: MISC_FEATURE
<222> LOCATION: (9)..(9)
<223> OTHER INFORMATION: Ser(tBu)
<220> FEATURE:
<221> NAME/KEY: MISC_FEATURE
<222> LOCATION: (10)..(11)
<223> OTHER INFORMATION: Arg(Pbf)Leu
<220> FEATURE:
<221> NAME/KEY: MISC_FEATURE
<222> LOCATION: (12)..(12)
<223> OTHER INFORMATION: Arg(Pbf)
<220> FEATURE:
<221> NAME/KEY: MISC_FEATURE
<222> LOCATION: (16)..(16)
<223> OTHER INFORMATION: Lys(Boc)-2-chloro-Trityl Resin

<400> SEQUENCE: 11

Glu Ala Arg Pro Ala Leu Leu Thr Ser Arg Leu Arg Phe Ile Pro Lys
1               5                   10                  15
```

PEPTIDE HAVING ANTI-VIRAL EFFECT AND COMPOSITION CONTAINING SAME

CROSS-REFERENCE TO RELATED APPLICATIONS

This application is the U.S. national phase of PCT/KR2016/007192, filed Jul. 4, 2016, which claims foreign priority to KR 10-2015-0094840, filed Jul. 2, 2015, and KR 10-2015-0115671, filed Aug. 17, 2015.

REFERENCE TO SEQUENCE LISTING SUBMITTED ELECTRONICALLY VIA EFS-WEB

The content of the electronically submitted sequence listing (Name: 2473_1010002_ST25; 11,8d2 bytes, 12,565 bytes; and Date of Creation: Oct. 2, 2018) filed on Oct. 5, 2018 is incorporated herein by reference in its entirety.

TECHNICAL FIELD

The specification relates to a peptide having an antiviral activity and a composition comprising the same, and more particularly, to a composition for preventing and treating a viral disease, which comprises a peptide derived from telomerase, and is effective in treating a viral disease by inhibiting self replication and activity of a virus.

BACKGROUND ART

Anti-viral activity may be divided into directly recognizing and attacking a viral protein or a part thereof, inhibiting each phase of the life cycle of a virus, or enhancing immunity. The method of inhibiting each phase of the life cycle of a virus may vary depending on a phase. For example, as a viral agent for inhibiting the phase before entry into host cells, an entry-inhibitor or entry-blocking agent, which disturbs the viral entry into cells, or an agent for blocking viral penetration and uncoating is able to be used. In addition, there is an antiviral activity in the phase of viral replication in host cells after the viral entry into host cells, which is to inhibit viral replication via a nucleotide or nucleoside analogue that is similar to a building block of viral RNA or DNA but inactivates a RNA or DNA polymerase. Representatively, a reverse transcriptase inhibitor may be used in this phase. A subsequent phase is to inhibit an integrase for cutting synthesized viral DNA, viral transcription, translation, post-translational modification, or subsequent targeting. Other than these, inhibition of a viral protease, blockage of viral assembly, or blockage of the final phase which is a release phase of viruses from host cells may be used. For the antiviral activity, a drug for relieving various symptoms caused by a virus, not directly acting on a virus as described above, can also be used. For example, while an antiphlogistic for reducing inflammation caused by a virus or an antipyretic for reducing a high fever caused by a virus can be used, it may not be considered as a fundamental therapeutic agent against a virus.

A virus is an infectious pathogen with a smaller size than a bacterium. The virus is composed of a genetic material such as RNA or DNA and a protein surrounding the genetic material. Since viruses do not have own metabolism, they allow DNA or RNA to penetrate into host cells, replicate their own genetic materials using organelles of the penetrated cells, and produce viruses resembling themselves. In this procedure, host cells are damaged or disrupted, inducing a disease in a host.

Hepatitis C virus (hereinafter, referred to as HCV) is a positive sense single-stranded RNA virus, which was first identified in 1989, belongs to Flaviviridae, and has a genome size of approximately 9.5 kb. In the early infection, there is no symptom, and approximately 55 to 85% of patients develop chronic hepatitis, and among them, approximately 5 to 10% of patients develop hepatic cirrhosis and then progress to liver cancer.

HCV is broadly classified into 6 types of genotypes according to the difference in the base sequence of its genome, and their clinical differences such as responses to treatments have been reported. Depending on a region, differences in the distribution of HCV genotypes have been noted, and there are some reports that the typical types in Korea are types-1b and 2a. However, there is insufficient data to support this. After infection, due to a higher mutation rate than other viruses, HCV has six different strands and produces numerous quasi-species in a single strand. Because of this characteristic, HCV is expected to have a resistance to a single therapeutic agent, and thus requires combined therapy using various therapeutic agents. Therefore, there is an immediate need to develop more stable and effective research and therapeutic agents, which can prevent and treat a liver disease caused by HCV.

HCV produces one fusion protein comprising 3,030 amino acids using its own genome as a substrate after viral infection. Particularly, it has been noted that a 5'-untranslated region (UTR) and a 3'-UTR play very critical roles in HCV replication. The 5'-UTR has an internal ribosome entry site (IRES) that is highly conserved in the HCV strand, and thus has cap-independent translation. The fusion protein first produced after the infection is processed by host and viral proteases, resulting in structural proteins such as C, E1, E2, etc. and regulatory proteins required in viral replication such as NS2, NS3, NS4A, NS4B, NS5A, NS5B, etc.

As anti-HCV agents, inhibitors mainly targeting HCV, which have been actively developed until now, are NS3 protease and NS5B polymerase. The result of a phase 1 clinical trial for a drug targeting such a virus-specific enzyme such as NS3 protease, conducted by Boehringer-Ingelheim in 2003, has been reported to the journal Nature and noted. However, NS3 is difficult to be designed as a drug based on a basic structure because it has difficulty in drug penetration due to its structure, whereas NS5B has a typical polymerase structure, which is a thumb-palm-finger shape, and is known to have possibilities in the design of a non-nucleoside inhibitor, as well as an active region. In recent years, a therapeutic agent targeting HCV, not a host, is being developed.

In addition, hepatitis B virus (hereinafter, referred to as HBV) infection broadly shows a variety of clinical progressions toward symptomless infection, chronic infection, hepatic cirrhosis and hepatocellular carcinoma (HCC), and increases chronic disease morbidity and mortality. As approximately 350 million HBV carriers are found around the globe, HBV-derived liver diseases threaten human health, and HBV, accounting for 53% of the total cases of HCC, is one of the major factors triggering HCC as well as HCV and other cases.

HBV produces three types of envelope proteins, which are all encoded in a pre-S/S open reading frame. While the role of large surface proteins (LHBs) of HBV has not been clearly identified, it has been suggested that LHBs are involved in viral assembly and attachment to liver cells.

According to a variety of studies, LHBs with a mutation in a preS region bring about a change in transactivation or induce a reticulum stress pathway, implying the contribution to the occurrence of liver cancer.

As conventional standard liver cancer and antiviral therapies, when there is no hepatic cirrhosis or a sufficient remaining liver function, hepatectomy is primarily considered, and when dyshepatia is accompanied, liver transplantation is considered as a primary therapy, but it may be difficult to be applied to most HCC patients due to portal hypertension, liver failure, multiple tumors, an invasive context, an old age, etc. As a non-operative therapy, radiofrequency thermal ablation and ethanol injection are mostly used, but when a tumor size is large, they have low success rates.

As described above, since treatment of HCC mostly depends on a surgical operation, thermal therapy, etc., and the treatment rate of chemotherapy is very low, there is an immediate need to develop an alternative drug. In Korea, particularly, due to the prevalence of HBV-derived HCC, a pre-emptive treatment for chronic hepatitis B is required, and in the case of HCC accompanied by hepatitis B, a success rate in liver cancer treatment is increased with pre-emptive or simultaneous treatment for hepatitis. Particularly, when HCC is caused by chronic hepatitis and liver cirrhosis, even after the HCC treatment, its recurrence is very high, and such treatment for chronic inflammation has to be simultaneously performed, therapeutic strategies for chronic hepatitis and HCC, which are specialized for the development and progression of liver cancer caused by HBV genotype C exclusively present in Korea are required. Accordingly, previously, interferon and lamivudine have been used as antiviral agents to treat chronic hepatitis B, but they have side effects and low reactivity. In a recent year, adefovir, tenofovir, etc. have been developed and used as drugs for inhibiting virus proliferation to delay liver damage. While such drugs have the effect of inhibiting virus proliferation and delaying liver damage, they may not remove viruses completely or treat hepatitis. Therefore, continuous prescription is needed by which resistance appears, and hepatotoxicity and nephrotoxicity are exhibited due to the nature of the drugs. In recent years, since a clinically-available, unique liver cancer-targeting agent such as sorafenib has a limited treatment range and close monitoring of treatment progression is required, research on the development of a new liver cancer-targeting agent is progressing all over the world. The majority of developing substances are kinase inhibitors derived from a multiple kinase inhibitor such as sorafenib, or angiogenic inhibitors that inhibit angiogenesis necessary for liver cancer progression. No significant result was obtained from the results of a phase 2 clinical trial for an epidermal growth factor receptor inhibitor known to be overexpressed in 66% of HCC patients. A low molecular weight tyrosine kinase inhibitor developed for angiogenic inhibition, such as brivanib, and a monoclonal antibody such as ramucirumab did not obtain good results in phase 2 clinical trials. As abnormalities in an mTOR signaling system have been reported in 40 to 50% of the HCC patients, a phase 3 clinical trial for mTOR inhibitors including everolimus in sorafenib non-responsive patients was launched, but significant effects were not demonstrated, compared to a placebo. As a new therapeutic strategy, the development of HCC therapeutic agents using c-MET, MEK inhibitory low molecular weight materials is also being attempted.

Most new therapeutic materials, now in development, have entered into the initial phase of clinical trials, and drugs whose clinical trials are almost finished cannot be used as primary drugs, and exhibit significant effects only when used in combination with conventional sorafenib. Therefore, the development of a new drug which works with a different mechanism from the conventional drugs in development, has significant effects in liver cancer patients, and inhibits the progression of hepatitis is expected to revolutionize the treatment of related liver diseases.

Among the conventional drugs, most of the anticancer agents have failed to exhibit HCC treatment effects in systemic anticancer therapy, and sorafenib only exhibits an effect of prolonged survival time of approximately two months. This sorafenib is not even considered as primary treatment. Therefore, the development of HCC-specialized anticancer agents that replace conventional products and can be used for therapy-resistant patients is required.

Meanwhile, a human immunodeficiency virus (hereinafter, referred to as HIV) is a virus which is a member of the family Retroviridae and the genus *Lentivirus*. The *Lentivirus* may infect various living species, and is a causative agent inducing a chronic disease with a long incubation period.

The life cycle of HIV may broadly consist of invasion of host cells, replication and transcription in the cells, recombination of viral genomes, and finally synthesis of the viruses and secretion out of the cells. The HIV is able to be inhibited by blocking any one step of the above-described procedure of HIV proliferation.

The drugs that have been recently developed as therapeutic agents and used in patients consist of fusion inhibitors, reverse transcriptase inhibitors converting RNA into DNA, and protease inhibitors which are drugs blocking a process of digesting a protein by a protease.

The goal of anti-HIV treatment is to recover a patient's immune system by strongly inhibiting HIV to make HIV in a non-proliferated state and maintaining this state as long as possible, and to reduce morbidity and mortality due to HIV infection. However, when the anti-HIV treatment is interrupted, HIV appears again, and the immunity is also decreased. For this reason, once the treatment is started, it cannot be stopped in the middle, which is the limit in anti-HIV treatment that is currently used. This means that the problem that anti-HIV treatment should continue for at least several years, and unless a curative method is developed, for several decades, causing a patient has to bear an economic burden and side effects that come with long-term administration of a drug, and particularly, it should be considered that the drug may have side effects that will be gradually revealed with the increasing period of its use, as well as the currently-known side effects. The current anti-HIV drugs may also have a major problem in which HIV acquires drug resistance and thus is difficult to treat because of the difficulty in properly taking the drugs for a long time. Therefore, it is necessary to develop a novel therapeutic agent that can overcome several disadvantages of the conventional therapeutic agents, exhibit an inhibitory effect on HIV itself, and enhance the activity of immune cells.

SUMMARY OF THE INVENTION

Technical Problem

The present invention is directed to providing an antiviral composition for preventing and treating a viral disease, which is effective and has no side effects.

Technical Solution

According to an aspect, the present invention provides an antiviral composition, which includes one or more selected from the group consisting of a peptide comprising an amino acid sequence of SEQ ID NO:1, a peptide having at least 80% sequence homology with the amino acid sequence, and a fragment thereof.

In the composition according to one aspect of the present invention, the fragment may be a fragment composed of at least three amino acids.

In the composition according to one aspect of the present invention, the composition may inhibit a target virus by inhibiting viral replication.

In the composition according to one aspect of the present invention, the viral replication may be mediated by HSP90.

In the composition according to one aspect of the present invention, the virus may be HCV, HBV or HIV.

According to another aspect, the present invention provides a method for preventing and treating a viral disease, which comprises administering a pharmaceutically effective amount of the composition according to the present invention into a subject having contracted a viral disease or having pathological symptoms.

According to still another aspect, the present invention provides a kit for preventing and treating a viral disease, which comprises instructions in which a method for preventing and treating a viral disease is described.

According to yet another aspect, the present invention provides a use of a peptide comprising an amino acid sequence of SEQ ID NO:1, a peptide having at least 80% sequence homology with the amino acid sequence or a fragment thereof to prepare an antiviral composition.

In the use to prepare an antiviral composition according to an aspect of the present invention, the composition may inhibit a target virus by inhibiting RNA replication of the virus.

In the use to prepare an antiviral composition according to an aspect of the present invention, the virus may be HCV, HBV or HIV.

According to yet another aspect, the present invention provides a use of a peptide comprising an amino acid sequence of SEQ ID NO:1, a peptide having at least 80% sequence homology with the amino acid sequence or a fragment thereof to prepare a pharmaceutical composition for preventing and treating a viral disease.

In the use to prepare a composition for preventing and treating a viral disease according to an aspect of the present invention, the composition may inhibit a target virus by inhibiting RNA replication of the virus.

In the use for preparing a composition for preventing and treating a viral disease according to an aspect of the present invention, the virus may be HCV, HBV or HIV.

Advantageous Effects

Since a peptide comprising an amino acid sequence of SEQ ID NO:1, a peptide having at least 80% sequence homology with the amino acid sequence, and a fragment thereof according to an aspect of the present invention has an anti-virus inhibiting effect, a method for treating or preventing a viral disease is provided.

DETAILED DESCRIPTION OF DRAWINGS

Figure 9:
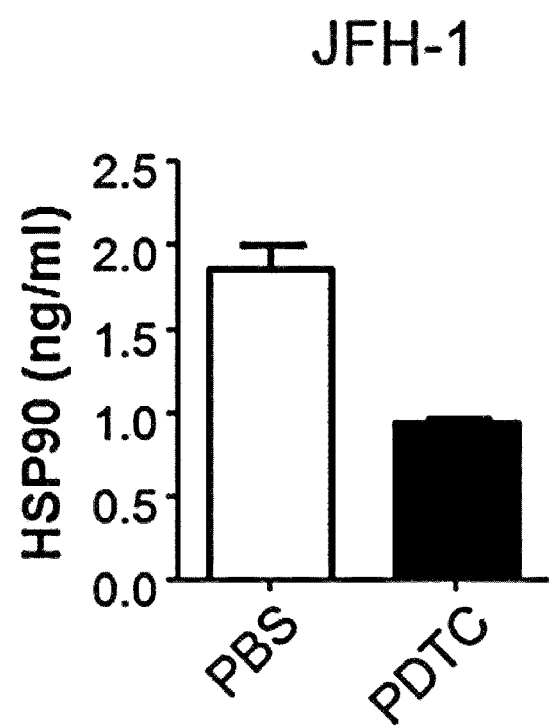

FIG. 9 is a graph showing expression levels (ng/ml) of HSP90 when a JFH-1 cell line is treated with an antioxidant PDTC, compared to treatment with a control group (PBS) through ELISA (The error bar represents a standard error of the mean (SEM). Compared with a vehicle control, *P<0.05 and **P<0.01. The P values are obtained based on a two-tailed Student's t-test for independent samples, and are the representative values obtained from two to five independent experiments).

Figure 10:
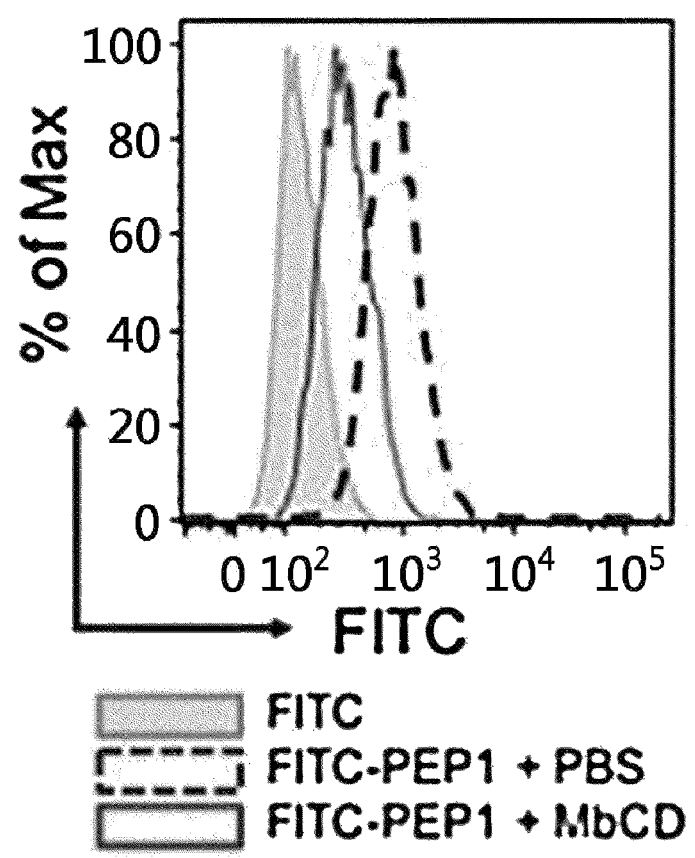

FIG. 10 is a graph showing the result of flow cytometry for cells of a JHF-1 cell line incubated with fluorescein isothiocyanate (FITC)-conjugated PEP1 (FITC-PEP1) for 2 hours, and then with MbCD (5 mM), and the result is the representative value obtained from three independent experiments.

Figure 11:
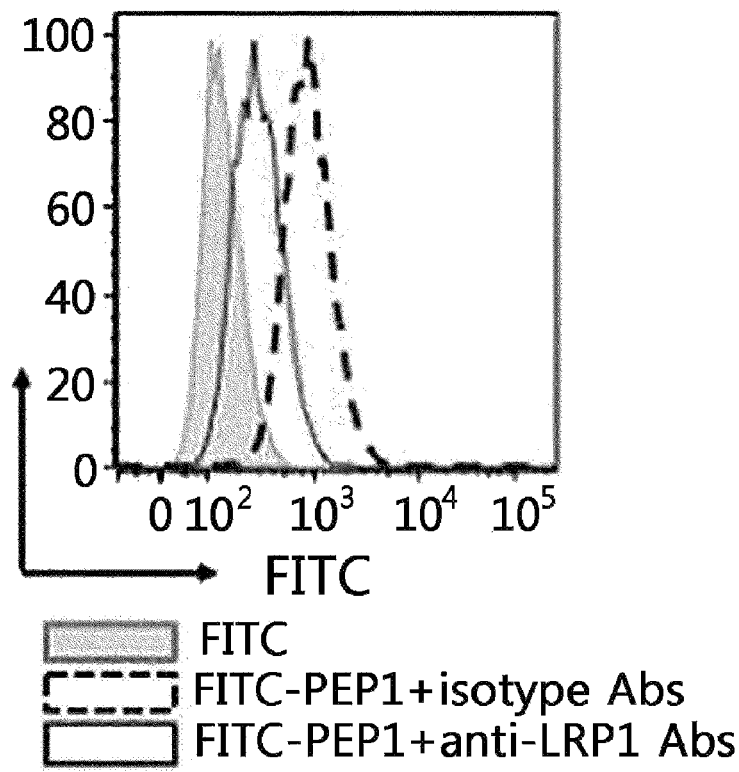

FIG. 11 is a graph showing the result of flow cytometry for cells of a JHF-1 cell line incubated with FITC-conjugated PEP1 (FITC-PEP1) for 2 hours, and then with anti-LRP1 antibodies, and the result is the representative value obtained from three independent experiments.

Figure 12:
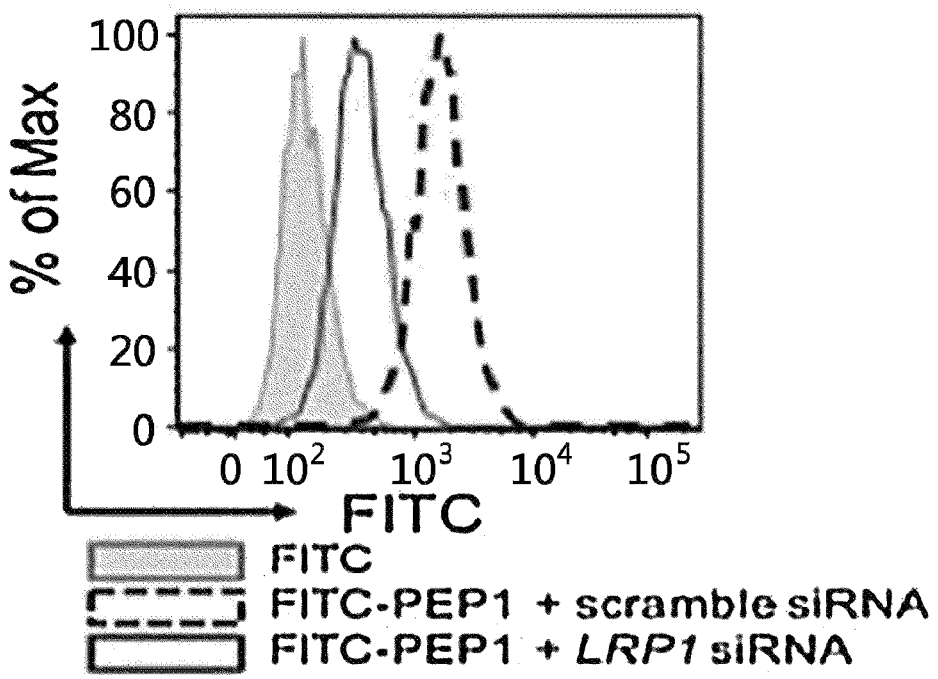

FIG. 12 is a graph showing the result of flow cytometry for cells of a JHF-1 cell line incubated with FITC-conjugated PEP1 (FITC-PEP1) for 2 hours, and then with LRP1 siRNA (200 nM), and the result is the representative value obtained from three independent experiments.

Figure 13:
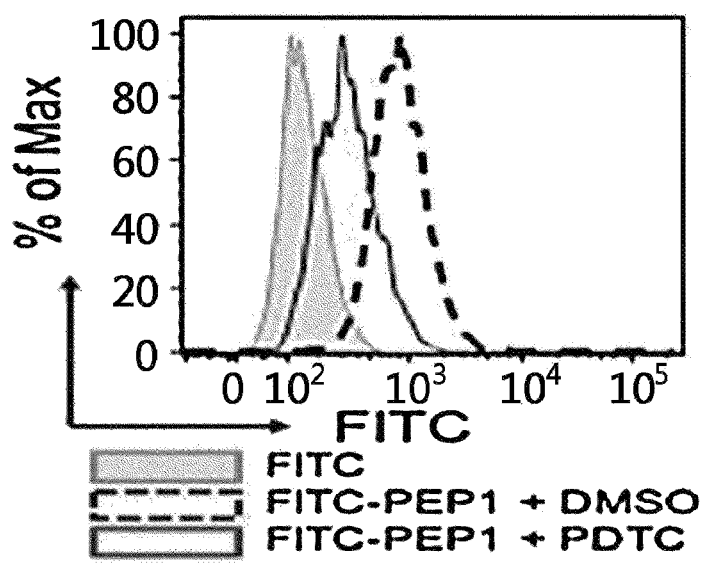

FIG. 13 is a graph showing the result of flow cytometry for cells of a JHF-1 cell line incubated with FITC-conjugated PEP1 (FITC-PEP1) for 2 hours, and then with PDTC, and the result is the representative value obtained from three independent experiments.

Figure 14:
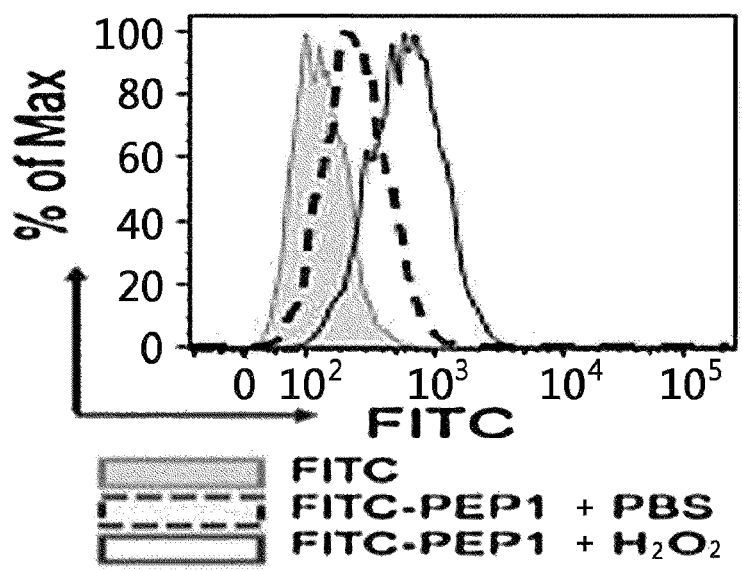

FIG. 14 is a graph showing the result of flow cytometry for cells of a JHF-1 cell line incubated with FITC-conjugated PEP1 (FITC-PEP1) for 2 hours, and then with $H_2O_2$, and the result is the representative value obtained from three independent experiments.

Figure 15:
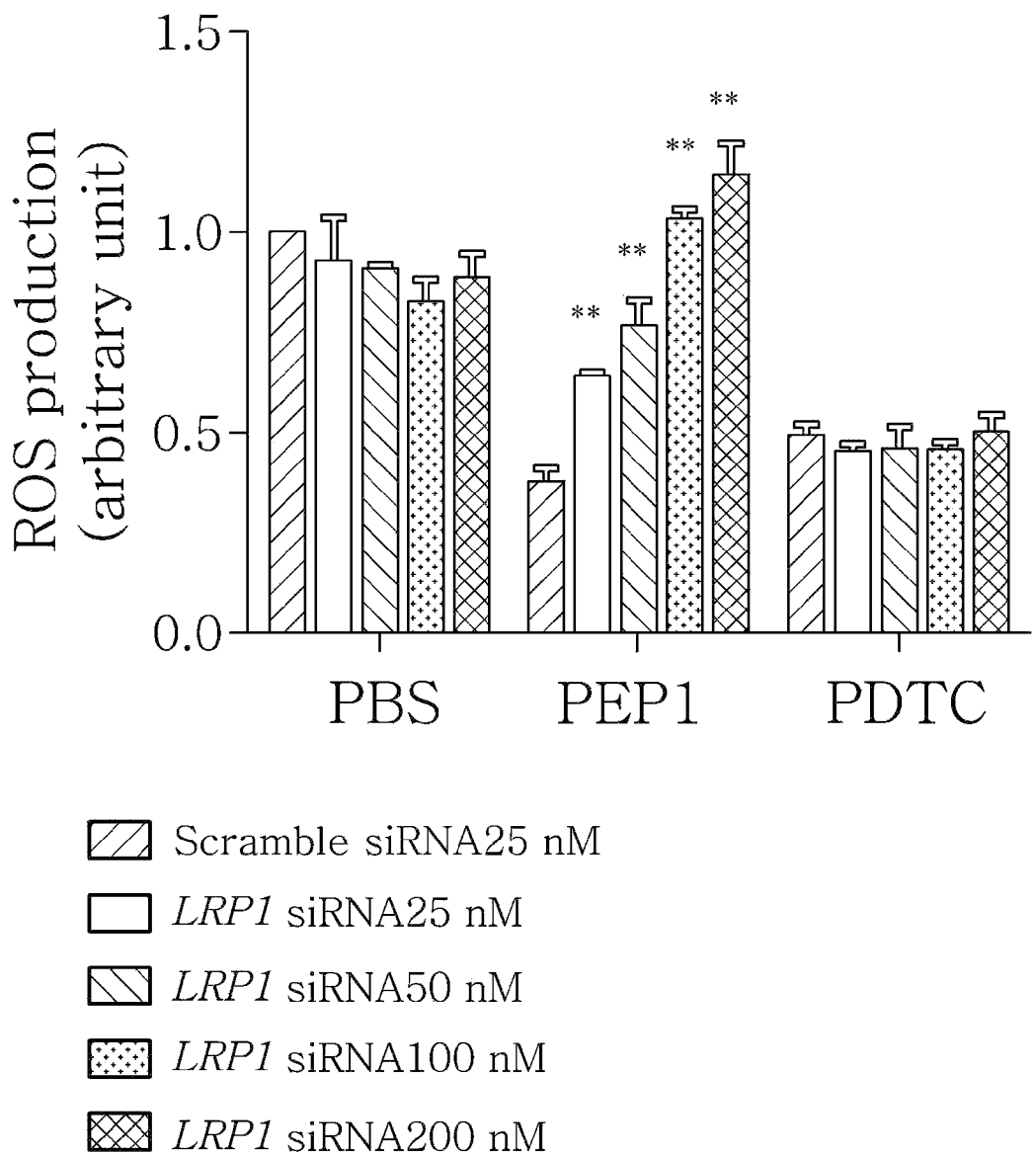

FIG. 15 is a graph showing the ROS production measured using a DCF-DA method after a JFH-1 cell line is treated with PEP1 (10 μM), PDTC (100 μM) or PBS for two hours, and transfected with scramble siRNA or LRP1 siRNA (The error bar indicates SEM. Compared to a scrambled control, **P<0.01, the P value is obtained based on a two-tailed Student's t-test for independent samples, and is the representative value obtained from three independent experiments).

Figure 16:
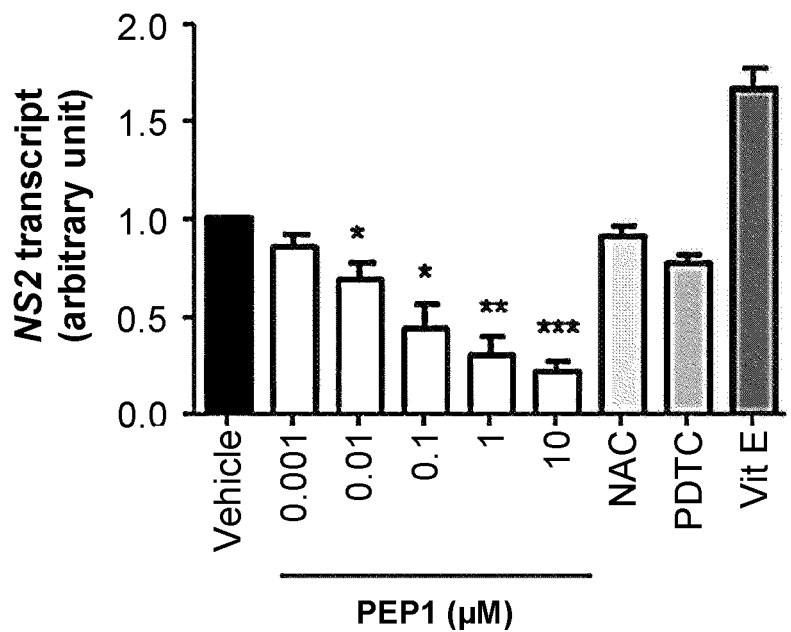

FIG. 16 shows the in vitro anti-HCV activity of PEP1, measured by quantitative PCR for an NS2 transcript of HCV when a JFH-1 cell line is cultured with PEP1, NAC (20 mM), PDTC (100 μM) and vitamin E (10 μM) for 48 hours.

Figure 17:
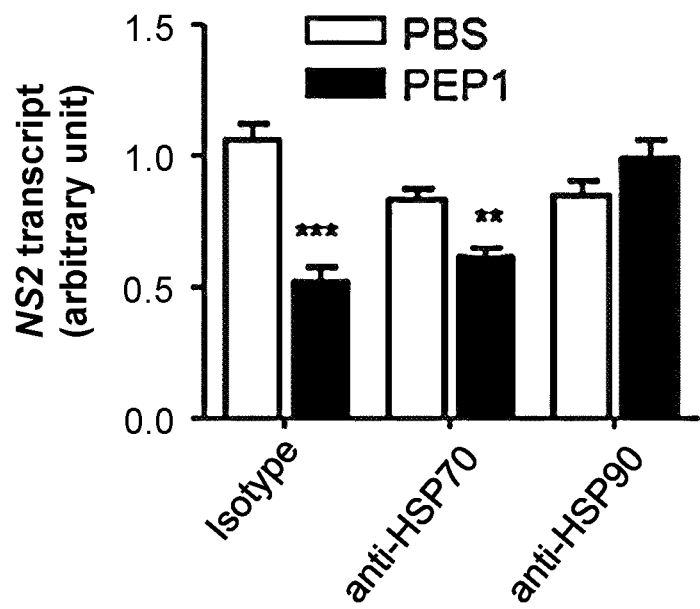

FIG. 17 shows the NS2 transcript in a JFH-1 cell line, measured after incubation with anti-HSP70 antibodies, anti-HSP90 antibodies, or control (isotype) antibodies for 2 hours in the presence of PEP1 (10 μM).

Figure 18:
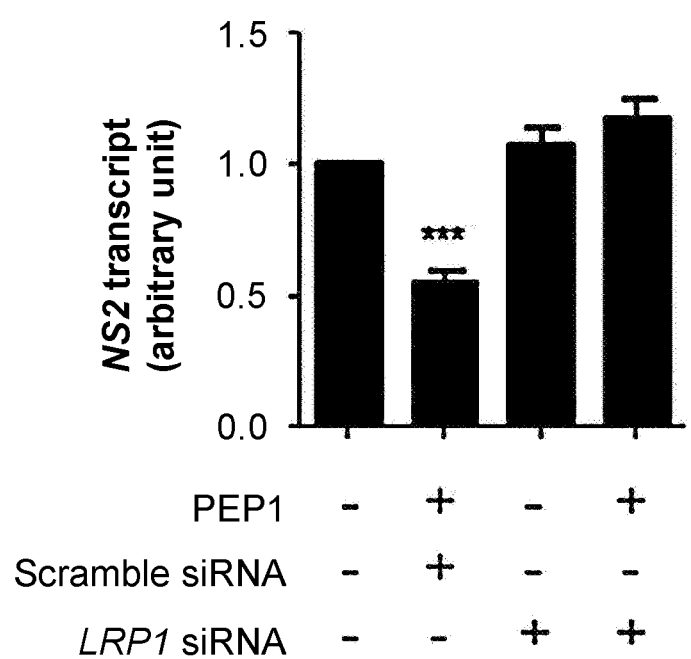

FIG. 18 shows the result obtained when a JFH-1 cell line is transfected with scramble siRNA or LRP1 siRNA for 18 hours, and treated with PEP1 (10 μM) or PBS for two hours (The error bar indicates SEM. Compared to a vehicle or a PBS control, *P<0.05, P<0.01, and *P<0.001. The P values are obtained based on a two-tailed Student's t-test for independent samples, and are the representative values are obtained from three or four independent experiments).

Figure 19:
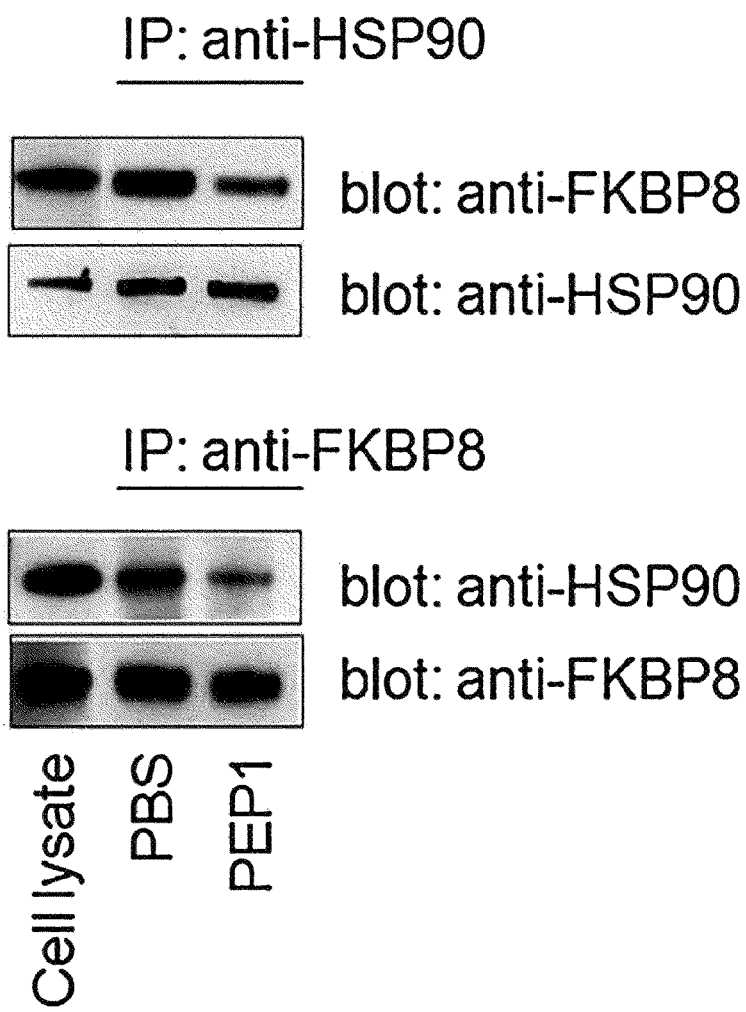

FIG. 19 shows that, in a JFH-1 cell line, PEP1 inhibits an interaction between FKBP8 involved in replication of HCV RNA and HSP90 binding thereto (the result is the representative value obtained from two independent experiments).

Figure 20:
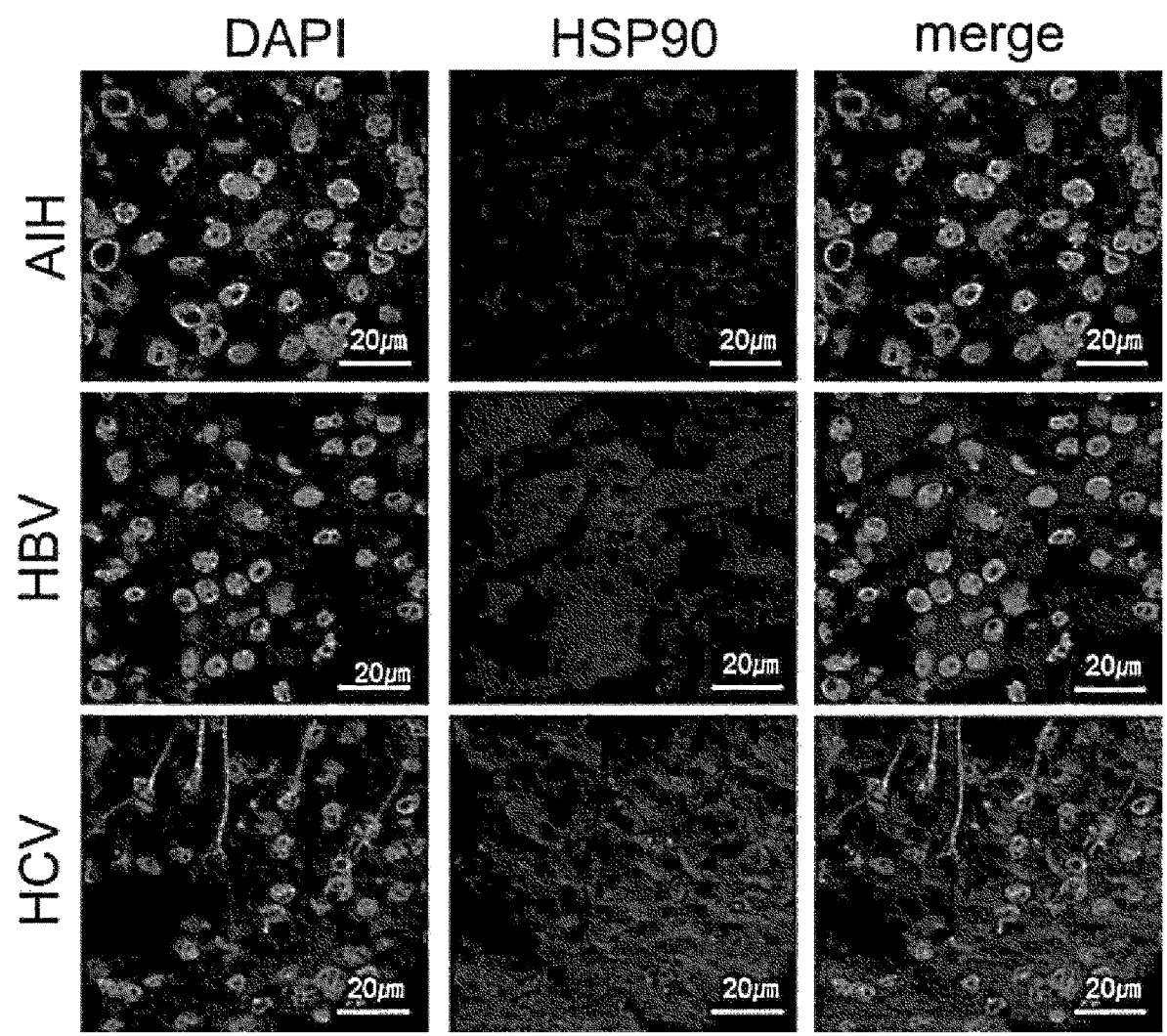

FIG. 20 shows liver tissue of a chronic HCV-infected patient, stained with HSP90 (red) by immunohistochemistry, in which a nucleus is counterstained with DAPI (blue), and liver tissue obtained from an autoimmune hepatitis (AIH) patient or hepatitis B patient is used as a control.

Figure 21:
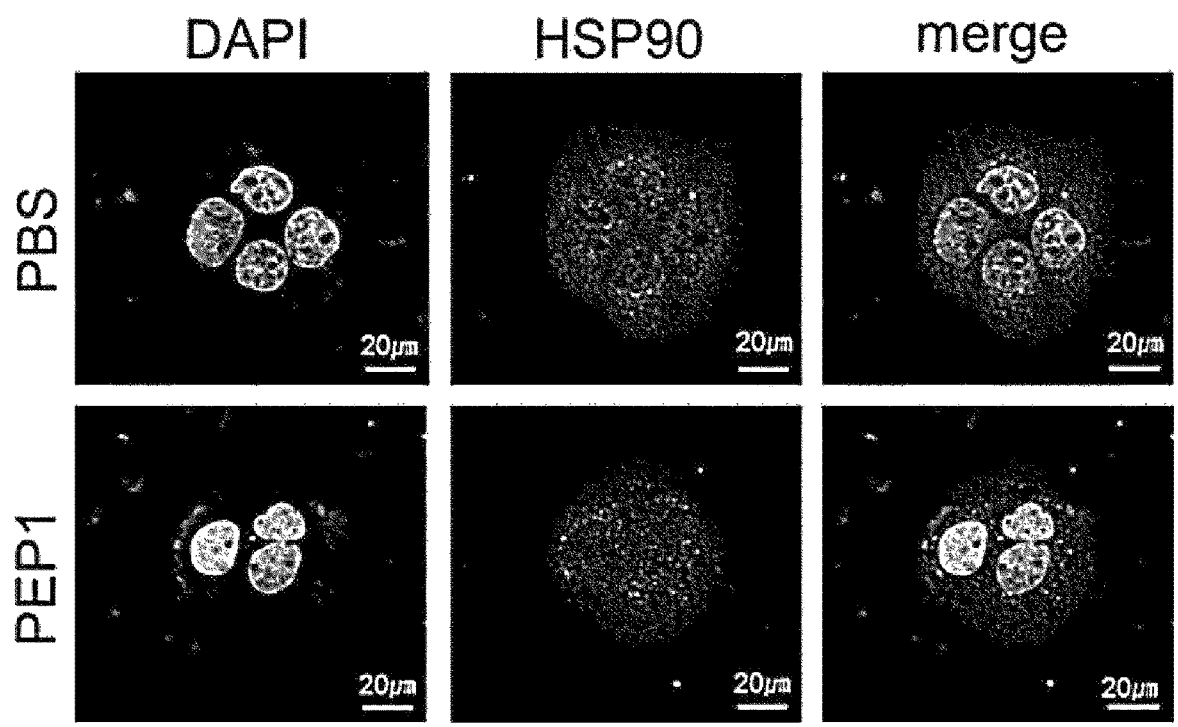

FIG. 21 shows JFH-1 cells immunostained with HSP90, after incubation with PEP1 (10 μM) or PBS for 2 hours, and the result is the representative value obtained from two independent experiments.

Figure 22:
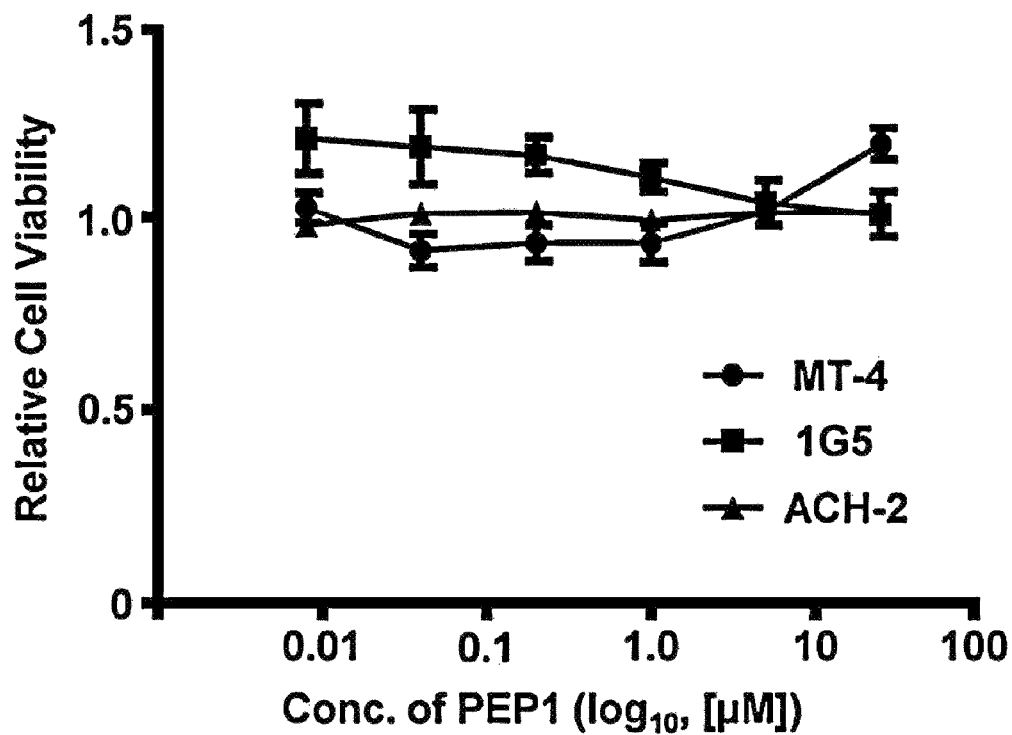

FIG. 22 shows an effect of PEP1 on cell viability, which is assessed by treating MT-4, IG5 and ACH-2 cells with increasing PEP1 concentrations for 5 days, and performing an MTT assay.

Figure 23:
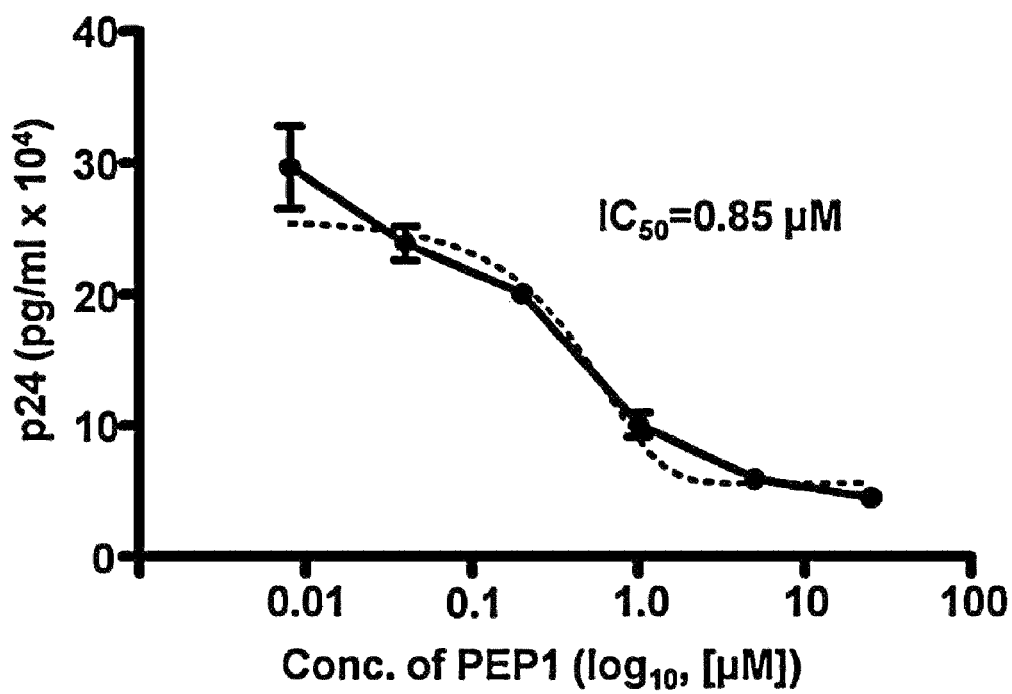

FIG. 23 shows an effect of PEP1 on production of HIV-1 viruses, which is obtained by treating HIV-1-infected MT-4 cells with increasing concentrations of PEP1 (the amount of viral particles in the supernatant is measured by p24 ELISA).

FIG. 24 shows an effect of PEP1 on eGFP expression (eGFP is expressed like HIV-1 Nef) monitored using a fluorescence microscope, after HIV-4-infected MT-4 cells are treated with increasing concentrations of PEP1.

FIG. 25 shows inhibition of production of HIV-1 viral particles, which is analyzed by measuring a level of viral genomes in the supernatant by RT-qPCR after HIV-1-infected MT-4 cells are treated with AZT or PEP1 at concentrations increased stepwise.

Figure 26:
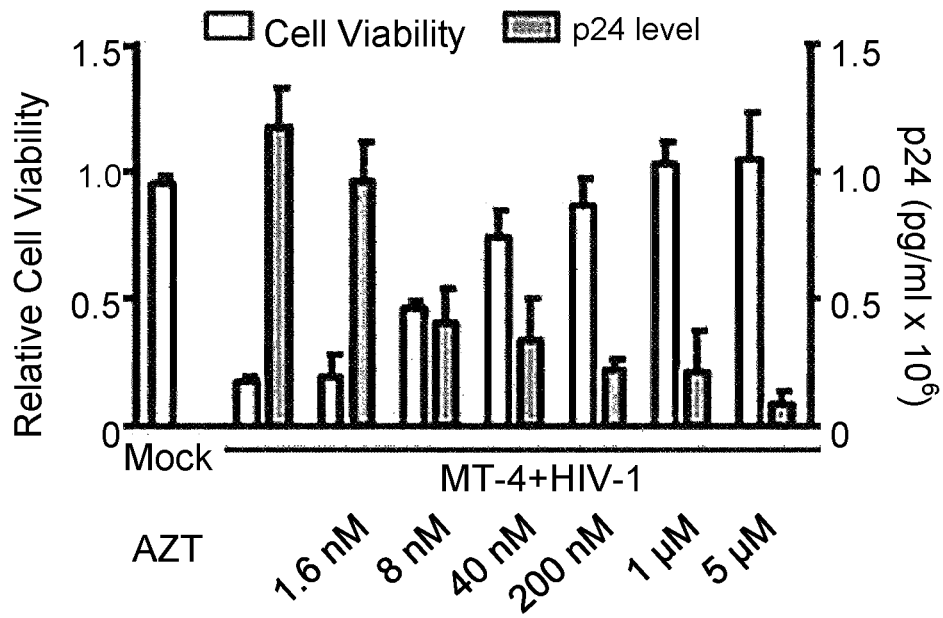

FIG. 26 shows a cell protective effect of PEP1 from HIV-1 infection-associated cell death, analyzed by evaluating cell viability through p24 ELISA after MT-4 cells ($1\times10^4$) are infected with HIV-1 viruses ($4\times10^5$ $CCID_{50}$) and treated with AZT for 5 days (Data is expressed as means±standard deviation (SD)).

Figure 27:
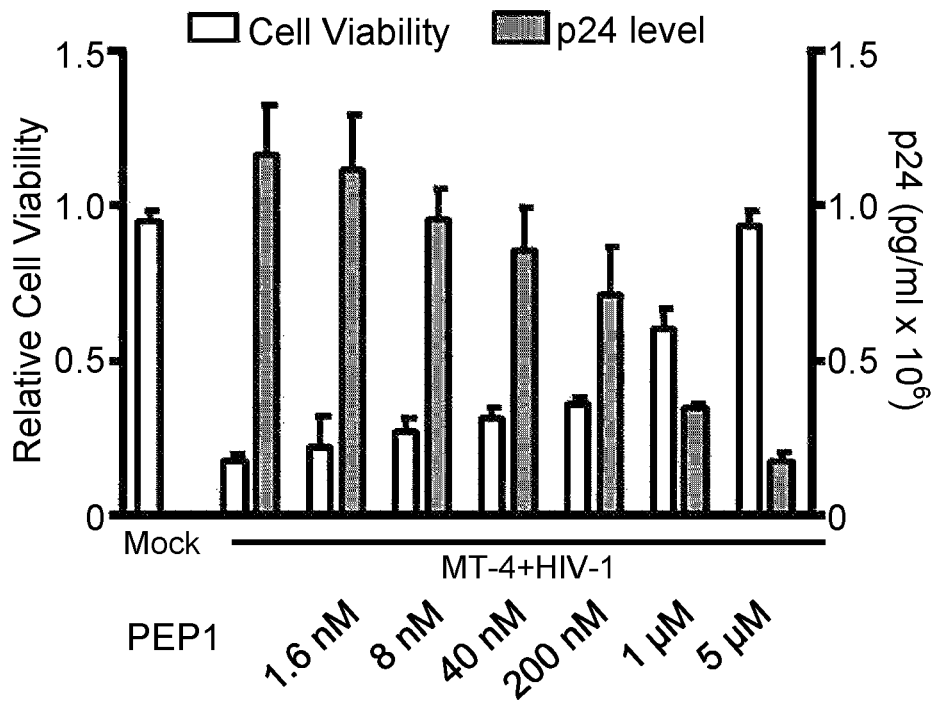

FIG. 27 shows a cell protective effect of PEP1 from HIV-1 infection-associated cell death, analyzed by evaluating cell viability through p24 ELISA after MT-4 cells ($1\times10^4$) are infected with HIV-1 viruses ($4\times10^5$ $CCID_{50}$) and treated with PEP1 for 5 days (The data is expressed as means±SD).

Figure 28:
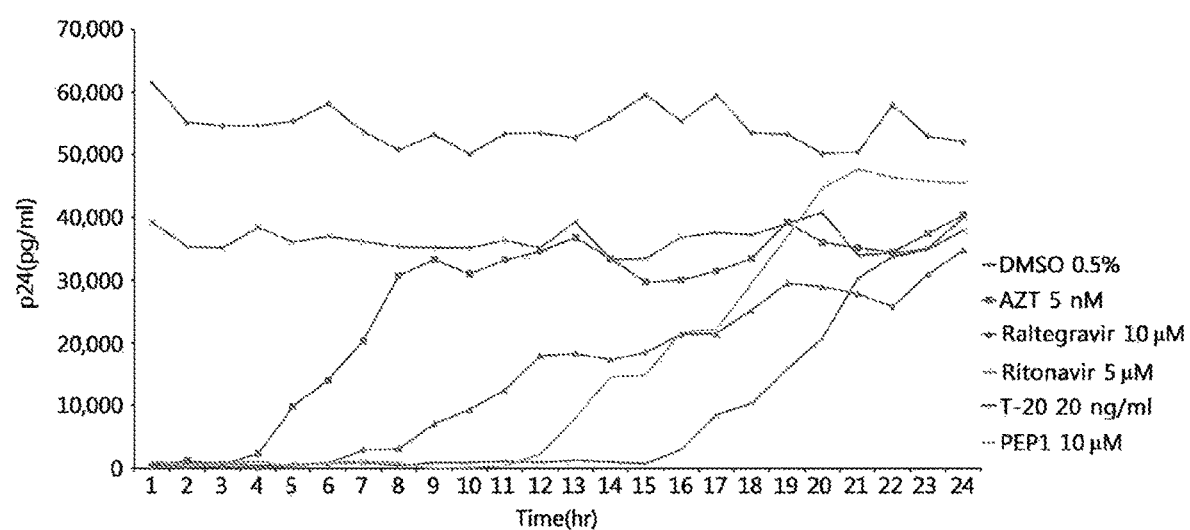

FIG. 28 shows the result of a time-of-addition assay for evaluating HIV-1 replication through p24 ELISA five days after MT-4 cells are infected with HIV-1 and treated with designated anti-HIV-1 drugs containing PEP1 at different time points.

Figure 29:
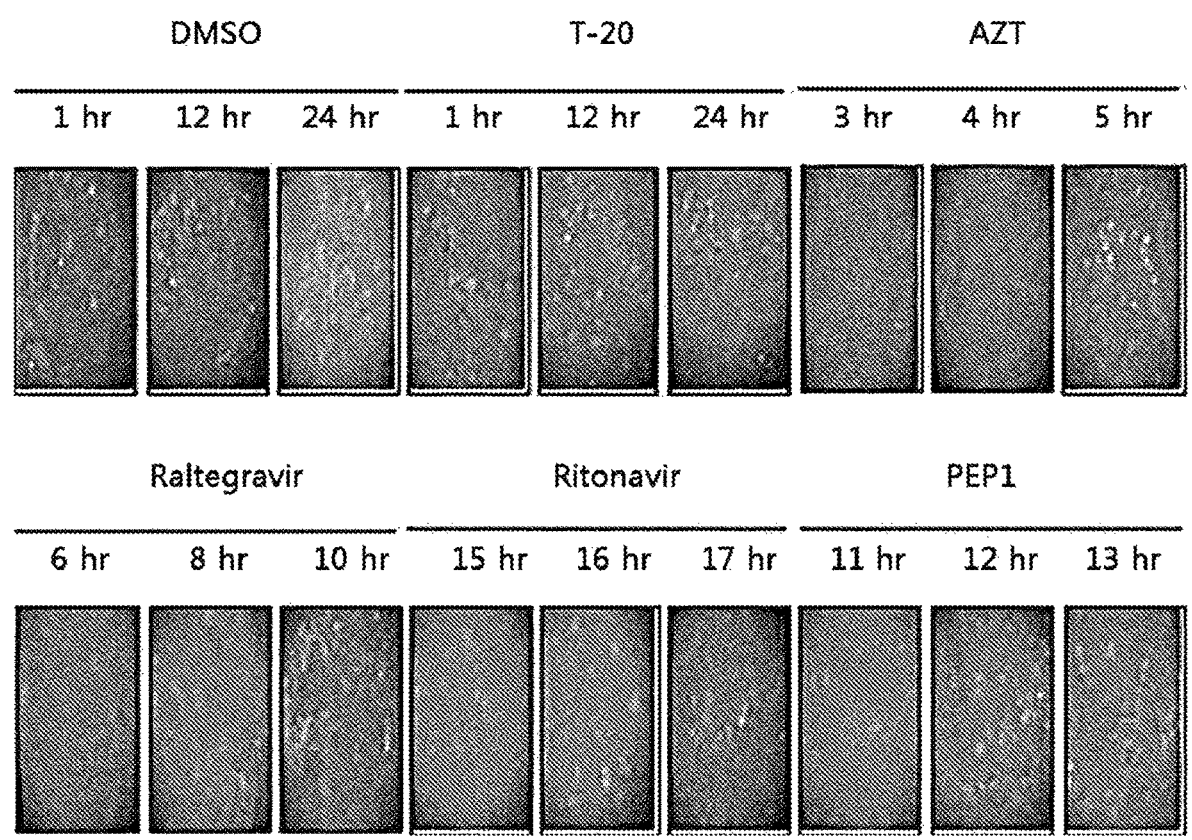

FIG. 29 shows representative eGFP images obtained by a time-of-addition assay.

Figure 30:
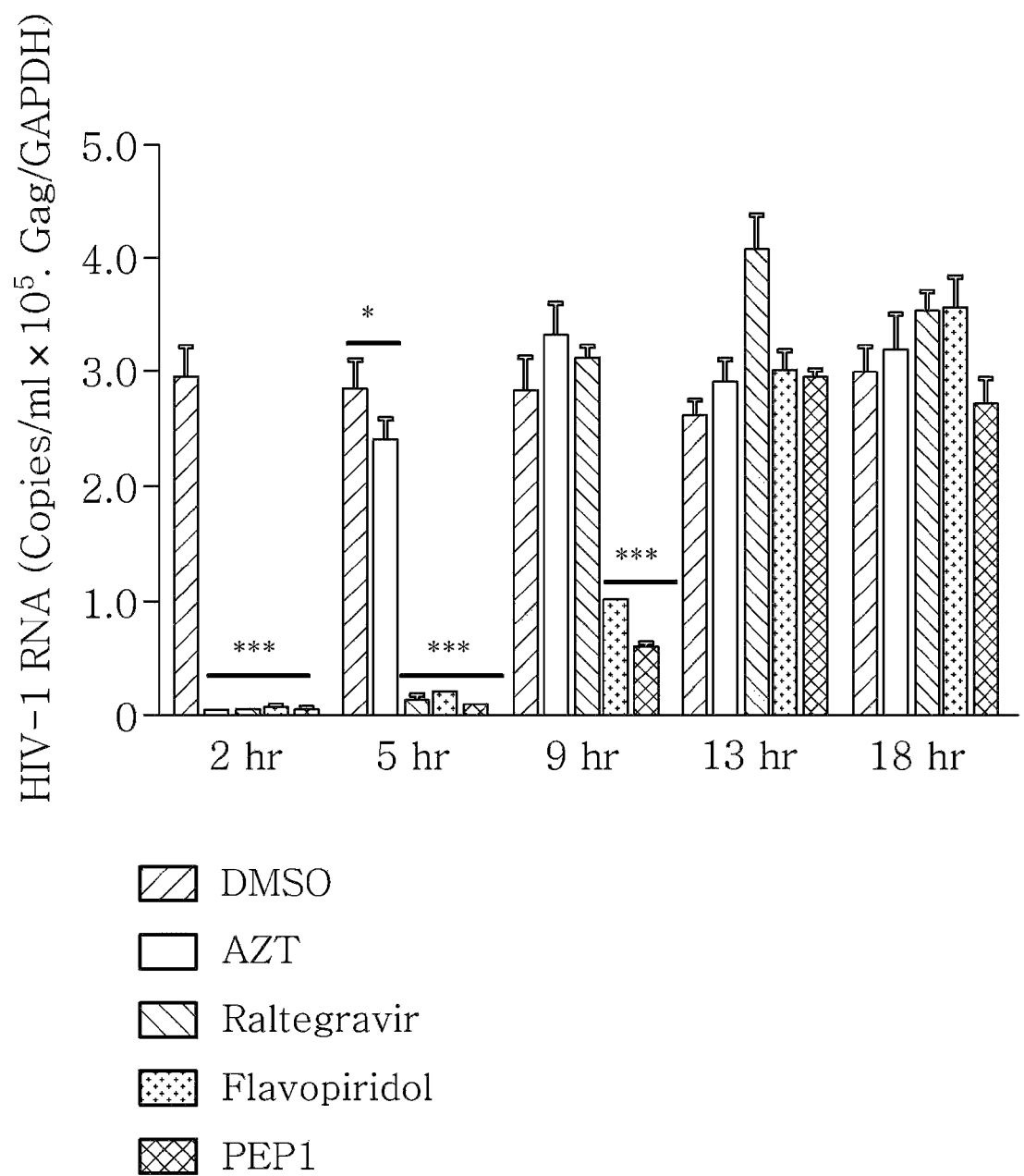

FIG. 30 shows an effect of PEP1 on inhibition of HIV-1 viral mRNA synthesis, analyzed by evaluating viral mRNA levels through RT-qPCR after MT-4 cells are infected with HIV-1, and treated with a vehicle or antiviral drugs at designated time points (Data is expressed as means±SD. * indicates p<0.05 and *** indicates p<0.001, versus DMSO).

Figure 31:
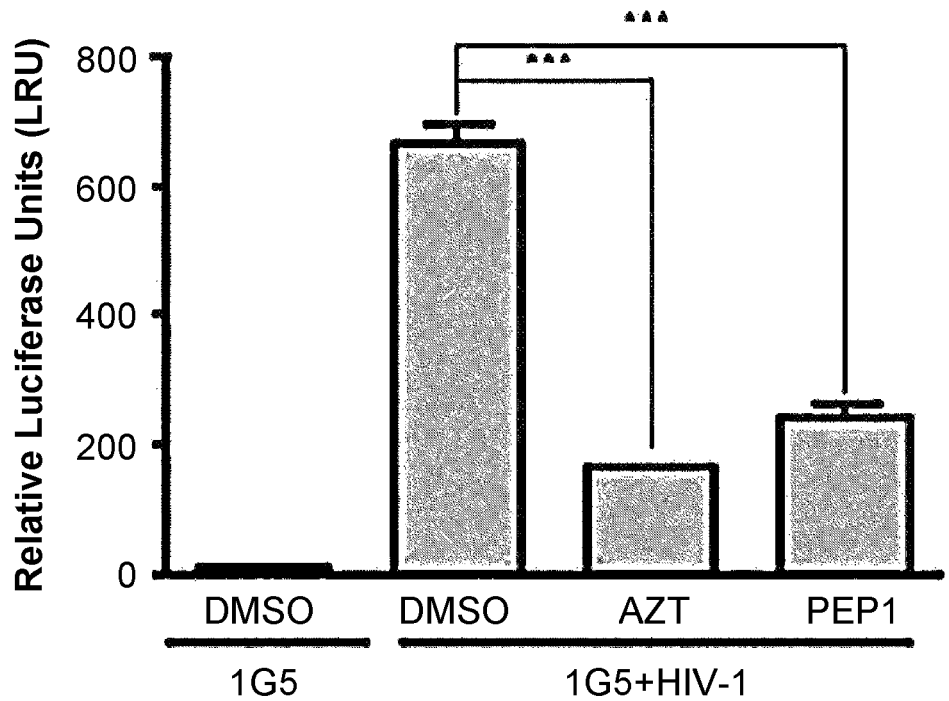

FIG. 31 shows that treatment with AZT or PEP1 reduced the effect of HIV-1 infection relative to HIV-LTR-luciferase activity by approximately five times.

Figure 32:
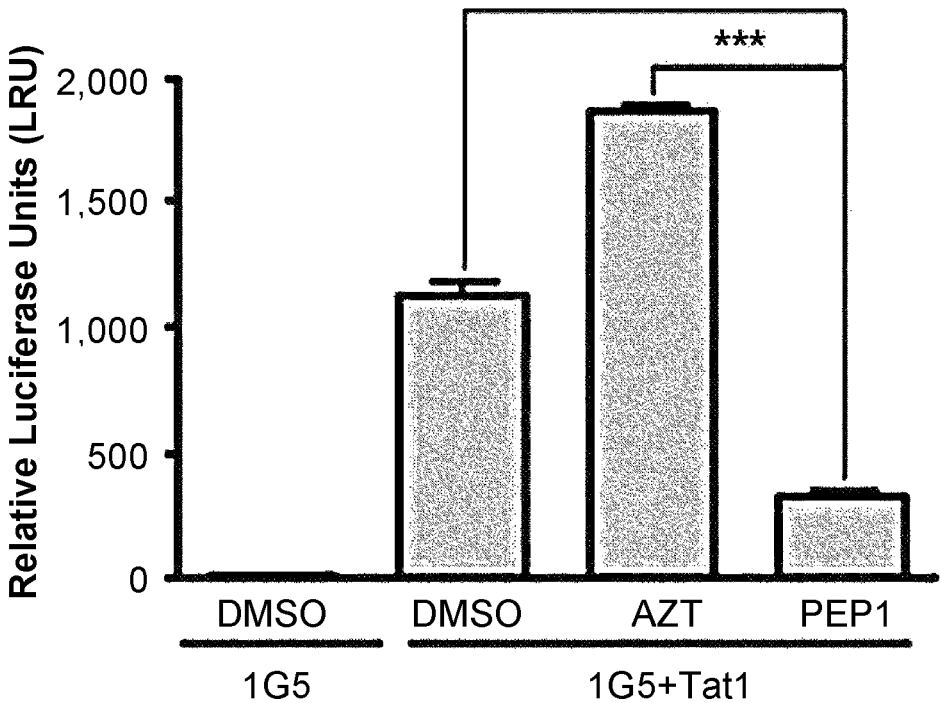

FIG. 32 shows inhibition of Tat-dependent HIV-1 transcription by PEP1.

Figure 33:
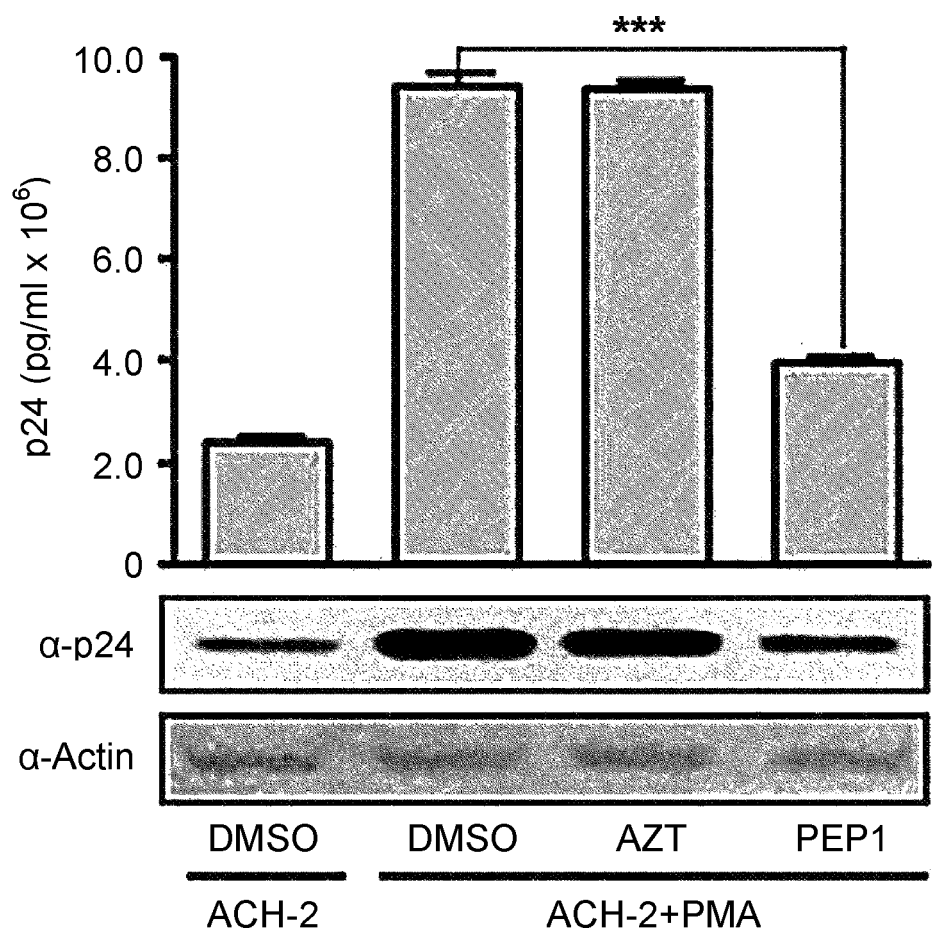

FIG. 33 shows an inhibitory effect of PEP1 on reactivation of HIV-1 after an incubation period.

Figure 34:
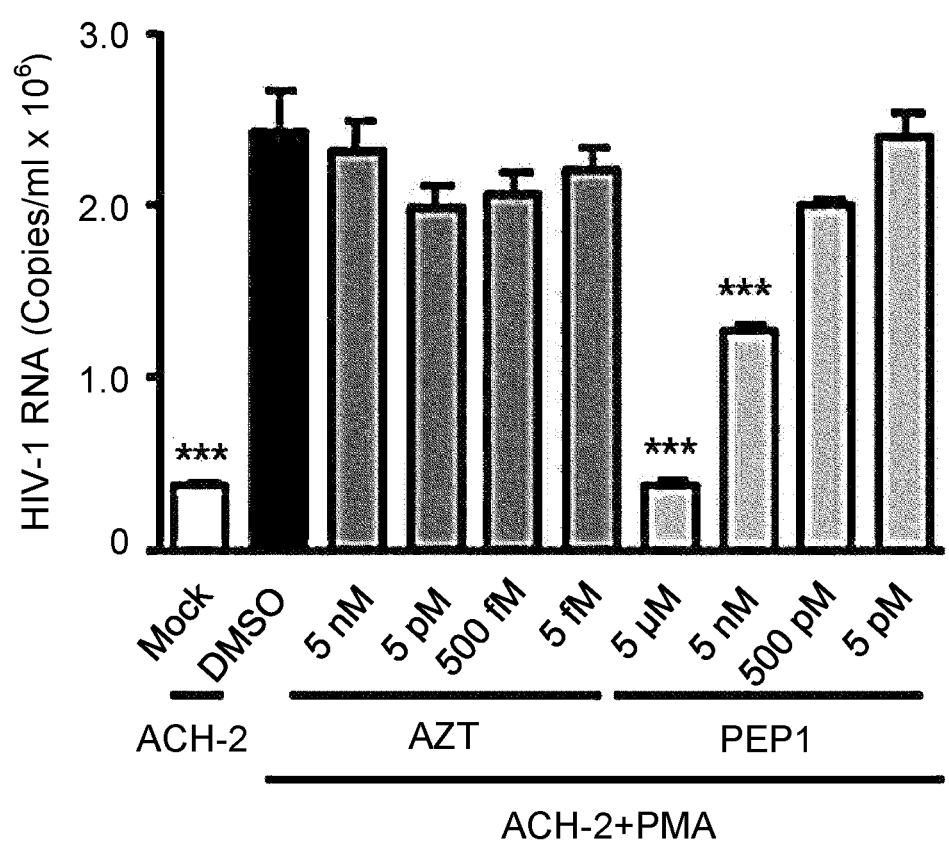

FIG. 34 shows an inhibitory effect of PEP1 on reactivation of HIV-1 after an incubation period.

Figure 35:
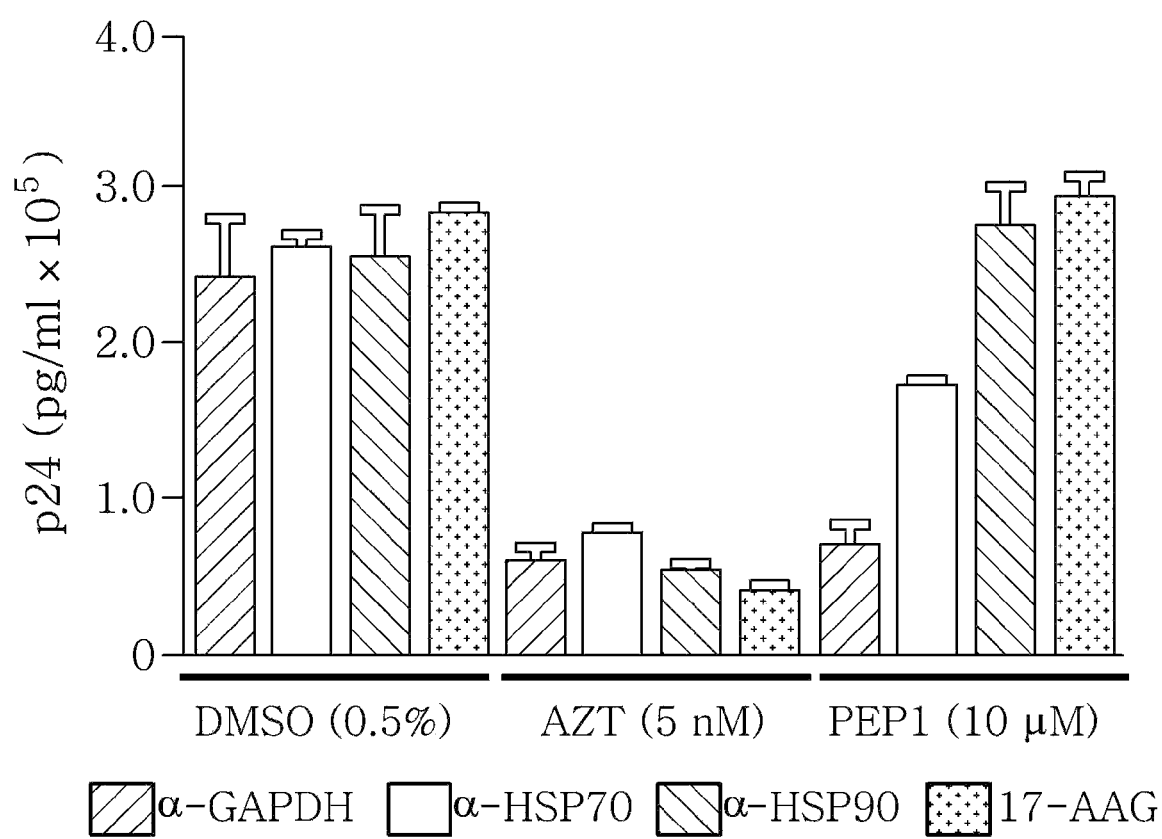

FIG. 35 shows that PEP1 plays an important role of HSP90 when exhibiting an anti-HIV-1 activity.

Figure 36:
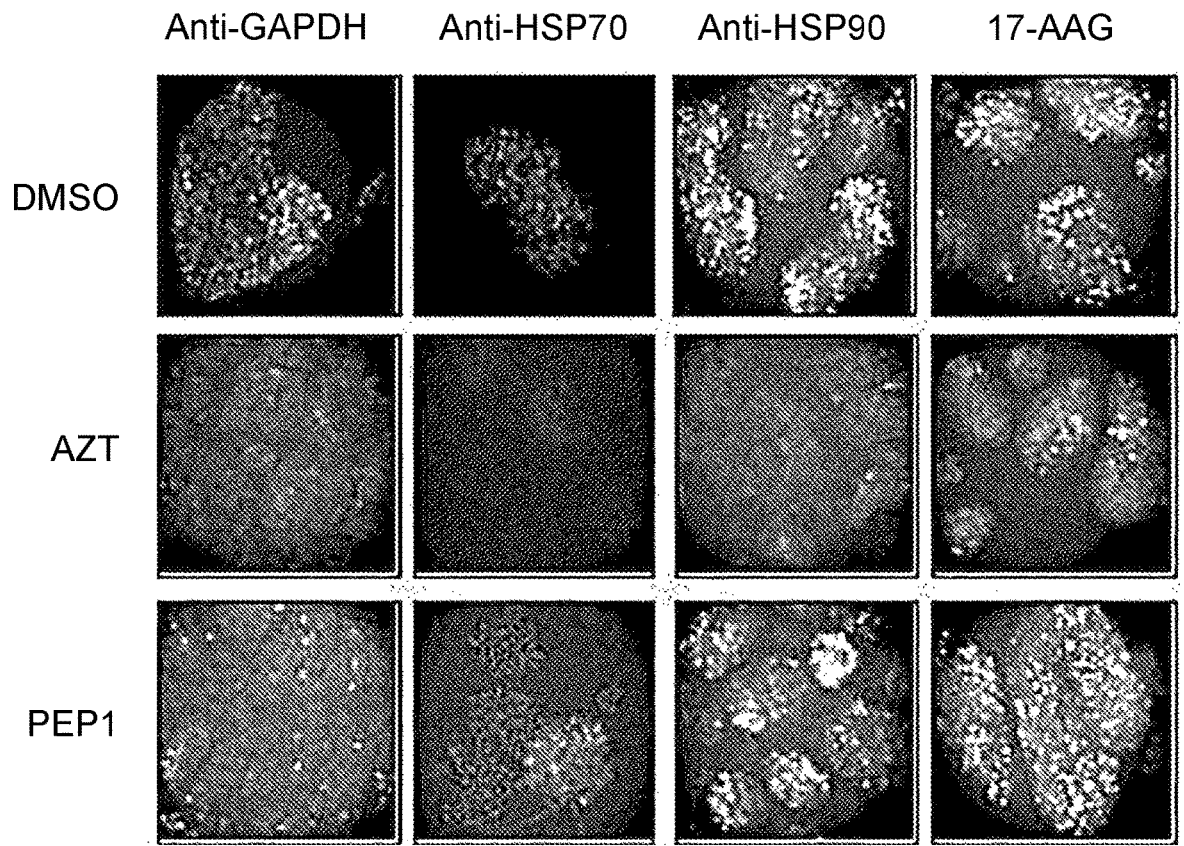

FIG. 36 shows representative eGFP images obtained in FIG. 35.

Figure 37:
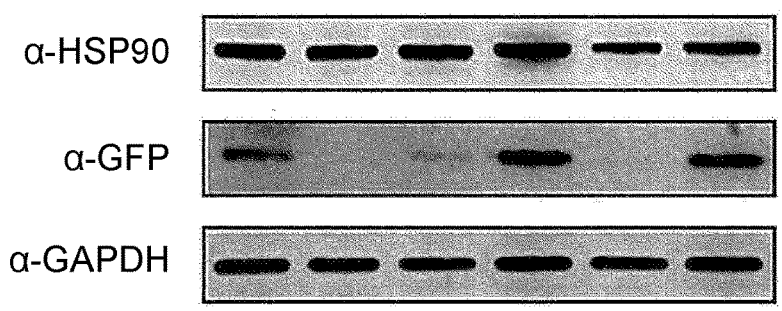

FIG. 37 shows the critical role of HSP90 when PEP1 exhibits an anti-HIV-1 activity.

Figure 38:
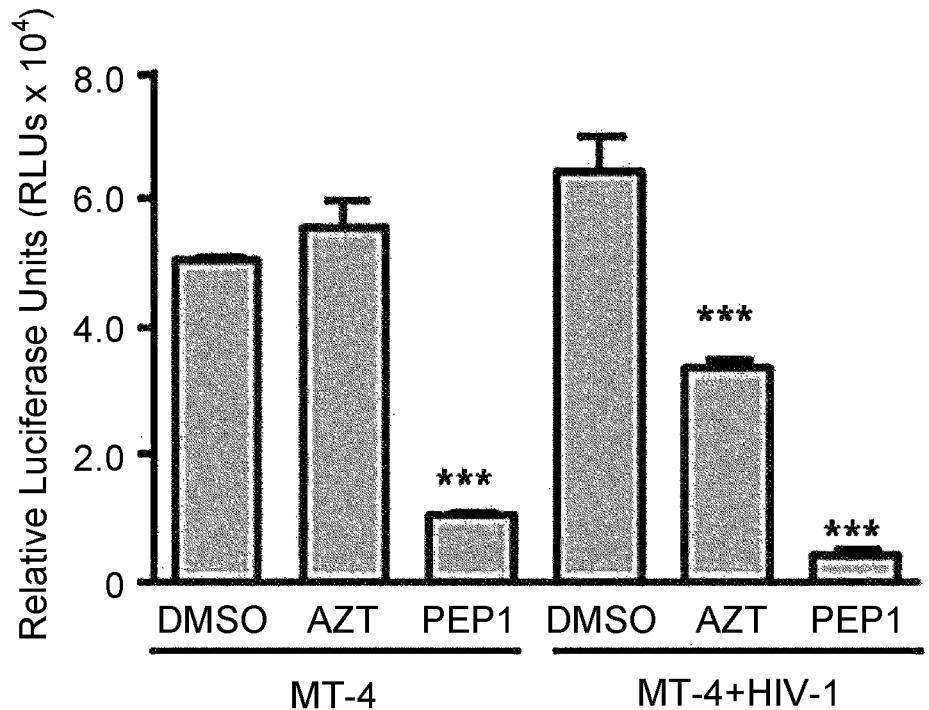

FIG. 38 shows the result of a dual-luciferase assay, performed on MT-4 cells after transfection with NF-κB firefly luciferase and CMV-promoter renilla luciferase reporter plasmids and then with HIV-1 ($1\times10^6$ $CCID_{50}$), and treated with designated compounds for 24 hours (Data is expressed as means±SD. *** indicates p<0.001 versus DMSO).

Figure 39:
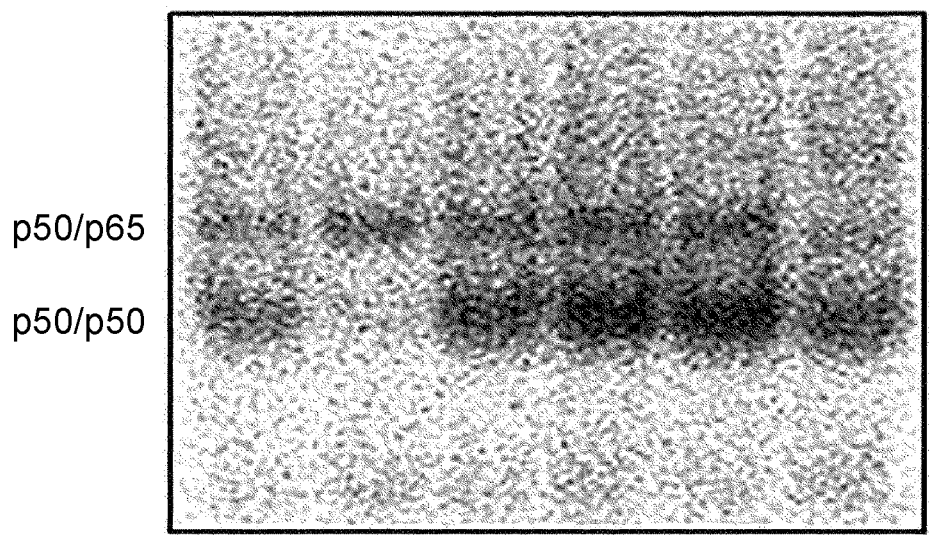

FIG. 39 shows the result of an electrophoretic mobility shift assay (EMSA), performed on MT-4 cells after infection with HIV-1, and then treated with DMSO, AZT or PEP1 as described in FIG. 38, and subjected to extraction of a nuclear fraction after 24 hours.

Figure 40:
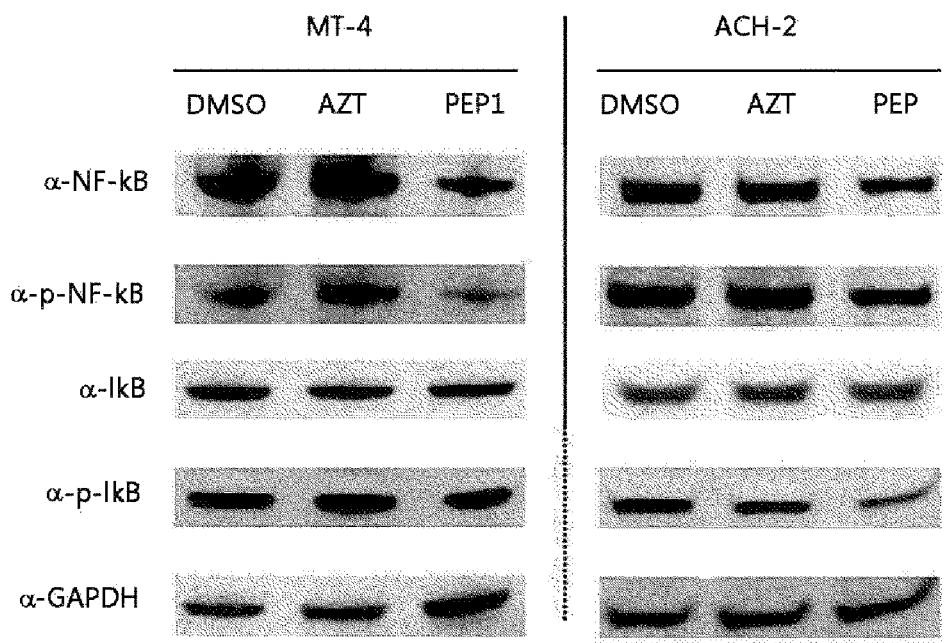

FIG. 40 shows the use of NF-κB and AP-2 competitive oligomers to confirm accuracy.

Figure 41:
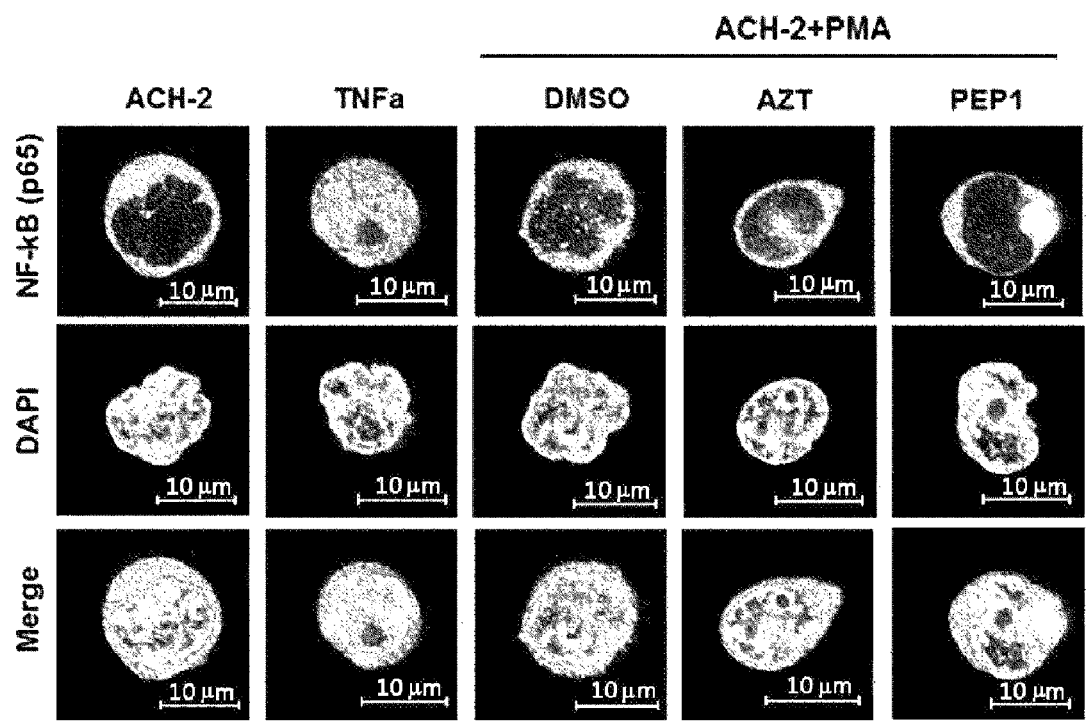

FIG. 41 shows ACH-2 cells observed by a confocal microscope, after stimulation with TNF-α (30 ng/ml) or phorbol 12-myristate 13-acetate (PMA) (50 nM) for one hour, treated with DMSO, AZT or PEP1 for 24 hours, permeabilized by anti-p65 NF-κB antibodies and Alexa-fluorescent 594-conjugated secondary antibodies, and stained by simple DAPI nuclear staining.

Figure 42:
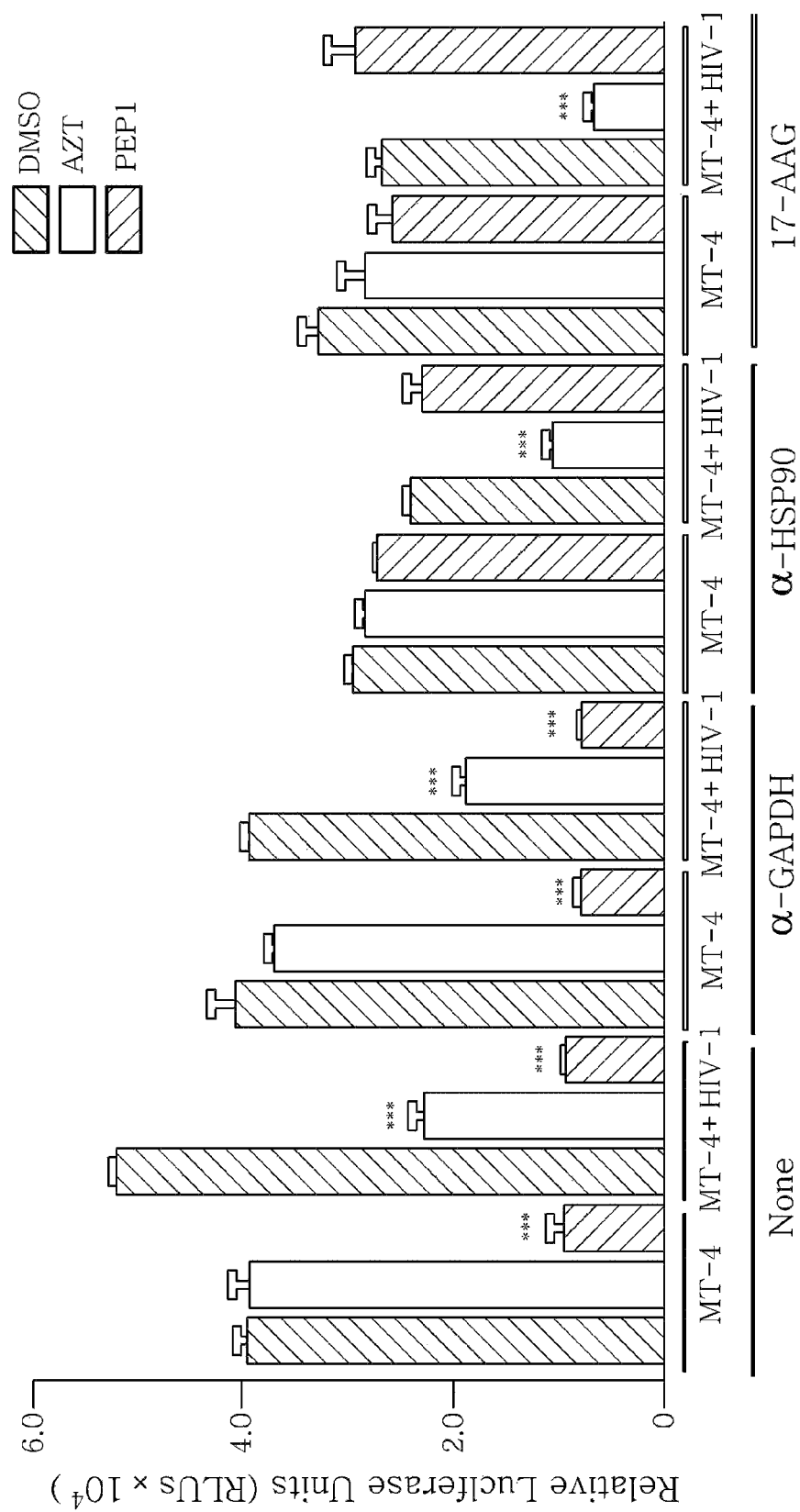

FIG. 42 shows the result of a dual-luciferase assay performed on MT-4 cells after transfection with NF-κB firefly luciferase and CMV-promoter renilla luciferase reporter plasmids, treated with designated antibodies (10 ng/ml) or 17-AAG (1 μM) for 1 hour before HIV-infection, and treated with DMSO, AZT or PEP1 for 24 hours after HIV-infection (Data is expressed as means±SD. *** indicates p<0.001 versus DMSO).

Figure 43:
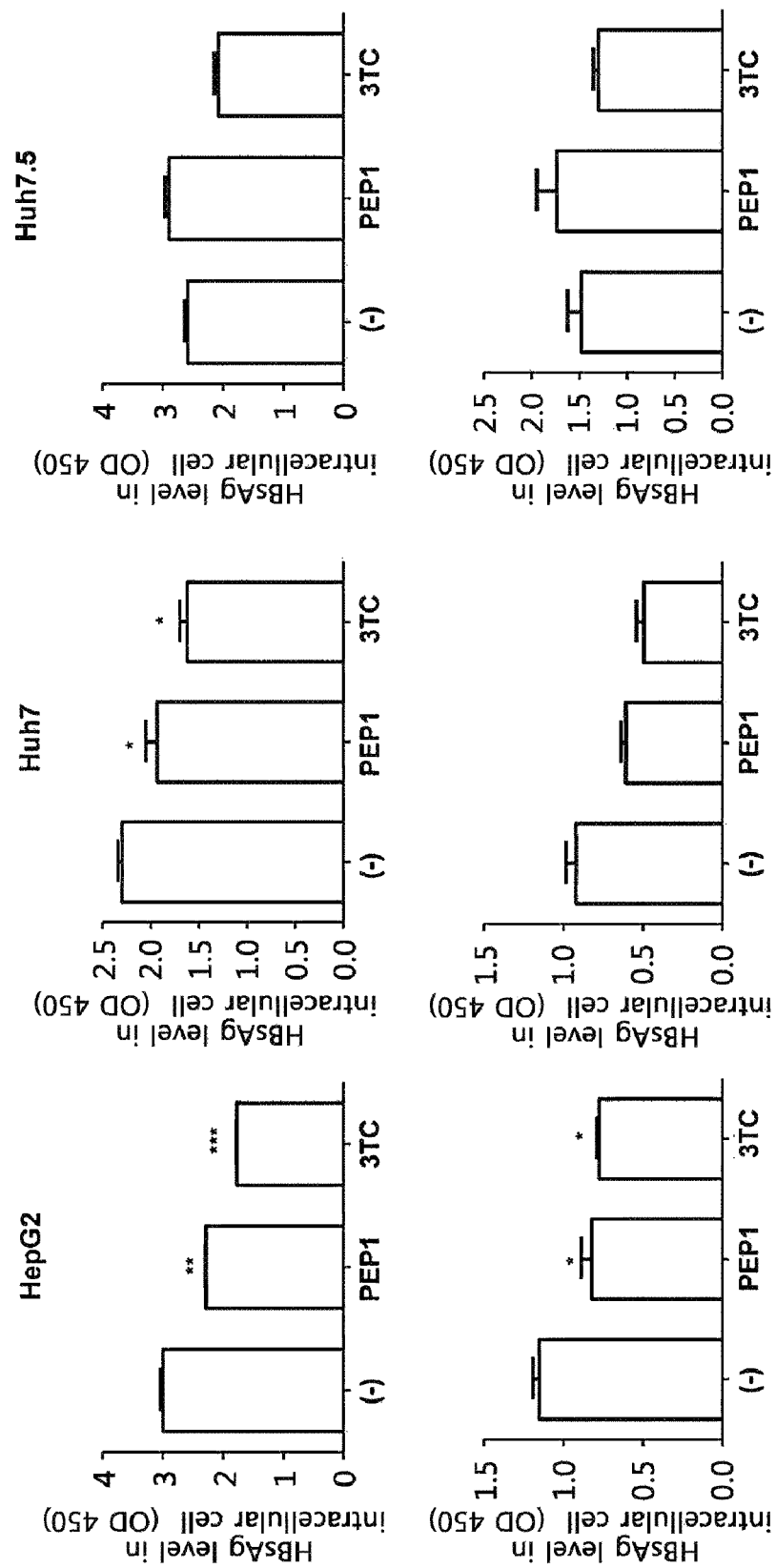

FIG. 43 shows the comparison in HBsAg synthesis by PEP1 in various human liver cancer cell lines transfected with the whole HBV W4P genome.

Figure 44A:
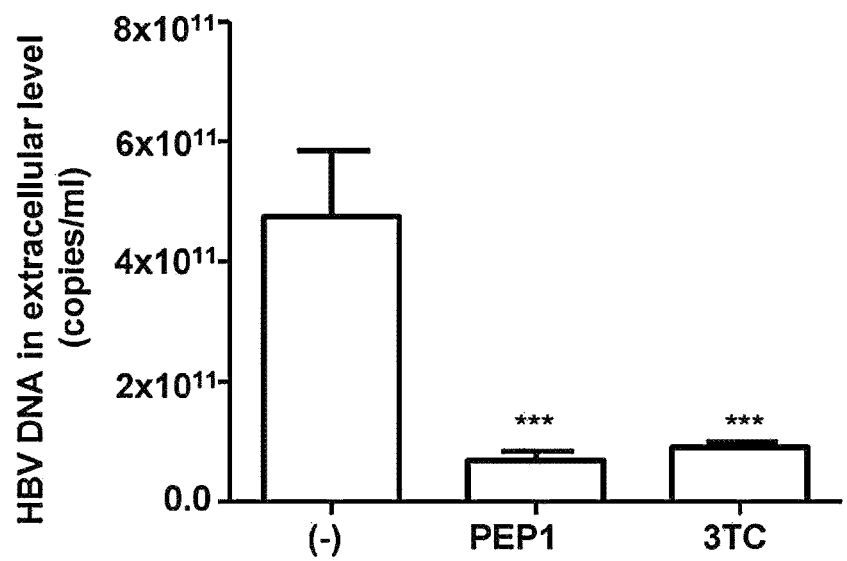

FIG. 44*a* shows the comparison in virion formation by the PEP1 peptide in an HepG2 cell line transfected with the whole HBV W4P genome.

Figure 44B:
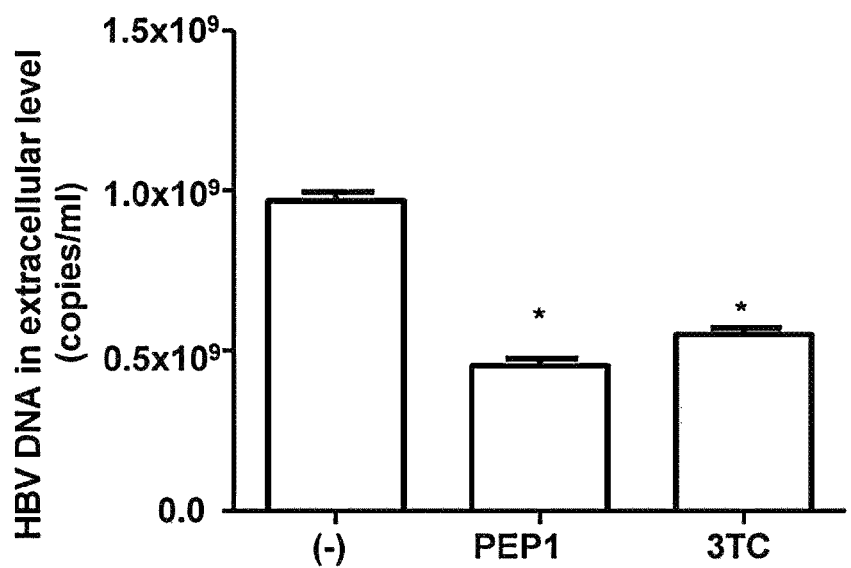

FIG. 44b shows the comparison in virion formation by the PEP1 peptide in an Huh7 cell line transfected with the whole HBV W4P genome.

Figure 44C:
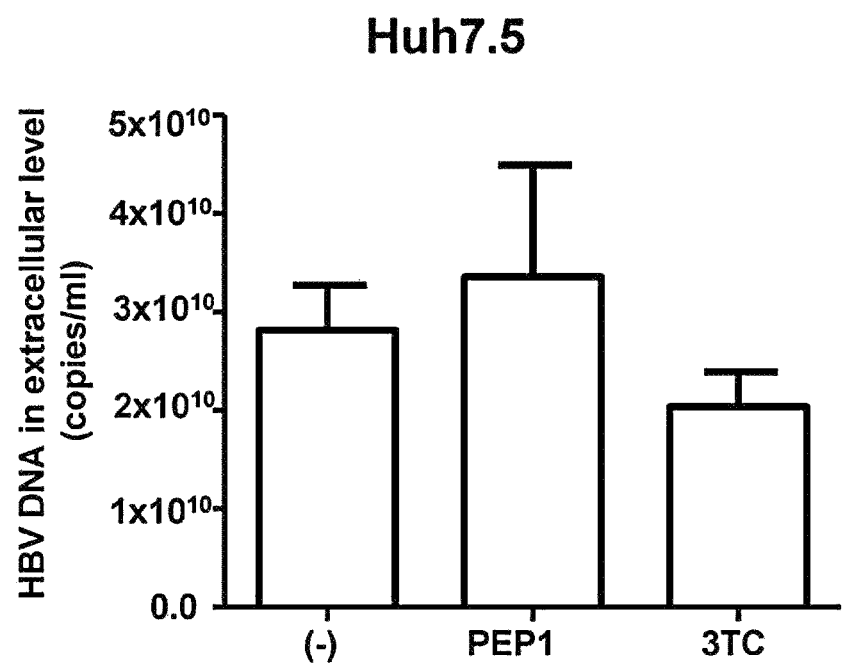

FIG. 44c shows the comparison in virion formation by the PEP1 peptide in an Huh7.5 cell line transfected with the whole HBV W4P genome.

Figure 45:
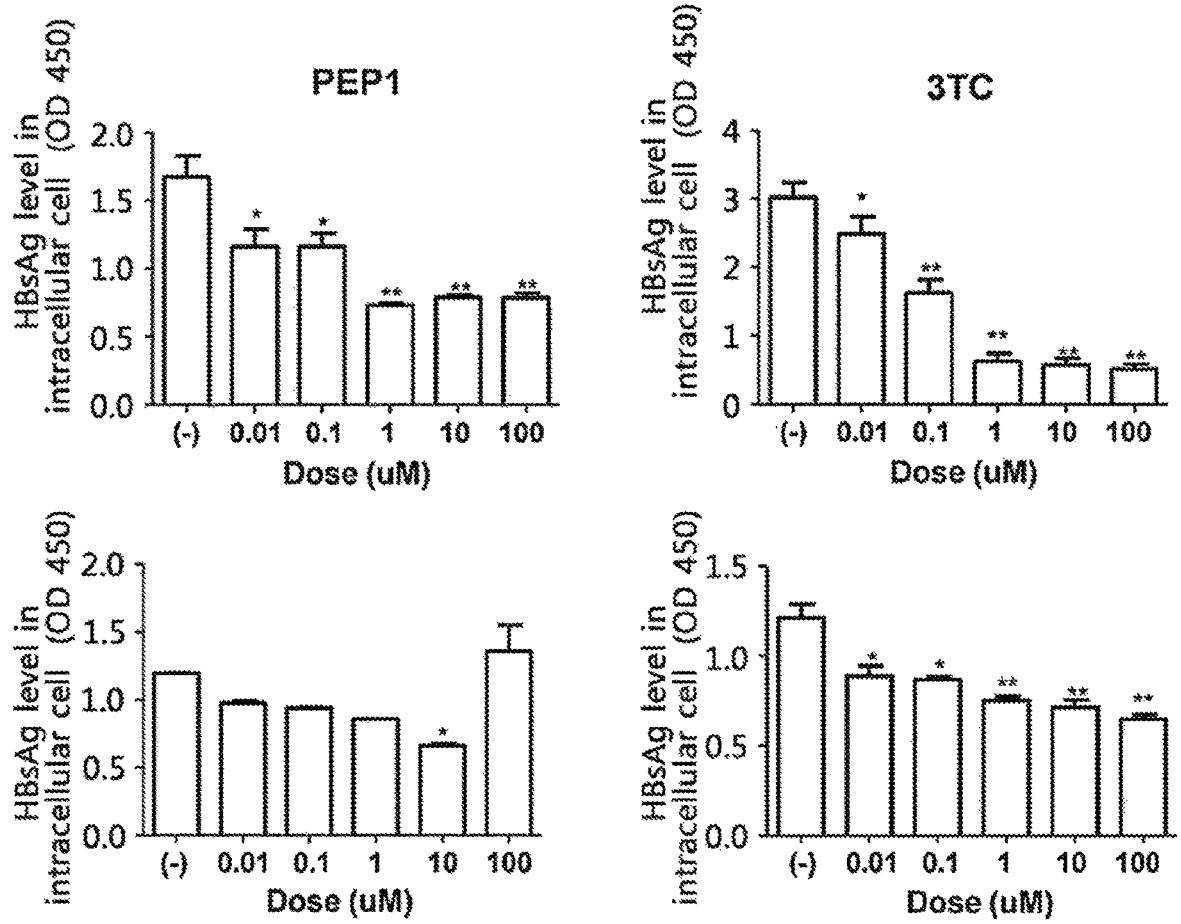

FIG. 45 shows the comparison in HBsAg synthesis depending on the concentration of the PEP1 peptide in an HepG2 cell line transfected with the whole HBV W4P genome.

Figure 46:
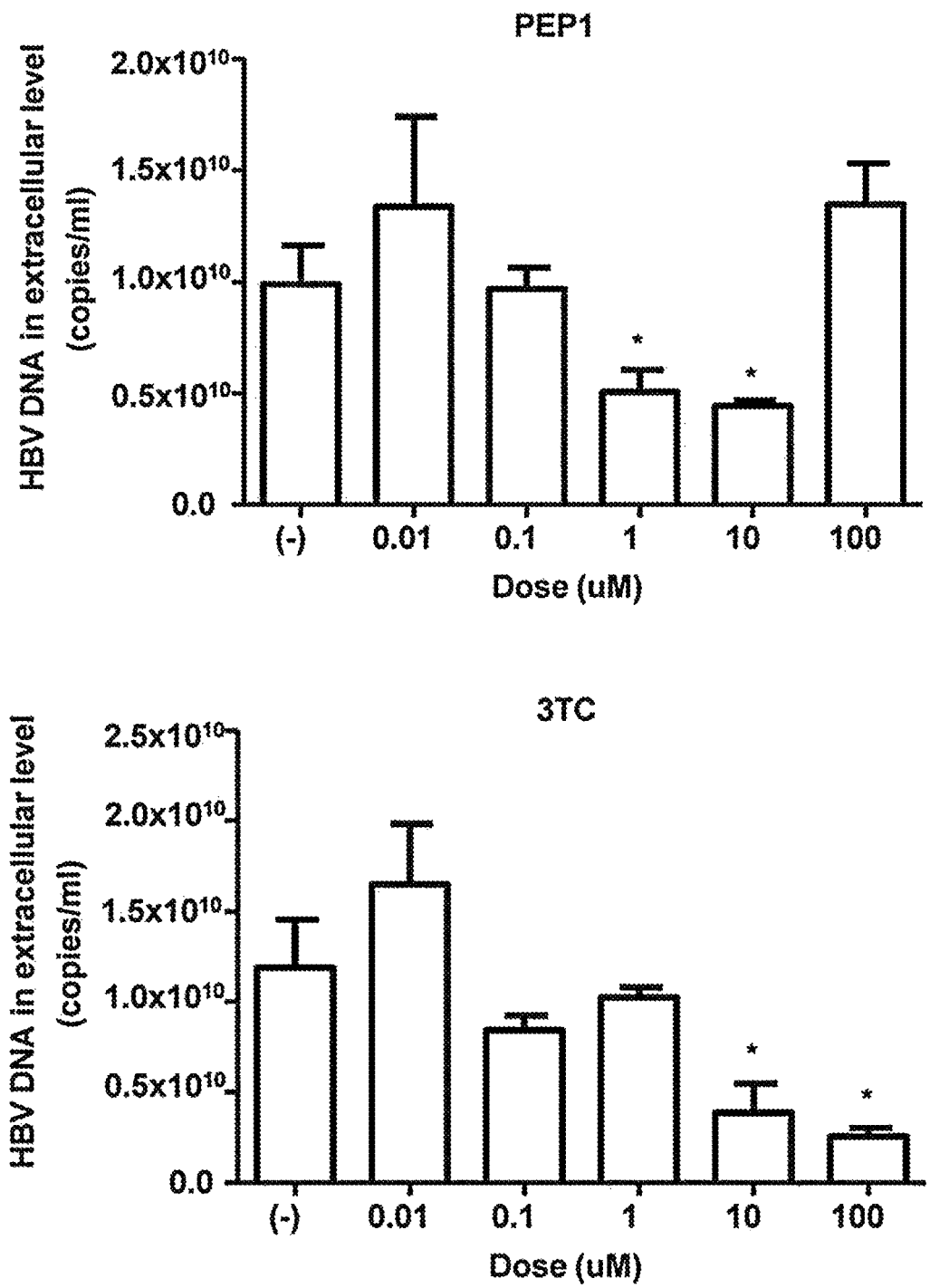

FIG. 46 shows the comparison in virion synthesis depending on the concentration of the PEP1 peptide in an HepG2 cell line transfected with the whole HBV W4P genome.

Figure 47:
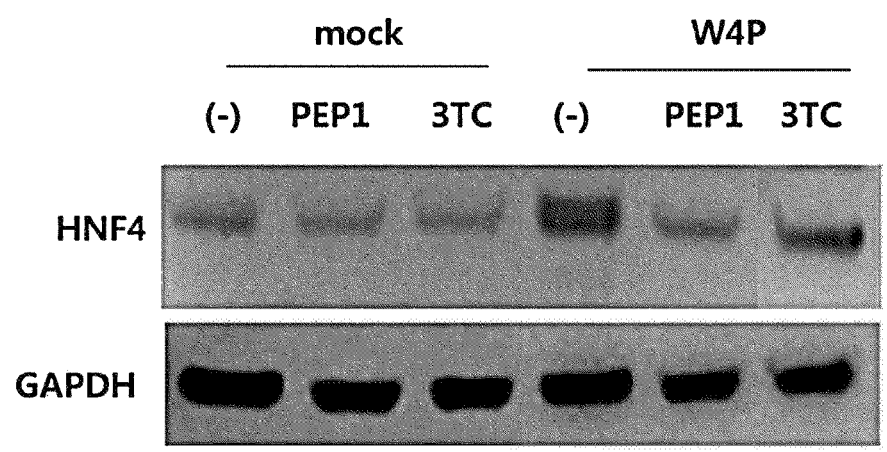

FIG. 47 shows the effect of the PEP1 peptide on HNF4α expression, analyzed by western blotting.

Figure 48:
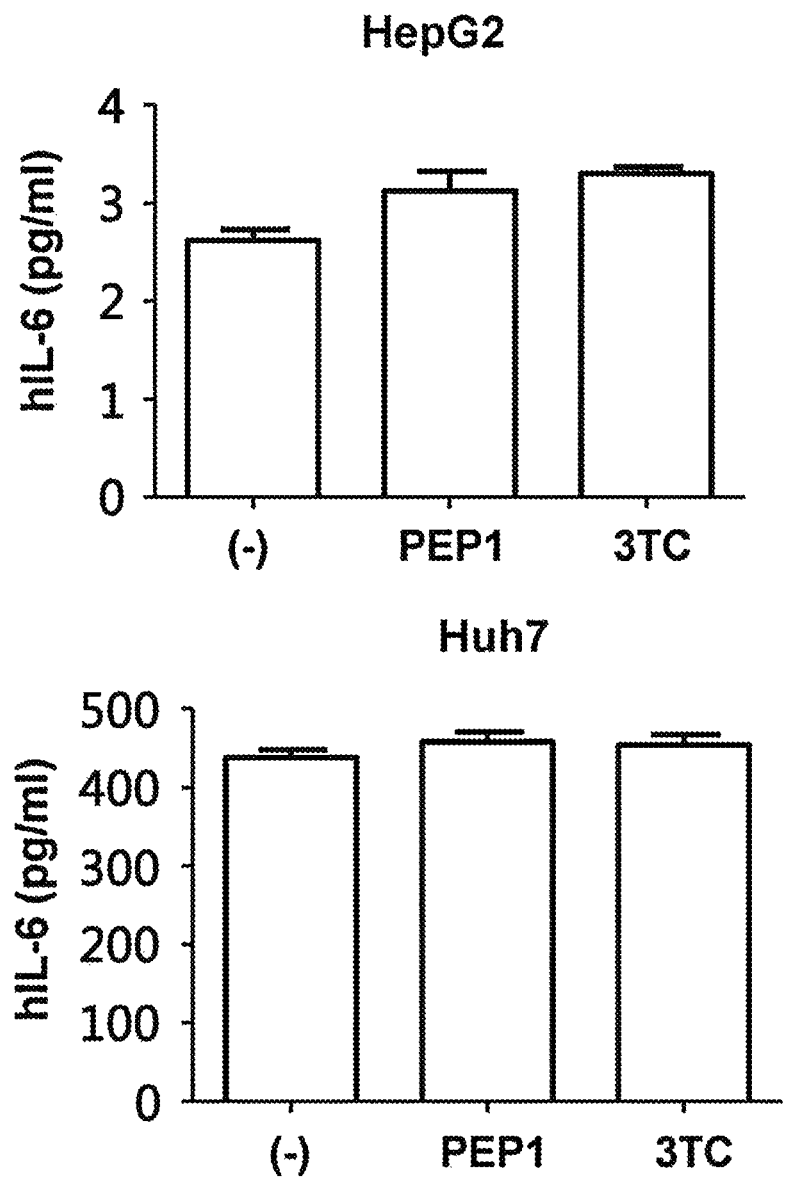

FIG. 48 shows an effect of the PEP1 peptide on IL-6.

Figure 49:
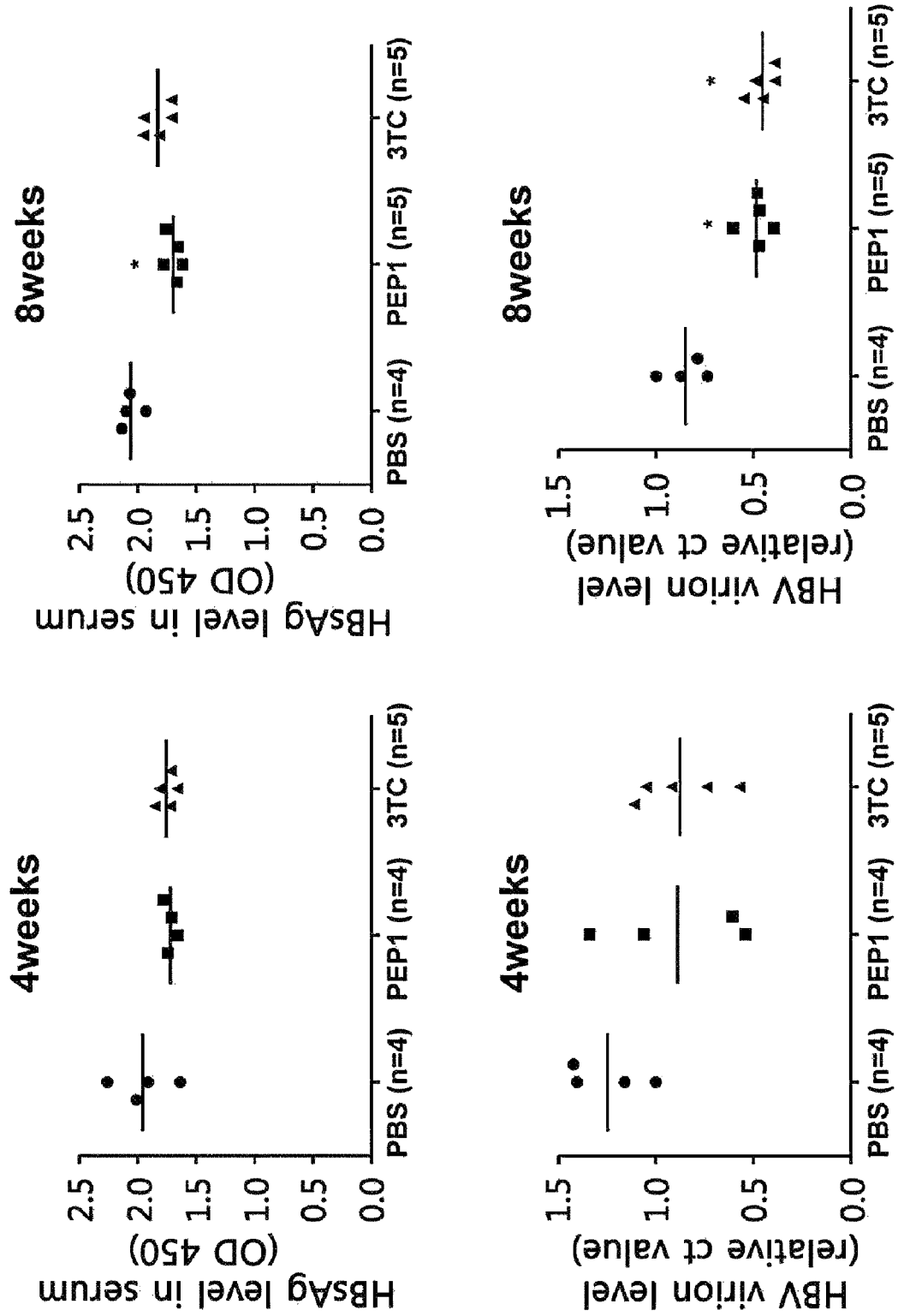

FIG. 49 shows the effect of PEP1 on HBsAg synthesis and virions in whole HBV W4P genome-transgenic mice.

Figure 50:
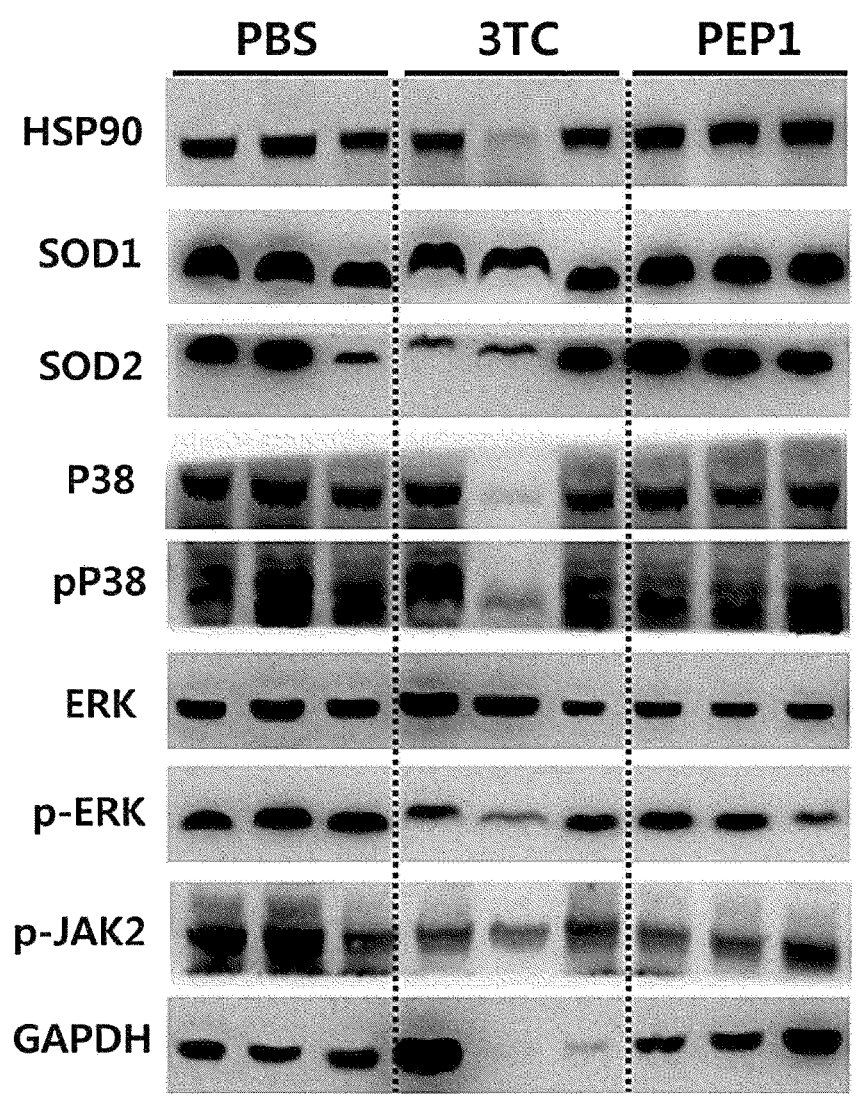

FIG. 50 shows the effect of the PEP1 peptide on protein expression in whole HBV W4P genome-transgenic mice.

Figure 51A:
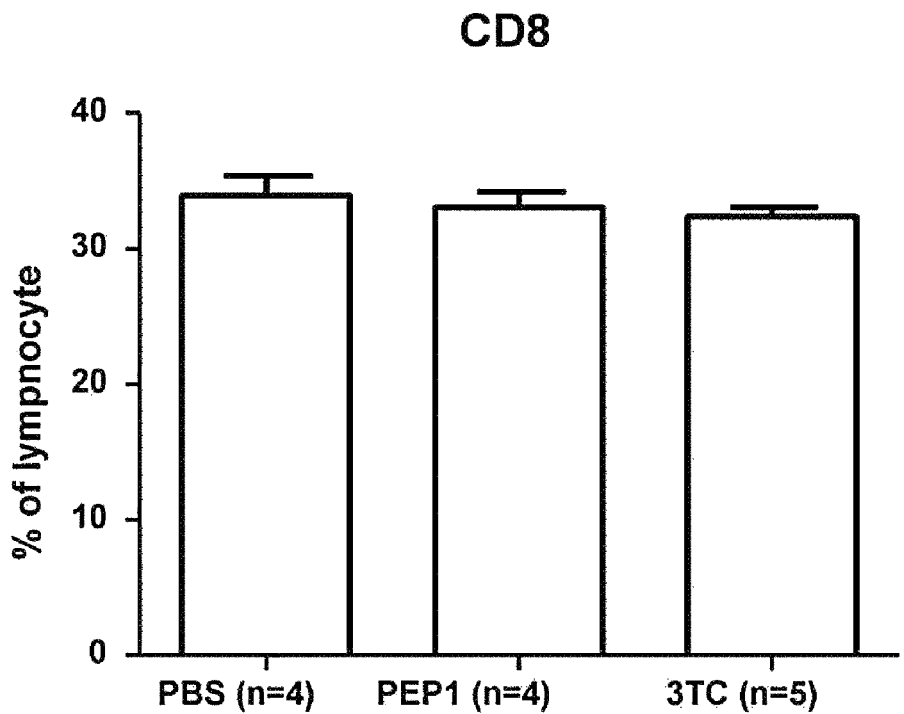

FIG. 51a shows the effect of the PEP1 peptide on distribution of immunocytes (lymphocyte CD8) in whole HBV W4P genome-transgenic mice.

Figure 51B:
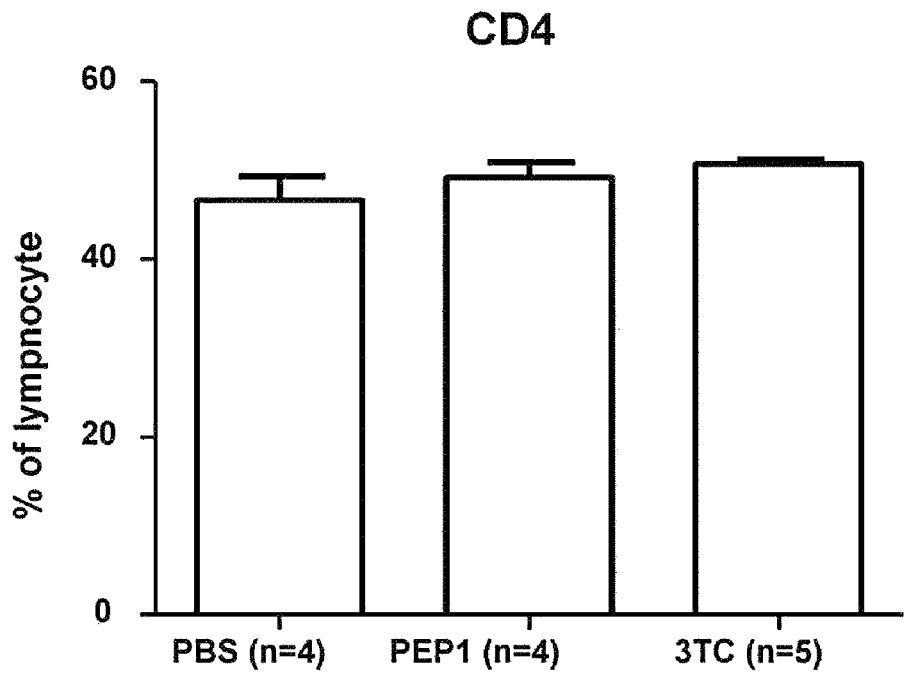

FIG. 51b shows the effect of the PEP1 peptide on distribution of immunocytes (lymphocyte CD4) in whole HBV W4P genome-transgenic mice.

Figure 51C:
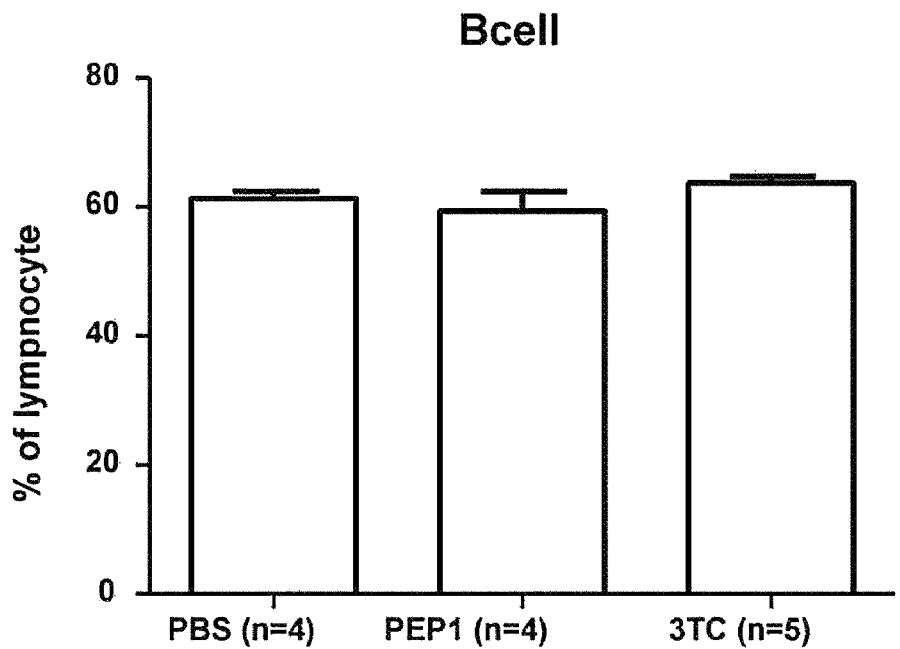

FIG. 51c shows the effect of the PEP1 peptide on distribution of immunocytes (lymphocyte B cells) in whole HBV W4P genome-transgenic mice.

Figure 51D:
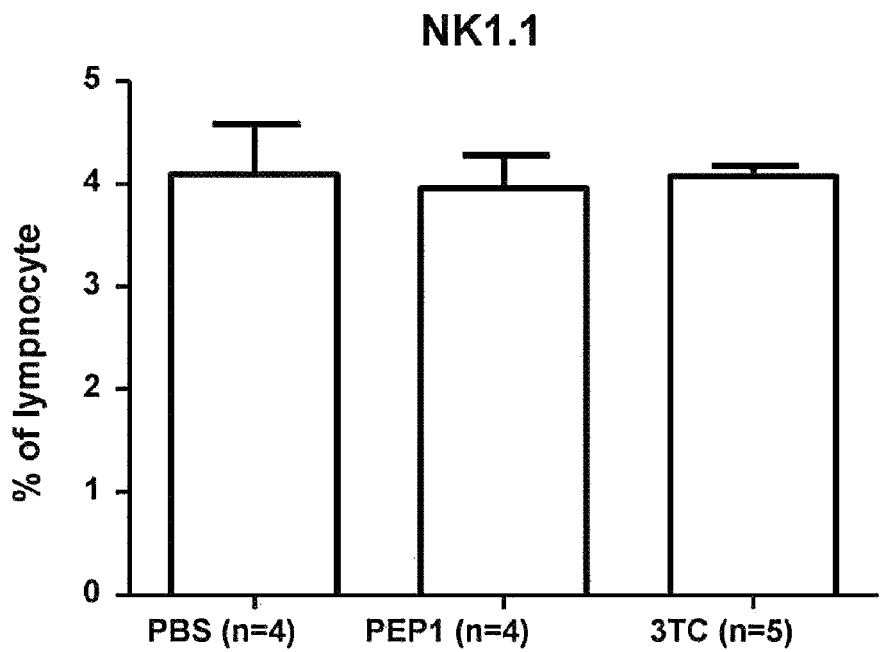

FIG. 51d shows the effect of the PEP1 peptide on distribution of immunocytes (lymphocyte NK1.1) in whole HBV W4P genome-transgenic mice.

Figure 51E:
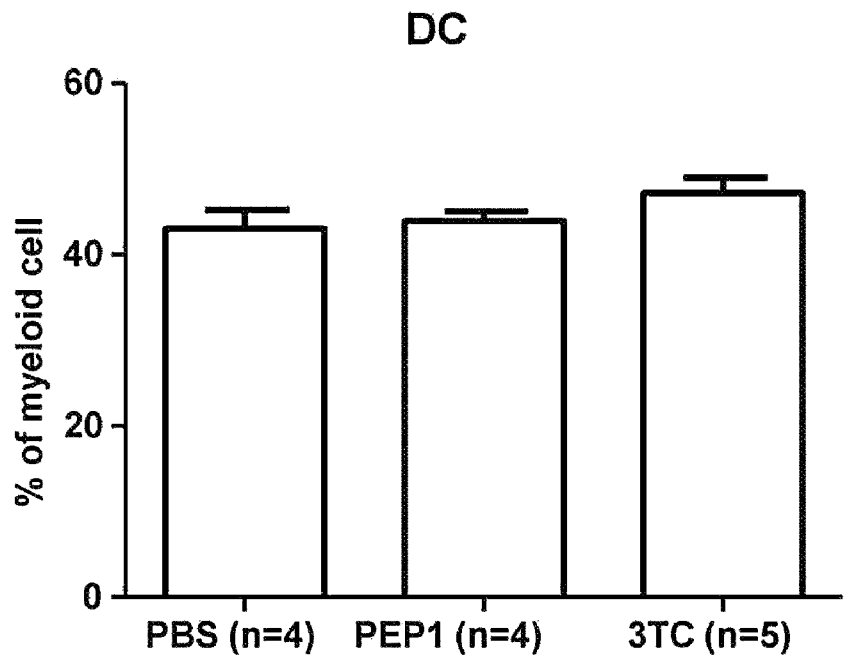

FIG. 51e shows the effect of the PEP1 peptide on distribution of immunocytes (myeloid dendritic cells, myeloid DC) in whole HBV W4P genome-transgenic mice.

Figure 51F:
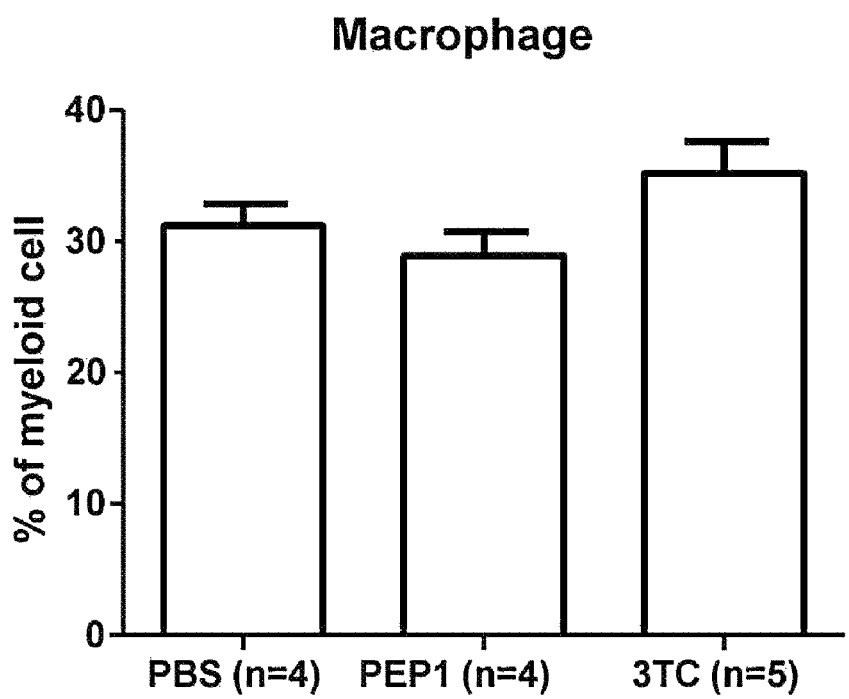

FIG. 51f shows the effect of the PEP1 peptide on distribution of immunocytes (macrophages) in whole HBV W4P genome-transgenic mice.

Figure 51G:
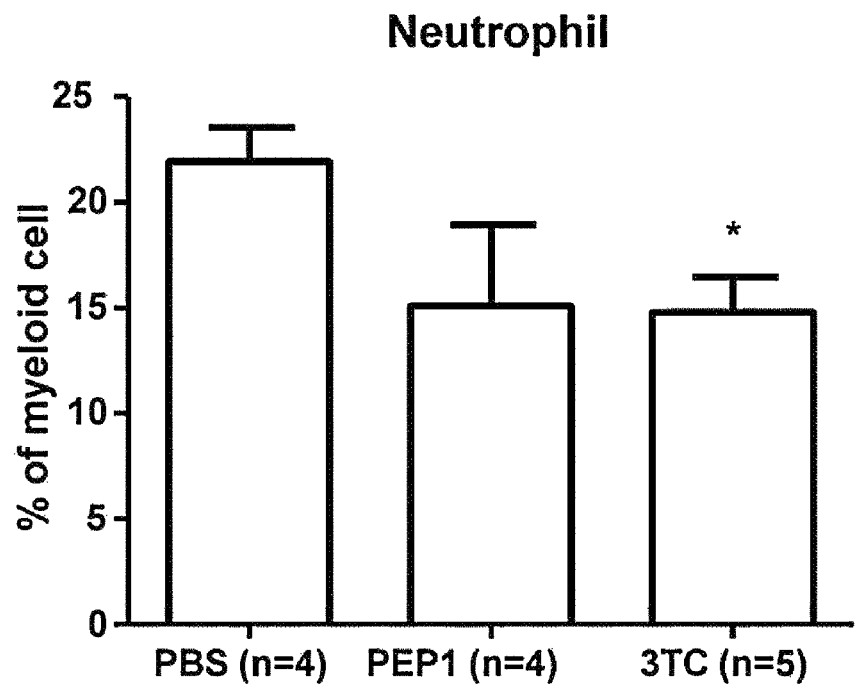

FIG. 51g shows the effect of the PEP1 peptide on distribution of immunocytes (neutrophils) in whole HBV W4P genome-transgenic mice.

Figure 51H:
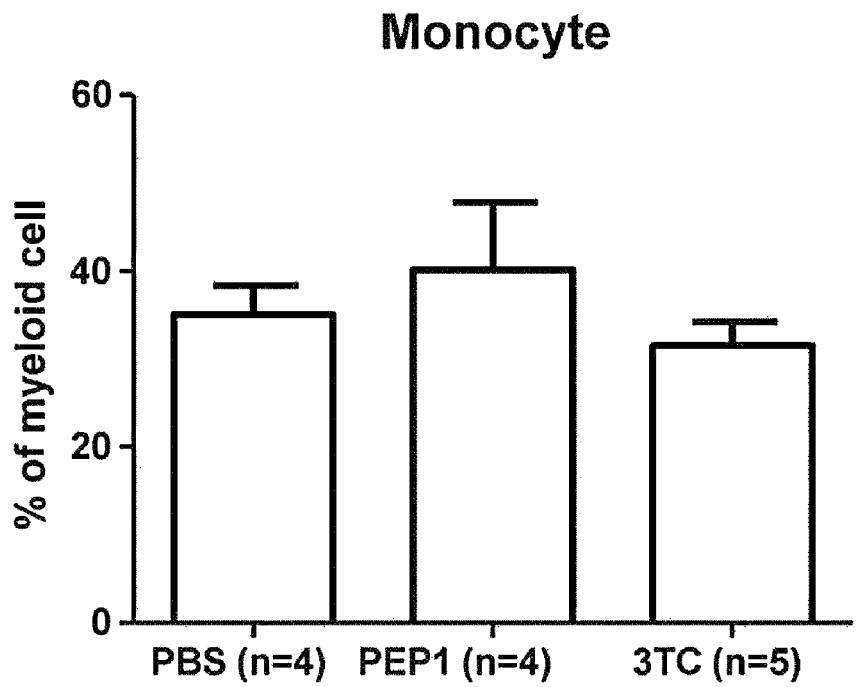

FIG. 51h shows the effect of the PEP1 peptide on distribution of immunocytes (monocytes) in whole HBV W4P genome-transgenic mice.

Figure 52A:
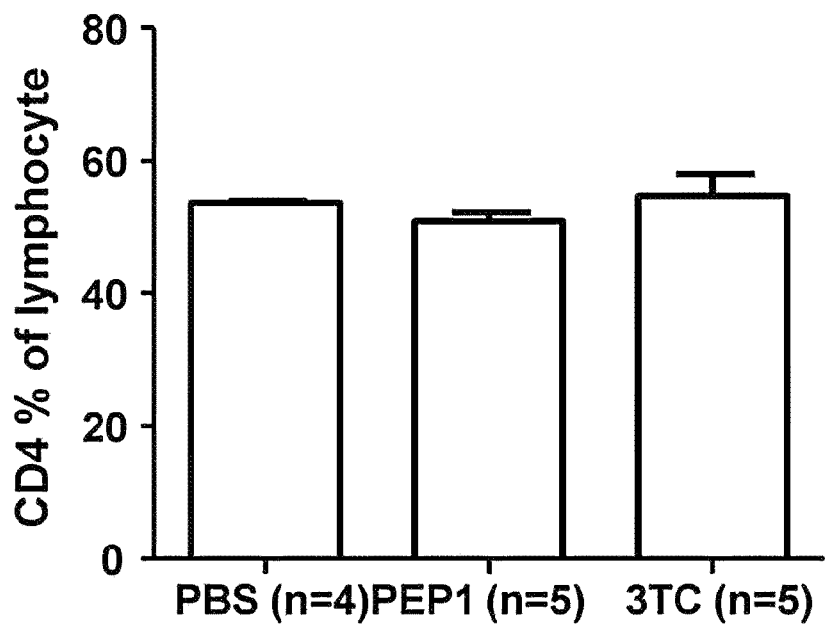

FIG. 52a shows the effect of the PEP1 peptide on activation of immunocytes (lymphocyte CD4) and INFγ.

Figure 52B:
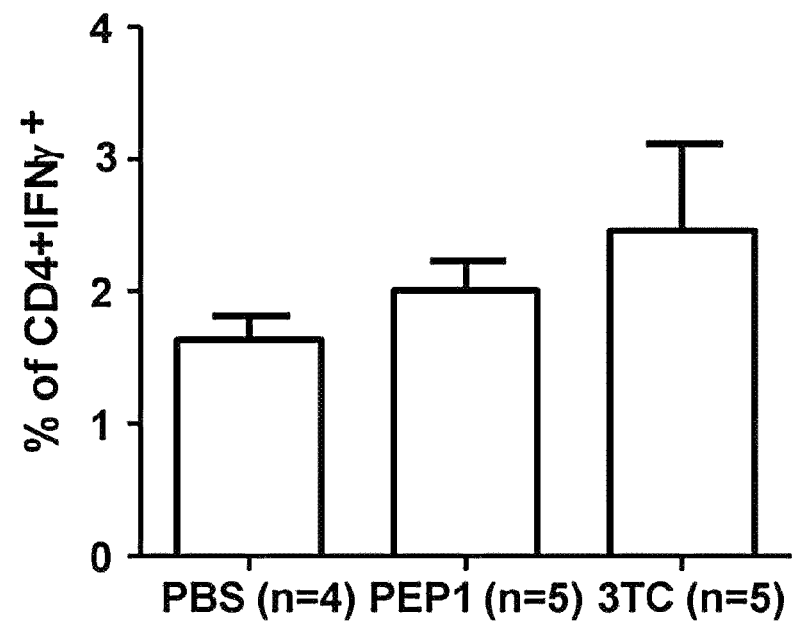

FIG. 52b shows the effect of the PEP1 peptide on activation of immunocytes (lymphocyte CD4) and INFγ.

Figure 52C:
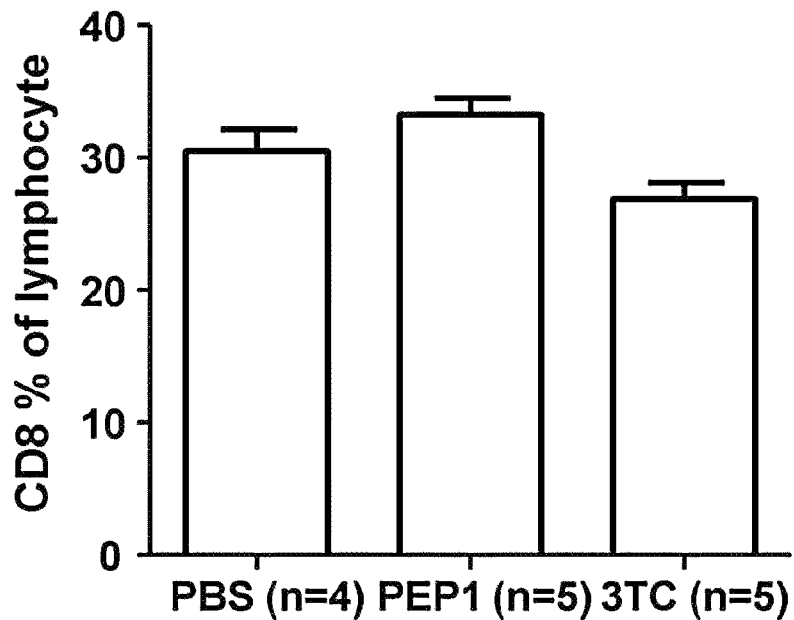

FIG. 52c shows the effect of the PEP1 peptide on activation of immunocytes (lymphocyte CD8) and INFγ.

Figure 52D:
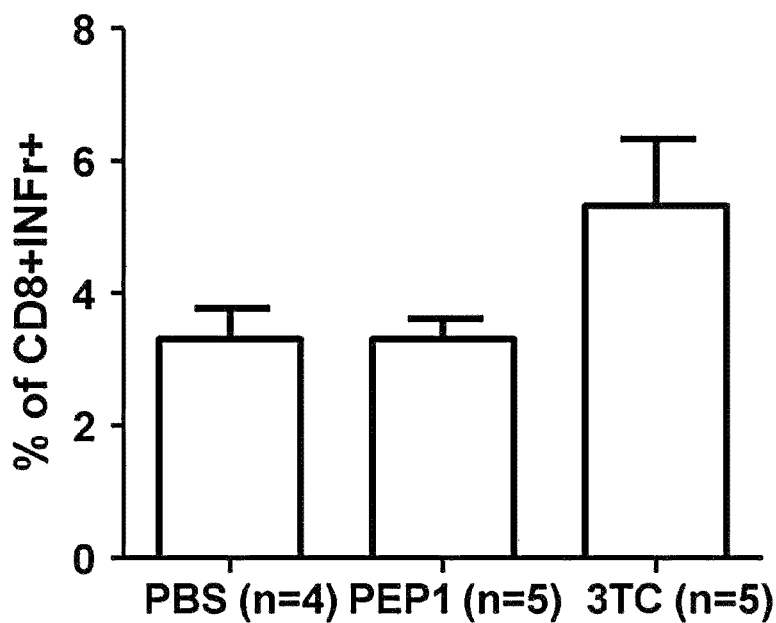

FIG. 52d shows the effect of the PEP1 peptide on activation of immunocytes (lymphocyte CD8) and INFγ.

Figure 52E:
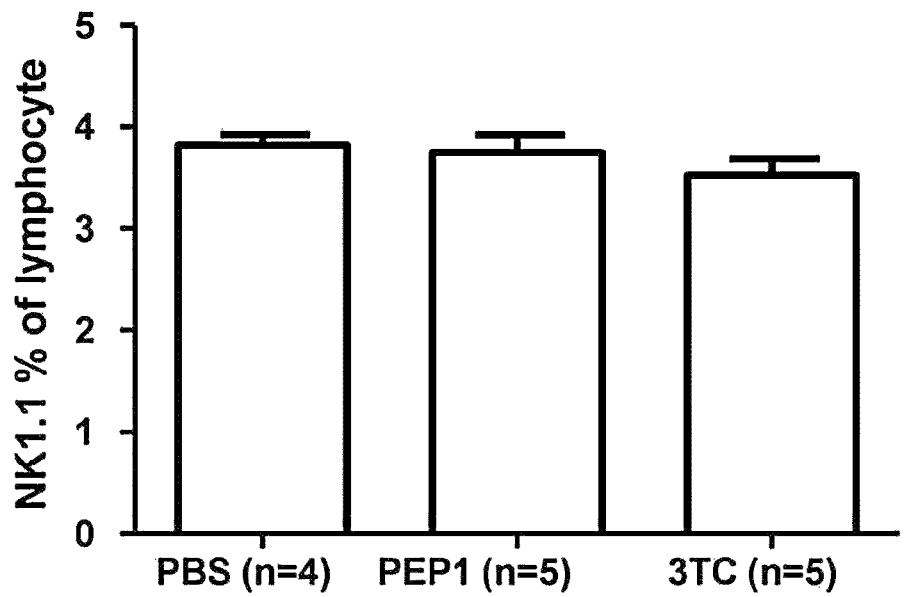

FIG. 52e shows the effect of the PEP1 peptide on activation of immunocytes (NK1.1) and INFγ.

Figure 52F:
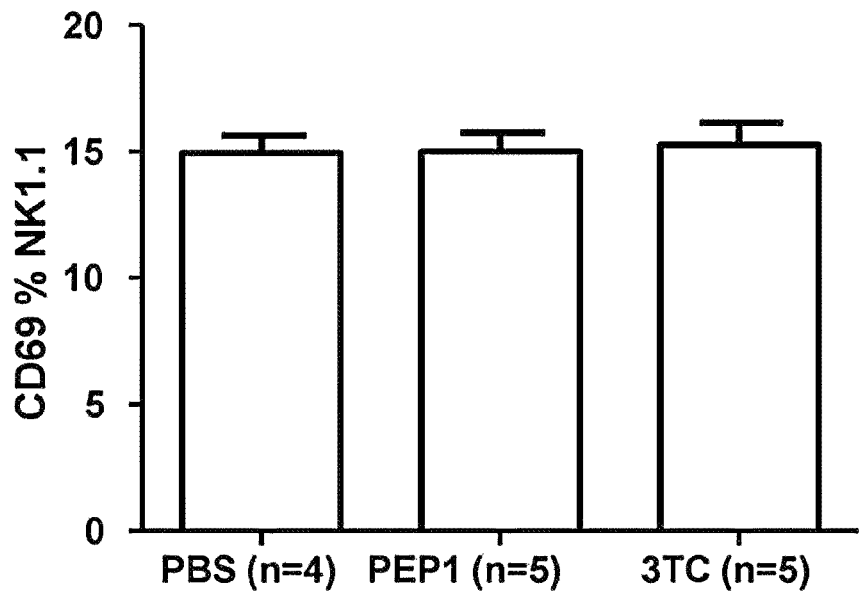

FIG. 52f shows the effect of the PEP1 peptide on activation of immunocytes (NK1.1) and INFγ.

Figure 52G:
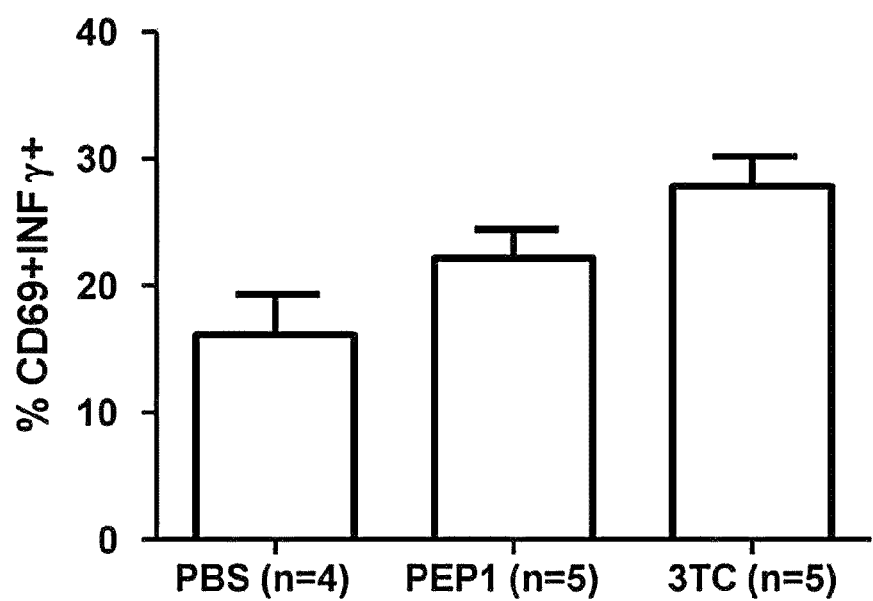

FIG. 52g shows the effect of the PEP1 peptide on activation of immunocytes (NK1.1) and INFγ.

FIG. 53 shows the effect of the PEP1 peptide on differentiation of macrophages in whole HBV W4P genome-transgenic mice.

Figure 54:
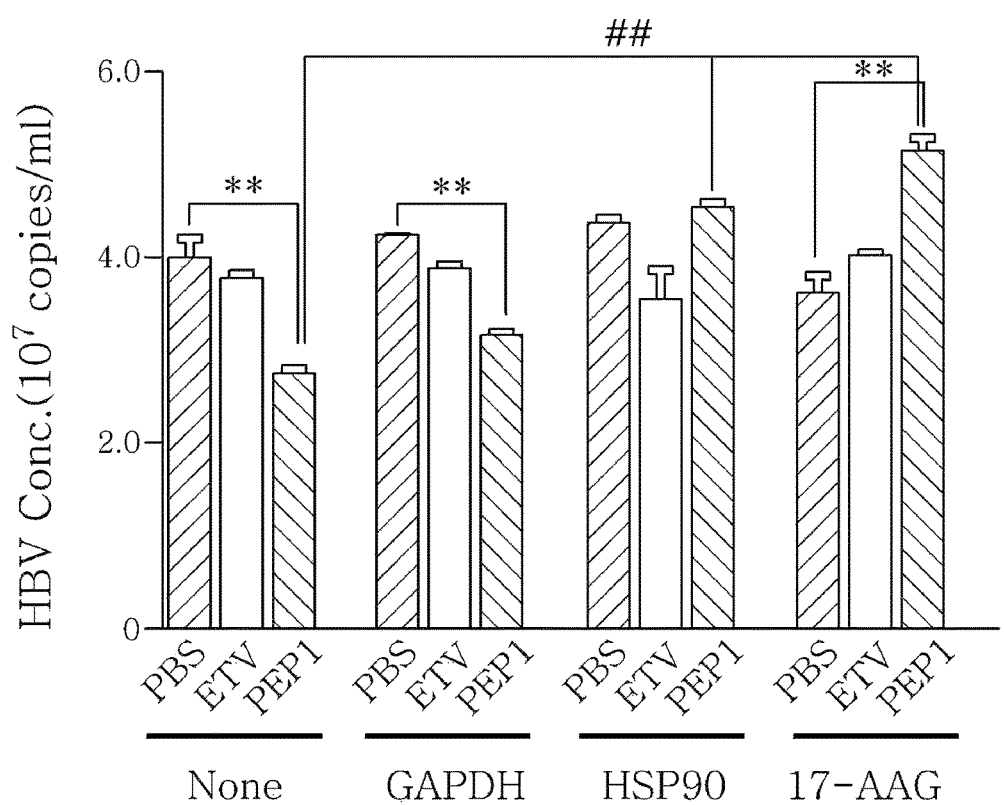

FIG. 54 shows an antiviral effect of the PEP1 peptide by HSP90 blocking in whole HBV wild-type genome-transgenic cells.

DETAILED DESCRIPTION OF THE INVENTION

Modes of the Invention

The present invention may be modified in various forms and have various embodiments, and thus will be described in detail based on the examples below. However, these examples are not provided to limit the present invention to specific embodiments, and it should be understood that the present invention can have various examples and applications as described in the claims, and comprises all modifications, equivalents and alternatives within the spirit and technical scope of the present invention. In the following description of the present invention, if it is determined that a detailed description of related art may obscure the gist of the present invention, the detailed description will be omitted.

A telomere, which is a repetitive genetic material located at each terminus of a chromosome, is known to prevent damage in a corresponding chromosome or coupling to a different chromosome. The telomere is gradually shortened with cell divisions, becoming very short after a certain number of cell divisions, and the cell eventually stops being divided and dies. On the other hand, the elongation of a telomere is known to extend the life span of a cell. As an example, it has been known that, in cancer cells, an enzyme called telomerase is overexpressed to prevent the shortening of telomeres, resulting in steady proliferation of the cancer cells, without death. The inventors confirmed that a peptide derived from a telomerase is effective in preventing and treating antiviral and virus-associated diseases, and thus the specification was completed.

An HSP90 protein is a molecular chaperone, which is in charge of stabilization of various proteins involved in cell growth, differentiation and survival, particularly, homeostasis under a stress environment. HSP90 is called "intracellular HSP90 (iHSP90)," which is present in cells, and also called "extracellular HSP90 (eHSP90)," which is present outside of cells. Interestingly, released HSP90 and cell surface HSP90 were observed in cancer cells, and these eHSP90 proteins stimulate cancer growth and angiogenesis. Cells, other than cancer cells, also produce eHSP90 under various environmental conditions, for example, heat, low oxygen, starvation and the presence of cytokines. As eHSP90 has a different function from iHSP90, and interacts with various cell-surface proteins, it can control a cell signaling pathway.

The inventors confirmed that HSP90 is associated with a variety of pathological conditions such as cancer, cirrhosis and viral infections. They confirmed that numerous proteins associated with carcinogenesis, invasiveness and metastasis are contained in HSP90-bindable molecules, and therefore, HSP90 is able to be a strong target as a cancer therapeutic agent.

In one aspect, the present invention suggests that an hTERT-derived 16mer peptide (611-EARPALLT-SRLRFIPK-626, SEQ ID NO: 1), known as the PEP1 peptide, interacts with HSP90 playing a critical role in protein homeostasis, and exhibits an antiviral effect by regulating cell signaling.

In another aspect of the present invention, the antiviral effect may be viral inhibition realized by one or more selected from viral replication inhibition, transcriptional inhibition, reactivation inhibition, antigen-expression inhibition, and virion-forming inhibition.

In one aspect, the present invention provides a telomerase reverse transcriptase-derived peptide vaccine. Specifically, in one aspect of the present invention, a human telomerase reverse transcriptase (hTERT)-derived amino acid peptide vaccine is provided. More specifically, in one aspect of the present invention, a peptide PEP1, which is a hTERT-derived 16-amino acid peptide, known as GV1001® is provided as an antiviral vaccine.

It was confirmed that the peptide (hereinafter, referred to as PEP1) according to an aspect of the present invention is a human telomerase-derived synthetic peptide, which is able to play various biological roles.

The inventors identified that PEP1 interacts with a heat shock protein (HSP) and regulates intracellular signaling. As shown in an aspect of the present invention, it was confirmed that HSP90 helps penetration of PEP1 into cells, and PEP1 interacts with eHSP and penetrates into the cytoplasm of the cells. This research shows that PEP1 can regulate an intracellular signaling pathway by interaction via HSP.

In another aspect, the present invention shows that the antioxidant effect of PEP1 is an effect of inhibiting the replication of HCV in HCV-infected cells with increased reactive oxygen species (ROS). Specifically, in one aspect of the present invention, it was identified that ROS is increased in HCV-infected cells, the increased ROS promoted HSP90 secretion, and cell penetration of PEP1 binding to HSP90 is improved to inhibit HCV replication and proliferation in the cells. In one aspect of the present invention, due to various biological activities of PEP1 exhibited via HSP90, a novel drug capable of inhibiting HCV replication and proliferation is provided.

In another aspect, the present invention provides a new type of peptide-based anti-HIV therapeutic agent capable of overcoming HIV resistance and drug side effects with respect to a conventional antiretroviral agent. It has been known that the cell death of infected cells inherently occurs because of the stimulation of an apoptotic mechanism. The inventors confirmed that PEP1 inhibits HIV multiplication exhibiting an antiviral effect on HIV by itself, and prevents cell death in the HIV-infected cell line. In one aspect of the present invention, it was confirmed that the cell condition is normally maintained, and HIV cytotoxicity or cell death is minimized.

In still another aspect of the present invention, a new type of anti-HBV therapeutic agent that is able to overcome drug side effects of conventional peptide-based viral hepatitis B drugs, such as hepatotoxicity and nephrotoxicity exhibited in continuous administration, is provided. The inventors provide a novel material for treating HCC by antiviral inhibition caused by the combined action of an anticancer effect caused by inhibition of a STAT3 signaling pathway using PEP1, direct cytotoxicity and IL-6 production inhibition and a hepatitis inhibitory effect.

In one aspect of the present invention, a peptide of SEQ ID NO: 1, a fragment of the peptide of SEQ ID NO: 1 or a peptide having at least 80% sequence homology with the peptide sequence comprises telomerase, specifically, a peptide derived from Homo sapiens telomerase.

In another aspect of the present invention, the peptide comprising an amino acid sequence of SEQ ID NO:1, the peptide having at least 80% sequence homology with the amino acid sequence, or a fragment thereof may be an antiviral peptide.

Peptides disclosed in the specification may include peptides having at least 80%, 85%, 90%, 95%, 96%, 97%, 98% and 99% sequence homologies. In addition, the peptides disclosed in the specification may include a peptide in which at least 1, 2, 3, 4, 5, 6 or 7 amino acids are different from the peptide of SEQ ID NO: 1 or fragments thereof.

In one aspect of the present invention, the peptide may be contained in the composition which is conjugated with a labeling material. According to another aspect, the labeling material may be a fluorescent material or a contrast medium. In another aspect of the present invention, the fluorescent material may be fluorescein isothiocyanate (FITC).

In one aspect of the present invention, the amino acid change has a property of changing physicochemical characteristics of the peptide. For example, amino acids may be changed to enhance thermal stability, change substrate specificity, and shift an optimal pH of the peptide.

The term "amino acid" used herein not only includes the 22 standard amino acids that are naturally integrated into a peptide, but also includes the D-isomers and transformed amino acids. Therefore, in one aspect of the present invention, the peptide may be a peptide including a D-amino acid. On the other hand, in another aspect of the present invention, the peptide may include a non-standard amino acid, which is subjected to post-translational modification. Examples of the post-translational modification include phosphorylation, glycosylation, acylation (including acetylation, myristorylation, and palmitoylation), alkylation, carboxylation, hydroxylation, glycation, biotinylation, ubiquitinylation, a change in chemical properties (e.g. β-removing deimidation, deamidation), and a structural change (e.g. formation of a disulfide bridge). The post-translational modification also includes changes of amino acids occurring due to chemical reactions during coupling with crosslinkers for formation of a peptide conjugate, for example, a change in an amino acid such as a change in an amino group, a carboxyl group, or a side chain.

The peptide disclosed herein may be a wild-type peptide identified and isolated from a natural source. Alternatively, the peptide disclosed in the specification may be an artificial variant comprising an amino acid sequence in which one or more amino acids are substituted, deleted, and/or inserted compared with the fragments of the peptide of SEQ. ID. NO: 1. The changing of amino acids in the wild-type polypeptide, as well as the artificial variant, includes substitutions of conservative amino acids, which do not have a significant influence on folding and/or activity of a protein. The conservative substitution may be carried out within the range of the group consisting of basic amino acids (arginine, lysine and histidine), acidic amino acids (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine and threonine). Generally, amino acid substitutions that do not change specific activities are known in the art. The most frequently-occurring exchange takes place between Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly, and vice versa. Other examples of the conservative substitution are shown in the following table.

TABLE 1

| Original amino acid | Exemplary residual substitution | Preferable residual substitution |
| --- | --- | --- |
| Ala (A) | val; leu; ile | Val |
| Arg (R) | lys; gln; asn | Lys |

TABLE 1-continued

| Original amino acid | Exemplary residual substitution | Preferable residual substitution |
|---|---|---|
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | Ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | Ala | Ala |
| Ser (S) | thr | Thr |
| Thr (T) | Ser | Ser |
| Trp (W) | tyr; phe | Tyr |
| Tyr (Y) | trp; phe; thr; ser | Phe |
| Val (V) | ile; leu; met; phe; ala; norleucine | Leu |

In terms of biological properties of the peptide, a substantial modification is performed by selecting a substitution part which has a considerably different effect in (a) maintaining the backbone structure, for example, a sheet- or helix-like three-dimensional structure, of the polypeptide in the substituted region, (b) maintaining charge or hydrophobicity of the molecule at a target site, or (c) maintaining the bulk of a side chain. Natural residues are classified into the following groups, based on general properties of the side chain:

(1) Hydrophobic: norleucine, met, ala, val, leu, ile;
(2) Neutral hydrophilic: cys, ser, thr;
(3) Acidic: asp, glu;
(4) Basic: asn, gln, his, lys, arg;
(5) Residues affecting chain orientation: gly, pro; and
(6) Aromatic: trp, tyr, phe.

Non-conservative substitutions may be performed by exchanging a member of one of the groups with that of another group. Any cysteine residue, which is not associated with maintaining the proper three-dimensional structure of the peptide, may typically be substituted with serine, thus increasing the oxidative stability of the molecule and preventing improper crosslinks, and, conversely, enhanced stability can be achieved by adding cysteine bond(s) to the peptide.

A different type of amino acid variant of the peptide is made by changing a glycosylation pattern of an antibody. The term "change" used herein refers to deletion of one or more carbohydrate residues that are found on the peptide and/or addition of one or more glycosylation sites which are not present in the peptide.

Glycosylation in peptides is typically N- or O-linked glycosylation. The term "N-linked glycosylation" used herein refers to attachment of carbohydrate residues to side chains of asparagine residues. As tripeptide sequences, asparagine-X-serine and asparagine-X-threonine (where the X is any amino acid, excluding proline) are recognition sequences for enzymatically attaching a carbohydrate residue to a side chain of an asparagine. Therefore, when one of these tripeptide sequences is present in a polypeptide, a potential glycosylation site is created. The "O-linked glycosylation" used herein refers to the attachment of one of the saccharides, for example, N-acetylgalactosamine, galactose, or xylose, to hydroxyamino acids and, most typically, to serine or threonine, but 5-hydroxyproline or 5-hydroxylysine may also be used.

Addition of a glycosylation site to the peptide is conveniently performed by changing the amino acid sequence so it contains the tripeptide sequence described above (for an N-linked glycosylation site). Such a change may be made by addition of one or more serine or threonine residues to the first antibody sequence or substitution of the first antibody sequence with one or more serine or threonine residues (for an O-linked glycosylation site).

In addition, the peptide comprising the sequence of SEQ ID NO: 1 according to one aspect of the present invention, the fragment of the peptide the sequence of SEQ ID NO: 1 or the peptide having at least 80% sequence homology with the peptide sequence has low intracellular toxicity and high in vivo stability. In one aspect of the present invention, SEQ ID NO: 1 represents a telomerase-derived peptide, which comprises 16 amino acids as will be described below.

Peptides set forth in SEQ ID NO: 1 are shown in Table 2 below. The "name" in Table 2 below is given to distinguish each peptide. In one aspect of the present invention, a peptide set forth in SEQ ID NO: 2 is the whole peptide of *Homo sapiens* telomerase. In another aspect of the present invention, the peptide comprising the sequence of SEQ ID NO: 1, the peptide of a fragment of the sequence of SEQ ID NO: 1 or the peptide having at least 80% sequence homology with the peptide sequence includes a "synthetic peptide" synthesized from a peptide present at a corresponding location of the peptides included in the telomerase. SEQ ID NO: 2 represents the full-length amino acid sequence of the telomerase.

TABLE 2

| SEQ. ID. NO: | Name | Location on telomerase | Sequence | Length |
|---|---|---|---|---|
| 1 | PEP1 | [611-626] | EARPALLTSRLRFIPK | 16 aa |
| 2 | | [1-1132] | MPRAPRCRAVRSLLRSHYREVLPLATFVRRL GPQGWRLVQRGDPAAFRALVAQCLVCVPW DARPPPAAPSFRQVSCLKELVARVLQRLCER GAKNVLAFGFALLDGARGGPPEAFTTSVRSY LPNTVTDALRGSGAWGLLLRRVGDDVLVHL LARCALFVLVAPSCAYQVCGPPLYQLGAAT QARPPPHASGPRRRLGCERAWNHSVREAGV PLGLPAPGARRRGGSASRSLPLPKRPRRGAAP EPERTPVGQGSWARPGRTRGPSDRGFCVVSP ARPAEEATSLEGALSGTRHSHPSVGRQHHAG PPSTSRPPRPWDTPCPPVYAETKHFLYSSGDK EQLRPSFLLSSLRPSLTGARRLVETIFLGSRPW | 1132 aa |

TABLE 2-continued

| SEQ. ID. NO: | Name | Location on telomerase | Sequence | Length |
|---|---|---|---|---|
| | | | MPGTPRRLPRLPQRYWQMRPLFLELLGNHA QCPYGVLLKTHCPLRAAVTPAAGVCAREKP QGSVAAPEEEDTDPRRLVQLLRQHSSPWQV YGFVRACLRRLVPPGLWGSRHNERRFLRNT KKFISLGKHAKLSLQELTWKMSVRDCAWLR RSPGVGCVPAAEHRLREEILAKFLHWLMSVY VVELLRSFFYVTETTFQKNRLFFYRKSVWSK LQSIGIRQHLKRVQLRELSEAEVRQHREARPA LLTSRLRFIPKPDGLRPIVNMDYVVGARTFRR EKRAERLTSRVKALFSVLNYERARRPGLLGA SVLGLDDIHRAWRTFVLRVRAQDPPPELYFV KVDVTGAYDTIPQDRLTEVIASIIKPQNTYCV RRYAVVQKAAHGHVRKAFKSHVSTLTDLQP YMRQFVAHLQETSPLRDAVVIEQSSSLNEAS SGLFDVFLRFMCHHAVRIRGKSYVQCQGIPQ GSILSTLLCSLCYGDMENKLFAGIRRDGLLLR LVDDFLLVTPHLTHAKTFLRTLVRGVPEYGC VVNLRKTVVNFPVEDEALGGTAFVQMPAHG LFPWCGLLLDTRTLEVQSDYSSYARTSIRASL TFNRGFKAGRNMRRKLFGVLRLKCHSLFLDL QVNSLQTVCTNIYKILLLQAYRFHACVLQLPF HQQVWKNPTFFLRVISDTASLCYSILKAKNA GMSLGAKGAAGPLPSEAVQWLCHQAFLLKL TRHRVTYVPLLGSLRTAQTQLSRKLPGTTLT ALEAAANPALPSDFKTILD | |

In one aspect of the present invention, a composition comprising the peptide comprising the amino acid sequence of SEQ ID NO: 1, the peptide having at least 80% sequence homology with the amino acid sequence or a fragment thereof, which is a peptide having an antiviral and virus-inhibitory effect, as an active ingredient, is provided. According to an aspect of the present invention, the composition may be a pharmaceutical composition.

According to an aspect of the present invention, the virus may be a DNA virus, an RNA virus, a double-stranded DNA reverse transcriptase (dsDNA-RT) virus, a single-stranded RNA reverse transcriptase (ssRNA-RT) virus, or an ssRNA virus.

According to another aspect of the present invention, the virus may be a member of the family Flaviviridae, Retroviridae, or Hepadnaviridae.

According to still another aspect of the present invention, the virus may be HCV, HIV, or HBV.

The pharmaceutical composition having an anti-viral and virus-inhibitory effect according to one aspect of the present invention may include the peptide comprising the amino acid sequence of SEQ ID NO: 1, the peptide having at least 80% sequence homology with the amino acid sequence or a fragment thereof at a content of 0.01 mg/mL or higher, 0.02 mg/mL or higher, 0.05 mg/mL or higher, 0.07 mg/mL or higher, 0.1 mg/mL or higher, 0.15 mg/mL or higher, 0.2 mg/mL or higher, 0.25 mg/mL or higher, 0.3 mg/mL or higher, 0.5 mg/mL or higher, 0.7 mg/mL or higher, 1 mg/mL or higher, 2 mg/mL or higher, 3 mg/mL or higher, 5 mg/mL or higher, 7 mg/mL or higher, 10 mg/mL or higher, 20 mg/mL or higher, 30 mg/mL or higher, 40 mg/mL or higher, 50 mg/mL or higher, 60 mg/mL or higher, 70 mg/mL or higher, 80 mg/mL or higher, or 90 mg/mL or higher, and 100 mg/mL or less, 90 mg/mL or less, 80 mg/mL or less, 70 mg/mL or less, 60 mg/mL or less, 50 mg/mL or less, 40 mg/mL or less, 30 mg/mL or less, 20 mg/mL or less, 10 mg/mL or less, 7 mg/mL or less, 5 mg/mL or less, 3 mg/mL or less, 2 mg/mL or less, 1 mg/mL or less, 0.7 mg/mL or less, 0.5 mg/mL or less, 0.3 mg/mL or less, 0.25 mg/mL or less, 0.2 mg/mL or less, 0.15 mg/mL or less, 0.1 mg/mL or less, 0.07 mg/mL or less, 0.05 mg/mL or less, or 0.02 mg/mL or less, but when there is a difference in effect according to the content, the content may be suitably regulated. When the peptide is included in the above range or less, the composition may be suitable for exhibiting a desired effect of the present invention, may satisfy both stability and safety of the composition, and may be suitable in terms of cost-effectiveness.

The composition according to one aspect of the present invention may include the peptide comprising the amino acid sequence of SEQ ID NO: 1, the peptide having at least 80% sequence homology with the amino acid sequence or a fragment thereof at a concentration of 0.0001 μM or higher, 0.001 μM or higher, 0.002 μM or higher, 0.005 μM or higher, 0.007 μM or higher, 0.01 μM or higher, 0.02 μM or higher, 0.05 μM or higher, 0.07 μM or higher, 0.09 μM or higher, 0.1 μM or higher, 0.2 μM or higher, 0.25 μM or higher, 0.3 μM or higher, 0.35 μM or higher, 0.4 μM or higher, 0.45 μM or higher, 0.5 μM or higher, 0.55 μM or higher, 0.6 μM or higher, 0.65 μM or higher, 0.7 μM or higher, 0.75 μM or higher, 0.8 μM or higher, 0.85 μM or higher, 0.9 μM or higher, 0.95 μM or higher, 1 μM or higher, 2 μM or higher, 3 μM or higher, 5 μM or higher, 7 μM or higher, 10 μM or higher, 30 μM or higher, 50 μM or higher, or 90 μM or higher, and 100 μM or less, 90 μM or less, 50 μM or less, 30 μM or less, 10 μM or less, 9 μM or less, 7 μM or less, 5 μM or less, 3 μM or less, 2 μM or less, 1 μM or less, 0.95 μM or less, 0.9 μM or less, 0.85 μM or less, 0.8 μM or less, 0.75 μM or less, 0.7 μM or less, 0.65 μM or less, 0.6 μM or less, 0.55 μM or less, 0.5 μM or less, 0.45 μM or less, 0.4 μM or less, 0.35 μM or less, 0.3 μM or less, 0.25 μM or less, 0.2 μM or less, 0.1 μM or less, 0.09 μM or less, 0.07 μM or less, 0.05 μM or less, 0.02 μM or less, 0.01 μM or less, 0.007 μM or less, 0.005 μM or less, 0.002 μM or less, 0.001 μM or less, or 0.0005 μM or less, and preferably 0.001 μM to 10 μM. When there is a difference in effect according to a concentration, the concentration may be suitably regulated. When the peptide is contained in the above range or less, the composition may be suitable for exhibiting a desired effect of the present invention, may satisfy both stability and safety of the composition, and may be suitable in terms of cost-effectiveness.

The composition according to an aspect of the present invention may be applied to all animals including a human, a dog, a chicken, a pig, a cow, a sheep, a guinea pig, and a monkey.

The composition according to an aspect of the present invention provides a pharmaceutical composition comprising the peptide comprising the amino acid sequence of SEQ ID NO: 1, the peptide having at least 80% sequence homology with the amino acid sequence or a fragment thereof as a peptide having an antiviral effect and an effect of preventing and treating a virus-related disease. The pharmaceutical composition according to one aspect of the present invention may be administered orally, rectally, transdermally, intravenously, intramuscularly, intraperitoneally, intramedullarly, epidurally or subcutaneously.

Forms for oral administration may be, but are not limited to, tablets, pills, soft or hard capsules, granules, powders, solutions, or emulsions. Forms of non-oral administration can be, but not limited to, injections, drips, lotions, ointments, gels, creams, suspensions, emulsions, suppositories, patches or sprays.

The pharmaceutical composition according to one aspect of the present invention may comprise, as needed, additives, such as diluents, excipients, lubricants, binders, disintegrants, buffers, dispersants, surfactants, coloring agents, aromatics, or sweeteners. The pharmaceutical composition according to one aspect of the present invention may be prepared by a conventional method in the art.

The active ingredient of the pharmaceutical composition according to an aspect of the present invention may vary according to the patient's age, sex, weight, pathological status and severity thereof, administration route, or a prescriber's judgment. Determination of the dosage based on such factors is within the level of those of ordinary skill in the art, and a daily dose of the composition may be 0.01 µg/kg/day or more, 0.1 µg/kg/day or more, 1 µg/kg/day or more, 0.0016 mg/kg/day or more, 0.005 mg/kg/day or more, 0.006 mg/kg/day or more, 0.0093 mg/kg/day or more, 0.01 mg/kg/day or more, 0.016 mg/kg/day or more, 0.05 mg/kg/day or more, 0.1 mg/kg/day or more, 0.5 mg/kg/day or more, 1 mg/kg/day or more, 5 mg/kg/day or more, 10 mg/kg/day or more, 50 mg/kg/day or more, 100 mg/kg/day or more, 1 g/kg/day or more, 5 g/kg/day or more, or 9 g/kg/day or more, and 10 g/kg/day or less, 9 g/kg/day or less, 5 g/kg/day or less, 1 g/kg/day or less, 100 mg/kg/day or less, 50 mg/kg/day or less, 10 mg/kg/day or less, 5 mg/kg/day or less, 1 mg/kg/day or less, 0.5 mg/kg/day or less, 0.1 mg/kg/day or less, 0.05 mg/kg/day or less, 0.017 mg/kg/day or less, 0.01 mg/kg/day or less, 0.0094 mg/kg/day or less, 0.007 mg/kg/day or less, 0.005 mg/kg/day or less, 0.0017 mg/kg/day or less, 1 µg/kg/day or less, 0.1 µg/kg/day or less, or 0.05 µg/kg/day or less. For example, the daily dose may be 0.01 µg/kg/day to 10 g/kg/day, specifically 0.1 µg/kg/day to 1 g/kg/day, more specifically 1 µg/kg/day to 0.1 g/kg/day, and further more specifically, 1 µg/kg/day to 10 mg/kg/day, or preferably 1 µg/kg/day to 1 mg/kg/day, more preferably 0.005 mg/kg to 0.05 mg/kg, and most preferably 0.01 mg/kg/day, and if there is a difference in effect depending on a dose, the dose may be properly adjusted. For an adult (60 kg), the composition may be administered daily at 0.1 mg to 1 mg, preferably, 0.4 mg to 0.6 mg, and most preferably 0.56 mg. The pharmaceutical composition according to an aspect of the present invention may be administered once to three times a day, but the present invention is not limited thereto.

In one aspect of the present invention, the composition is an antiviral composition for preventing and treating a virus-associated disease, which includes the peptide comprising the amino acid sequence of SEQ ID NO: 1, the peptide having at least 80% sequence homology with the amino acid sequence or a fragment thereof as an active ingredient.

The composition according to one aspect of the present invention may be formulated in the form of, for example, tablets, granules, a powder, a liquid, and a solid, but the present invention is not particularly limited thereto. Each form may be prepared without difficulty by those of ordinary skill in the art by mixing conventionally used components as well as the active ingredient according to the form or the purpose of use and may produce a synergistic effect in combination with other ingredients.

In another aspect of the present invention, the composition may be a food composition.

The food composition according to one aspect of the present invention may be formulated in the form of, for example, tablets, granules, a powder, a liquid, and a solid, but the present invention is not particularly limited thereto. Each form may be prepared without difficulty by those of ordinary skill in the art by mixing conventionally used components as well as the active ingredient according to the form or the purpose of use without difficulty and may produce a synergistic effect in combination with other ingredients.

In still another aspect of the present invention, a method for improving, preventing and treating a viral disease, which includes administering the composition to a subject having a viral disease or pathological symptoms caused by a virus, is provided.

According to an aspect of the present invention, the viral disease may be acquired immunodeficiency syndrome (AIDS), hepatitis B, hepatitis C, or liver cirrhosis or liver cancer caused thereby.

According to yet another aspect of the present invention, a kit for preventing and treating a viral disease, which comprises the composition; and instructions in which a method for preventing and treating a viral disease is described.

According to an aspect of the present invention, the method for preventing and treating a viral disease may comprise administering the composition to a subject having a viral disease or having pathological symptoms caused by a virus.

According to yet another aspect of the present invention, a use of the peptide comprising an amino acid sequence of SEQ ID NO:1, the peptide having at least 80% sequence homology with the amino acid sequence, or a fragment thereof for use in preparation of the composition is provided.

The terms used in the specification are intended to be used to describe specific embodiments, not to limit the present invention. Terms without numbers in front of nouns are not intended to limit quantity but are intended to represent the presence of at least one item cited herein. The terms "comprising," "having," "including" and "containing" should be interpreted openly (i.e. "including but not limited to").

Mentioning a numerical range easily replaces mentioning individual numbers within the range, and unless cited otherwise, each number is applied to the specification as individually mentioned in the specification. The end values of all the ranges are included in the range and can be combined independently.

All methods mentioned in the specification may be performed in suitable order unless noted otherwise or explicitly contradicted with the context. The use of any one embodiment and all embodiments, or exemplary language (e.g., "such as", "like~"), unless included in the claims, is used to more clearly describe the present invention, not to limit the scope of the present invention. Any language herein outside of the claims should not be interpreted as necessary for the present invention. Unless defined otherwise, technical and scientific terms used herein have meanings ordinarily understood by those of ordinary skill in the art to which the present invention belongs.

The exemplary embodiments of the present invention include the best mode known to the inventors to carry out the present invention. Variations in the exemplary embodiments can become clear to those skilled in the art when reading the descriptions above. The inventors expect those skilled in the art will suitably use such variations, and embody the present invention by methods different from those described in the specification. Thus, the present invention, as allowed by the patent law, includes equivalents and all modifications of the gist of the present invention mentioned in the accompanying claims. Moreover, all possible variations with any combination of the above-mentioned components are included in the present invention, unless explicitly stated otherwise or contradicted in the context. In one aspect of the present invention, although the present invention is described and shown by exemplary embodiments, those skilled in the art will readily understand that there can be various changes in the form and details without departing from the spirit and scope of the invention defined by the claims below.

Hereinafter, the configuration and effects of the present invention will be described in further detail with reference to examples and experimental examples. However, the following examples and experimental examples are merely provided to illustrate the present invention to help understand the present invention, and the scope of the present invention is not limited thereto.

Example 1

Synthesis of Peptide

The peptide of SEQ ID NO: 1 (hereinafter, referred to as "PEP1") was prepared according to a conventionally known method of solid phase peptide synthesis. Specifically, the peptide was synthesized by coupling each amino acid from the C-terminus through Fmoc solid phase peptide synthesis (SPPS) using ASP48S (Peptron, Inc., Daejeon, Korea). The used first amino acids at the C-terminus of the peptides and attached to the resin are as follows:

NH$_2$-Lys(Boc)-2-chloro-Trityl Resin
NH$_2$-Ala-2-chloro-Trityl Resin
NH$_2$-Arg(Pbf)-2-chloro-Trityl Resin In all amino acid ingredients used to synthesize the peptide, the N-term was protected with Fmoc, and the residues were protected with Trt, Boc, t-butylester (t-Bu), and 2,2,4,6,7-pentamethyl dihydro-benzofuran-5-sulfonyl (Pbf) which can be removed from an acid. Examples of the amino acids are as follows:

Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser(tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(Trt)-OH, Fmoc-Tyr(tBu)-OH, Fmoc-Ahx-OH, Trt-Mercaptoacetic acid.

As coupling reagents, 2-(1H-Benzotriazole-1-yl)-1,1,3,3-tetamethylaminium hexafluorophosphate (HBTU)/N-Hydroxybenzotriazole (HOBt)/4-Methylmorpholine (NMM) were used. Fmoc deprotection was carried out using piperidine in 20% DMF. To isolate the synthesized peptide from the resin and remove the protective group of the residue, a cleavage cocktail [trifluoroacetic acid (TFA)/triisopropylsilane (TIS)/ethanedithiol (EDT)/H$_2$O=92.5/2.5/2.5/2.5] was used.

Each peptide was synthesized by a repeated process of reacting each of corresponding amino acids with the starting amino acid protected by the amino acid protective group while binding to a solid phase scaffold, washing the resulting product with a solvent, and performing deprotection. After being cleaved from the resin, the synthesized peptide was purified by HPLC, synthesis was validated by mass spectrometry (MS), and lyophilized.

The purity of all peptides used in the embodiment was 95% or higher by high-performance liquid chromatography.

A specific process for preparing the peptide PEP1 according to the present invention will be described as follows.

1) Coupling

The amino acid (8 equivalents) protected with NH$_2$-Lys(Boc)-2-chloro-trityl resin, and a coupling reagent [HBTU (8 equivalents)/HOBt (8 equivalents)/NMM (16 equivalents)] dissolved in DMF were mixed together and incubated for 2 hours at room temperature. The resulting product was sequentially washed with DMF, MeOH and DMF.

2) Fmoc deprotection

Piperidine in 20% DMF was added to the resulting product, and the mixture was reacted twice for 5 minutes at room temperature and then sequentially washed with DMF, MeOH and DMF.

3) The peptide backbone [NH$_2$-E(OtBu)-A-R(Pbf)-P-A-L-L-T(tBu)-S(tBu)-R(Pbf)L-R(Pbf)-F-I-P-K(Boc)-2-chloro-Trityl Resin] (SEQ ID NO: 11) was prepared by repeating reactions 1 and 2.

4) Cleavage: The peptide was isolated from the completely-synthesized resin by adding a cleavage cocktail to the resin.

5) After adding cooled diethyl ether to the obtained mixture, a peptide obtained by centrifugation was precipitated.

6) Following purification by Prep-HPLC, a resulting product was analyzed by LC/MS to identify a molecular weight, and lyophilized to prepare a powder.

Example 2

Confirmation of Effect of PEP1 on HCV

Culture of Cell Line

A cell line used in the example relating to the HCV antiviral effect of PEP1 according to an aspect of the present invention, such as, human hepatocellular carcinoma (Huh7.5) was purchased from the American Type Culture Collection (ATCC; Manassas, Va., USA), and a JFH-1 cell line was constructed using HCV2a JFH-1 clones provided from Dr. Wakita (Tokyo Metropolitan Institute for Neuroscience, Tokyo, Japan) in the Huh7.5 cell line. All of the cell lines were cultured in a Dulbecco's modified Eagle's medium (DMEM) containing 10% FBS and 1% antibiotics.

Reagents and Antibodies

Reagents used in the example according to an aspect of the present invention included N-acetylcysteine (NAC), pyrolidine dithiocarbamate (PDTC), vitamin E, hydrogen peroxide (H$_2$O$_2$), methyl-β-cyclodextrin (MbCD), KNK-437 (as KNK, HSP70 inhibitor), and 17-N-Allylamino-17- demethoxy geldanamycin (17AAG, HSP90 inhibitor), which were purchased from Sigma-Aldrich (St. Louis, Mo., USA) and Calbiochem (Temecula, Calif., USA).

Antibodies used in the example according to an aspect of the present invention were HSP70, HSP90, and isotype control antibodies, which were purchased from Santa Cruz Biotechnology (Santa Cruz, Calif., USA). Anti-LRP1 antibodies were purchased from Thermo Fisher Scientific (Fremont, Calif., USA).

Measurement of Intracellular ROS

One day after $5 \times 10^4$ (cells/well) cells of the JFH-1 cell line were seeded into a 24-well plate, intracellular ROS production was measured according to various experimental materials. Measurement of intracellular activity was carried out by staining the cells with dichlorodihydrofluoresein diacetate (DCF-DA; Invitrogen), and fluorescence measurement of ROS production was carried out at 485 nm (emission)/535 nm (excitation) using Infinte M2000 Tecan (Tecan Trading AG, Switzerland). All fluorescent units were expressed as arbitrary units, and as a positive control group, hydrogen peroxide ($H_2O_2$, 2 mM) was used. ROS measurement for the Huh7.5 cells was also carried out by the same procedure as described above.

Immunoblotting

Proteins were acquired from cells using a lysis solution (Cell Signaling Technology, Danvers, Mass., USA) containing a proteinase inhibitors cocktail (Roche, Basel, Switzerland) and a phosphatase inhibitor (Roche). To remove debris, which remained after cell lysis, the cells were centrifuged for 10 minutes at 4° C. 50 µg of the proteins were analyzed through 12% sodium dodecyl sulfate-polyacrylamide gel electrophoresis (SDS-PAGE), and then transferred to a polyvinylidene difluoride membrane (PVDF; Millipore, Bedford, Mass., USA). The transferred membrane was developed using an ImageQuant™ LAS 4000 mini biomolecular imager (GE Healthcare Bio-Sciences AB, Sweden), after antibodies against HSP90, p38, p-p38 (Thr180/Tyr182), JNK, p-JNK (Thr183/Tyr185), ERK, p-ERK (Thr202/Tyr204), and zinc-copper containing enzyme SOD (CuZn-SOD) and manganese-SOD (Mn-SOD) as superoxide dismutase oxidases (SODs), and GAPDH (all of them were purchased from Cell Signaling Technology and Santa Cruz Biotechnology) were attached to the membrane and then visualized by a SuperSignal West Pico chemiluminescence substrate (Pierce, Rockford, USA). β-actin was used for normalization using a Multi Gauge V 3.0 (Fuji Film, Japan), and quantitative analysis was carried out by densitometry.

For immunoprecipitation, 400 µg of a cell lysate was pre-washed with a protein A/G plus-agarose bead immunoprecipitant (Santa Cruz Biotechnology) for two hours and then centrifuged, followed by removing the beads. The supernatant was cultured with 4 µg of related antibodies, 20 µl of beads and a lysis buffer overnight at 4° C. The immunoprecipitation was prepared for immunoblotting of anti-HSP90 (Cell Signaling Technology) antibodies and FKBP8 (Thermo Fisher Scientific).

Transient Knockdown Using LRP1/CD91siRNA

A low-density lipoprotein receptor-related protein 1 (LRP1)/CD91 (that is, LRP1) is a protein that promotes migration of epidermal and dermal cells, and has been identified as one of the HSP receptors. LRP1 is a receptor for gp96, HSP90, HSP70 and calrecticulin, and a peptide chaperoned by HSPs was bound to the receptor, and entered into antigen-presenting cells along with the HSPs. An eHSP90-binding LRP1 complex is presented as a receptor in endocytosis and signaling. This shows that LRP1 has an influence on the role of eHSP under a physiological or stress environment. It has been known that the endocytosis of peptide PEP1 according to an aspect of the present invention is dependent on eHSP, and the eHSP is accommodated by the LRP1 receptor. The inventors suggested that LRP1 is important in antioxidant activity of the peptide PEP1 according to the present invention under an oxidative stress environment. The inventors showed that LRP1 plays a critical role in the inhibition of the endocytosis of the peptide of the present invention and ROS production in the JFH-1 cells. To confirm this, LRP1 activity was inhibited using small interfering RNAs (siRNAs) for antibodies and LRP1.

siRNA-targeted LRP1 and scramble siRNA were purchased from Bioneer (Daej eon, Republic of Korea). All siRNAs were injected into the JFH-1 or Huh7.5 cell line using Lipofectamine 2000 (Invitrogen) according to various concentrations. After 18 hours, RNAs are obtained from the cells, and then a quantitative reverse-transcription-polymerase chain reaction (qRT-PCR) was carried out to confirm RNA knockdown.

Quantitative Measurement of HCV RNA

A HCV RNA level was detected though quantitative PCR using primers for a NS2 gene. To measure the level of HCV RNA in the supernatant of cell culture, RNA was extracted from 100 µl of the cell culture using a QIAamp Viral RNA Mini kit (Qiagen). The extracted RNA was used in cDNA synthesis using a transcript first strand cDNA synthesis supermix kit (Roche Applied Science). PCR was carried out using a 1×SYBR Green mix (Qiagen). For real-time PCR, an NS2 forward primer 5'-CGACCAGTACCACCATCCTT-3' (SEQ ID NO: 3) and a reverse primer 5'-AGCACCT-TACCCAGGCCTAT-3' (SEQ ID NO: 4) were purchased from Bioneer Co. For quantitative PCR, a 7900HT Fast real-time PCR system (Applied Biosystems, Foster City, Calif., USA) was used.

Flow Cytometric Analysis

To assess the intracellular penetration of fluorescein isothiocyanate (FITC)-conjugated PEP1, the cell lines were treated with various materials, and further treated with the FITC-conjugated PEP1 for two hours, followed by FACS analysis. For LRP1 knockdown, 18 hours after siRNA was injected, the cells were washed with PBS and treated with FITC-conjugated PEP1 for two hours, peptides attached to the cells were completely removed by treatment with trypsin/EDTA (Invitrogen), and the cells were washed with an FACS buffer solution (PBS, 0.5% BSA), followed by analysis using BD FACS Fortessa (BD Biosciences, San Diego, Calif., USA). Data analysis was carried out using FlowJo software (version 9.7.7, TreeStar, Ashland, Oreg., USA).

HSP90 Detection Using ELISA

The Huh7.5 and JFH-1 cell lines were treated with an oxidant ($H_2O_2$, 2 mM) and an antioxidant, PDTC (100 µM), for two hours. HSP90 (extracellular HSP90, eHSP90) in the supernatant of a culture was detected by ELISA (R&D Systems, Minneapolis, Minn., USA) according to the manufacturer's instructions.

Immunofluorescence and Detection of Liver Tissue and JFH-1 Cells

Human liver biopsy tissue samples were obtained from chronic HCV or HBV patients and autoimmune hepatitis (AIH) patients as a control group, under the supervision of the Institutional Review Board (IRB) of Soonchunhyang University Hospital in Bucheon (2014-12-034) and Seoul National University Hospital (1410-136-621). To evaluate the HSP90 expression in liver cells and JFH-1 cells, liver tissue or JFH-1 cells were stained with anti-HSP90 antibodies (Cell Signaling Technology). To visualize the tissue or cells, Alexa Fluor 594-conjugated anti-rabbit IgG (Invitrogen) was used. For counterstaining of the cell nucleus, 4',6-diamino-2-phenylindole (DAPI, Sigma-Aldrich) was used. Images were obtained and processed using a confocal microscope system A1 (Nikon, Minatoku, Tokyo, Japan) and an NIS-elements 4.20 viewer (Nikon).

Statistical Analysis

All data is expressed as means±SEM, and a two-tailed Student's t-test was performed for statistical comparison using GraphPad Prism, version 5.01 (GraphPad, La Jolla, Calif., USA). When a P value was 0.05 or less, it was considered statistically significant.

Analysis of Experimental Results

1) Inhibitory Effect of PEP1 on Replication of HCV RNA

It has been widely known that suitable levels of ROS regulate replication of HCV, HBV and HIV. For this reason, the inventors conducted experiments to examine whether PEP1 exhibits an inhibitory effect on replication of HCV RNA in the JFH-1 cells on the assumption that the effect of PEP1 on ROS inhibition has an influence on inhibition of viral replication.

According to the methods described in the experiments and the analysis methods, to investigate whether PEP1 inhibits the replication of one HCV RNA such as NS2, the transcript of NS2 was measured. When the transcripts of NS2 were measured for a control group (vehicle), a PEP1-treated group, conventional antioxidant (NAC, PDTC, and vitamin E)-treated groups in the JFH-1 cells, compared to the control group, it was seen that PEP1 concentration-dependently inhibits the NS2 transcription until 10 µM. In contrast, it was seen that the conventional antioxidants NAC, PDTC and vitamin E do not inhibit the NS2 transcription at all (FIG. 16).

Based on PEP1 exhibiting an effect of HSP90-dependent reduction of ROS activity, an experiment was performed to examine whether the inhibitory effect on HCV RNA replication is also associated with HSP90. Compared to a control group (PBS), degrees of inhibiting the NS2 transcripts by PEP1 were measured by classifying the JFH-1 cells into a control antibody group (isotype), an anti-HSP70-treated group and an anti-HSP90-treated group. The HCV RNA proliferation by PEP1 was not inhibited by the treatment with anti-HSP90 antibodies. However, in the case of the anti-HSP70 antibodies and the control antibody group, HCV RNA replication was inhibited by PEP1 regardless of antibodies (FIG. 17). In addition, degrees of inhibiting the NS2 transcript by PEP1 were measured according to whether the HSP90 receptor LRP1 was inhibited or not. When LRP1 expression was knocked down due to the treatment with LRP1 siRNA, HCV RNA replication in the JFH-1 cells was not decreased by PEP1 (FIG. 18).

It has been known that HSP90 is involved in forming a complex of NS5A and FKBP8 for HCV RNA replication. Therefore, it was investigated if the inhibition of the HCV RNA replication by PEP1 is caused by the inhibition of the formation of a replication complex. The binding between HSP90 and FKBP8 was observed by treating the JFH-1 cells with PEP1. Specifically, the JFH-1 cells were cultured with PEP1 (10 µM) for 48 hours. Afterward, the proteins were subjected to immunoprecipitation with anti-FKBP8 antibodies or anti-HSP90 antibodies. Endogenous expression of HSP90 and FKBP8 was detected in untreated JFH-1 cells.

As a result, compared to the control group, when PEP1 was treated, co-precipitation of HSP90 by FKBP8 was reduced (FIG. 19). As a result of anti-HSP90 and anti-FKBP8 immunoprecipitation and immunoblotting with anti-HSP90 and anti-FKBP8 antibodies for the JFH-1 cells after being divided into a cell lysate, a control group (PBS) and a PEP1-treated group, it was analyzed that, according to the anti-HSP90 immunoprecipitation, FKBP8 expression was reduced in the PEP1-treated group, and according to anti-FKBP8 immunoprecipitation, HSP90 expression was reduced in the PEP1-treated group through immunoblotting with antibodies (FIG. 19). Such a result shows that PEP1 directly inhibits the formation of an HCV RCV replication complex, and PEP1 binds to the major part of HSP90 that interacts with FKBP8.

From the above-described experimental result, it can be noted that PEP1 is likely to be bound with HSP90, and therefore the replication of HCV RNA is inhibited via a mechanism of reducing the activity of HSP90 against FKBP8. It can be seen that PEP1 inhibits HCV replication, and exhibits an antiviral effect.

2) Inhibition of ROS Production by PEP1

Figure 1:
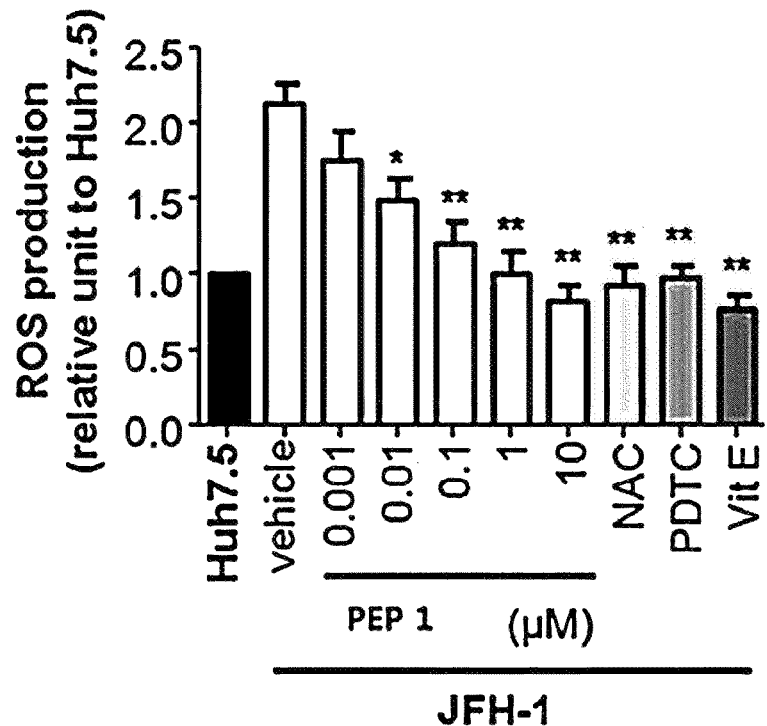
FIG. 1 is a graph of a degree of ROS production when JFH-1 cell lines are incubated with a vehicle, conventional antioxidants (NAC (20 mM), PDTC (100 μM), vitamin E (10 μM)) and different concentrations of PEP1, respectively, for 2 hours.

To investigate an effect of PEP1 on inhibiting ROS production in virus-infected cells, inhibition of ROS production when PEP1 was administered to an HCV-infected cell line such as JFH-1 cells was comparatively examined. The JFH-1 cell line was produced by infecting Huh7.5 cells with HCV2a JFH-1 clones. Due to HCV virion synthesis, an intracellular ROS level in the JFH-1 cell line is regulated to a higher level than in the Huh7.5 cell line (parent cell line of JFH-1). The inventors confirmed the fact that PEP1 considerably and dose-dependently inhibits ROS production in the JFH-1 cells up to 10 µM. At 1 and 10 µM, the antioxidant activity of PEP1 equaled NAC, PDTC and vitamin E (FIG. 1).

According to the methods described in the experiments and analyses, ROS were detected in the JFH-1 cells and the Huh7.5 cells. After PEP1 was treated for two hours at various concentrations, the cells were stained with DCF-DA for 30 minutes and then fluorescence was detected. As a control group, a human HCC cell line, and Huh7.5 and JFH-1 cell lines were treated with known representative antioxidants such as NAC (2 Mm), PDTC (100 µM), and vitamin E (10 µM) and then compared. When PEP1 was not administered, intracellular ROS levels in the JFH-1 cell line approximately more than doubled from those in the Huh7.5 cell line (FIG. 1). The ROS levels were concentration-dependently decreased with treatment with PEP1. According to the comparison between the experimental groups in which the JFH-1 cells were treated with different concentrations (0.001, 0.01, 0.1, 1, 10 µM) of PEP1 and the experimental groups in which conventional antioxidants (NAC, PDTC and vitamin E) were treated, respectively, and the control group (treated with a vehicle), PEP1 concentration-dependently reduced ROS production, and the conventional antioxidants also induced a decrease in ROS production (FIG. 1).

Figure 2:
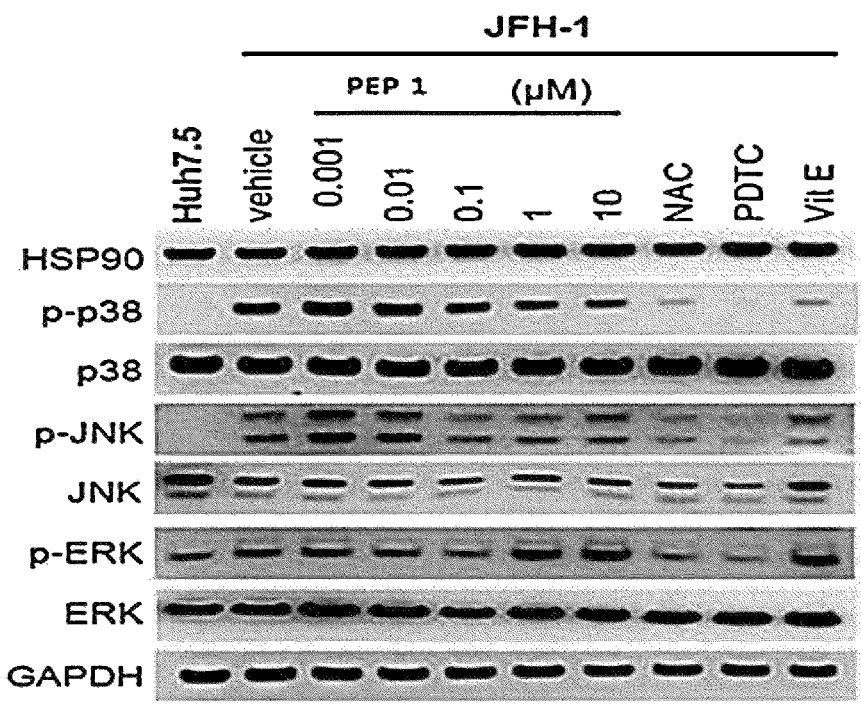
FIG. 2 is an image showing immunoblotting analysis for JFH-1 cell lines using antibodies specific to HSP90, p-p-38, p38, p-JNK, JNK, p-ERK, ERK, and GAPDH after treatment with a vehicle, PEP1, NAC (20 mM), PDTC (100 μM) and vitamin E (10 μM) for 2 hours.

Since ROS is known to induce the activation of a MAPK signaling pathway, experiments were carried out to investigate whether PEP1 is involved in reducing MAPK signaling pathway-associated factors (p38, JNK and ERK) (FIG. 2). According to the methods described in the experiments and analyses, immunoblotting for the JFH-1 cells and the Huh7.5 cells were carried out. Phosphorylation of p38 and JNK was decreased in the JFH-1 cells after PEP1 treatment, which is a result similar to that obtained when the antioxidants such as NAC, PDTC and vitamin E were treated. However, ERK activity was increased with the treatment with both of PEP1 and vitamin E (FIG. 2).

In addition, in the JFH-1 cells and the Huh7.5 cells, all of the control group and the experimental groups showed high expression of HSP90 (FIG. 2).

From the above-mentioned experimental results, it can be seen that the treatment with PEP1 can bring about a decrease in ROS production in cells, which is caused via specific signaling in the JFH-1 cells, that is, reduced MAPK signaling. FIGS. 1 to 9 show that PEP1 inhibits the ROS production in the JFH-1 cells via HSP90.

3) Role of eHSP90 in Antioxidant Effect of PEP1

The inventors assumed that the antioxidant effect of PEP1 is mediated by HSP90. In the present invention, to investigate whether the antioxidant effect of PEP1 is induced by HSP90, an experiment of assessing a degree of ROS production by PEP1 depending on the activation of HSP90 was carried out. The inventors inhibited the interaction with HSP90 by two methods: a use of antibodies against HSP70 and antibodies against HSP90 or a use of an inhibitor occupying a catalytic position (ATP-binding pocket in the N-terminal of HSP90). According to the methods described in the experiments and analyses, ROS production in the JFH-1 cells was compared between the PEP1-treated group, the antioxidant PDTC-treated group, and the control group (PBS).

Figure 3:
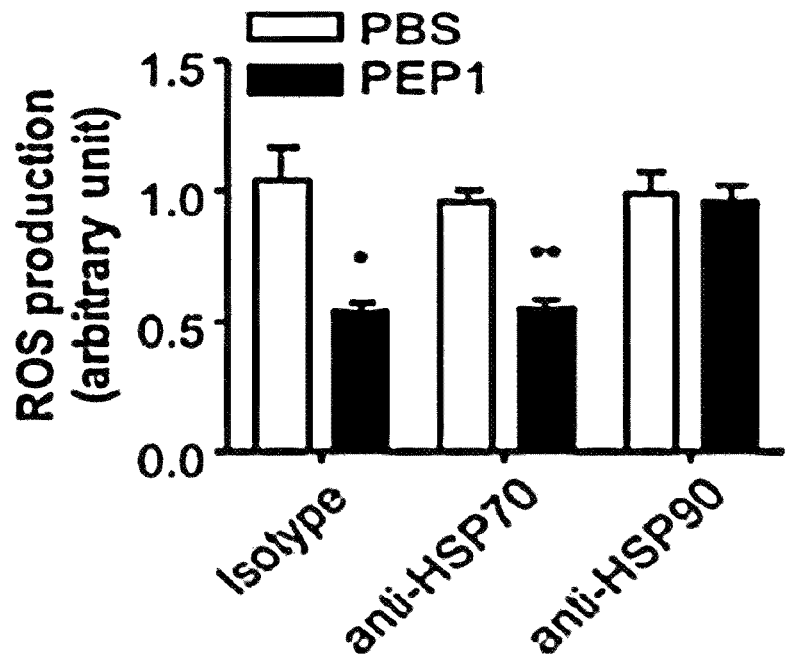
FIG. 3 is a graph showing ratios of ROS production when PEP1 is administered to JFH-1 cell lines after treatment with control antibodies (isotype), anti-HSP70 antibodies and anti-HSP90 antibodies, respectively, compared to a control group (DMSO, vehicle).
Figure 4:
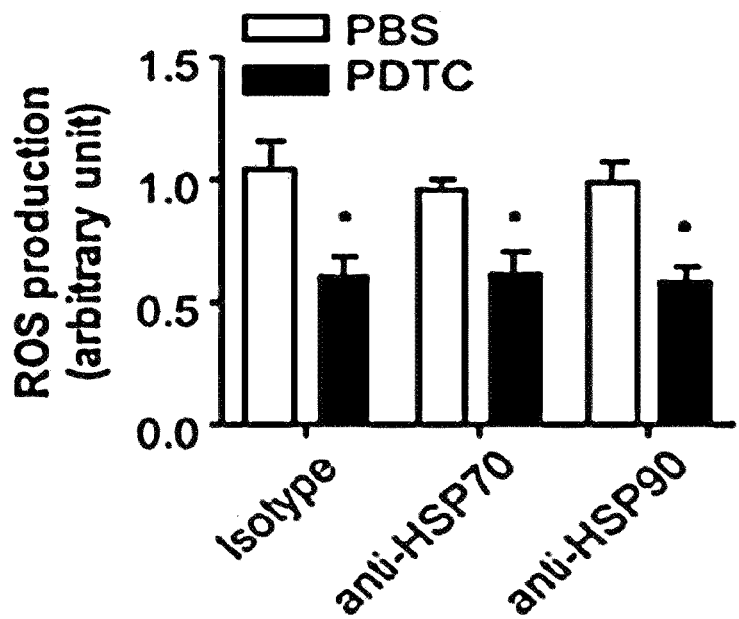
FIG. 4 is a graph showing ratios of ROS production when an antioxidant PDTC is administered to JFH-1 cell lines after treatment with control antibodies (isotype), anti-HSP70 antibodies, and anti-HSP90 antibodies, respectively, compared to a control group (DMSO, vehicle).
Figure 5:
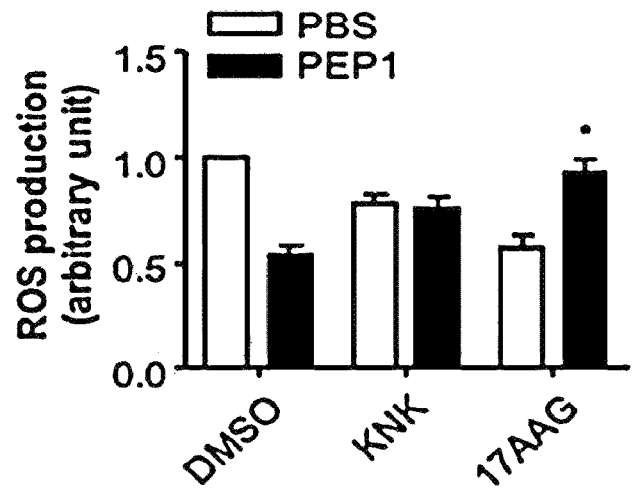
FIG. 5 is a graph showing ratios of ROS production when PEP1 is administered to JFH-1 cell lines after treatment with a control group (DMSO, vehicle), HSP70 inhibitor KNK (10 μM), and HSP90 inhibitor 17AAG (1 μM), respectively, compared to a control group (PBS).
Figure 6:
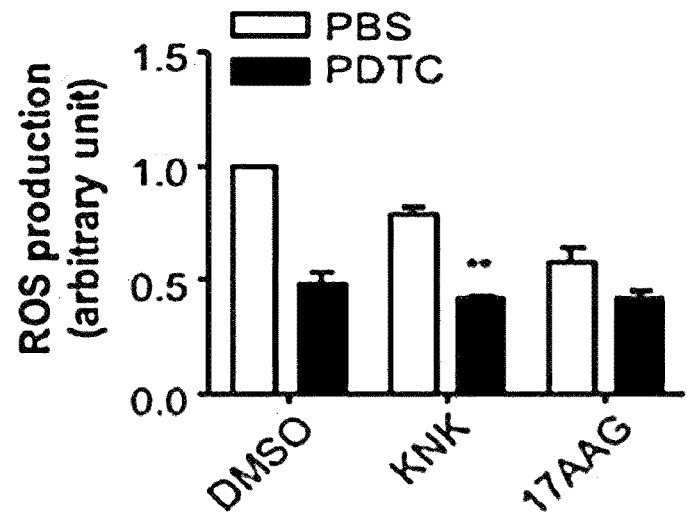
FIG. 6 is a graph showing ratios of ROS production when an antioxidant PDTC is administered to JFH-1 cell lines after treatment with a control group (DMSO, vehicle), HSP70 inhibitor KNK (10 μM), and HSP90 inhibitor 17AAG (1 μM), respectively, compared to a control group (PBS).

As a result, the present invention showed that PEP1 had an inhibitory effect on ROS levels in the JFH-1 cells in the presence of anti-HSP70 antibodies, but did not have such an effect in the presence of anti-HSP90 antibodies (FIG. 3). In the control antibodies (isotype), inhibition caused by PEP1 was observed (FIG. 3). In addition, when the JFH-1 cells were treated with the HSP90 inhibitor 17AAG, the ROS inhibitory effect was exhibited, but a change in ROS caused by the HSP70 inhibitor KNK was not observed (FIG. 5). The control drug PDTC inhibits ROS production regardless of blocking of HSP70 and HSP90 with specific antibodies, and inhibits ROS production under all treatment conditions (FIG. 4). In addition, PDTC inhibits ROS production in the presence of both of KNK and 17AAG (FIG. 6). This suggests that PEP1 inhibits ROS production through a different mechanism. Such data shows that eHSP90 is an important mediator for antioxidant activity of PEP1, and PEP1 acts on the catalytic position in HSP90, required for ROS induction.

Figure 7:
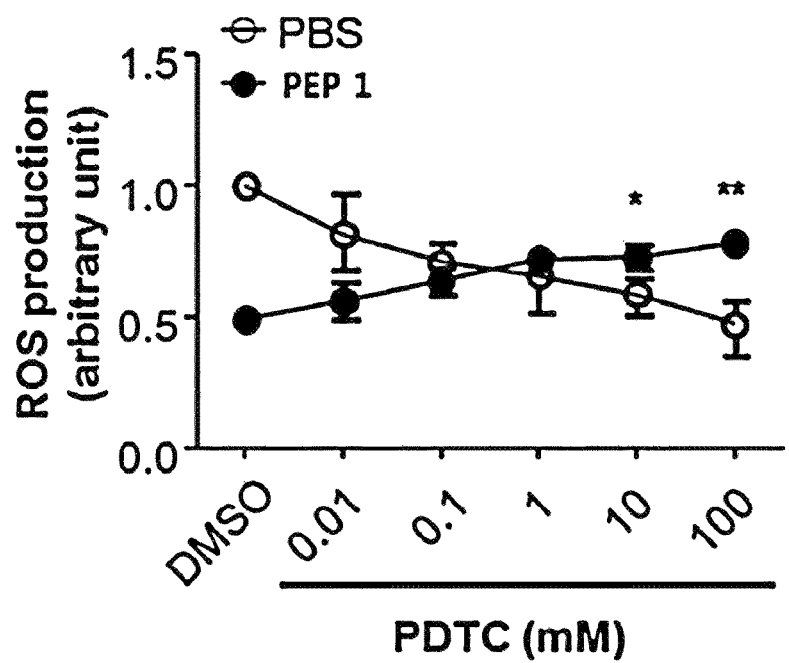
FIG. 7 is a graph showing ratios of ROS production when a JFH-1 cell line is incubated with PEP1 and DMSO, or cultured for two hours with an increasing PDTC concentration.

From the result that the antioxidant effect is decreased when 17AAG was treated, the inventors investigated the possibility in which PEP1 does not inhibit ROS in cells when the ROS levels in cells are too low or in the normal range. This suggests the possibility in which PEP1 may not inhibit ROS production in the JFH-1 cells under the circumstances in which an antioxidant is previously present. To investigate such hypothesis, the inventors treated cells with increasing concentrations of the antioxidant PDTC. As a result, it was confirmed that the antioxidant activity of PEP1 is gradually decreased (FIG. 7). This is because the ROS levels are decreased by the treatment with PDTC in the JFH-1 cells, and suggests that PEP1 selectively acts as an antioxidant in cells under an oxidative stress environment compared with those having ROS at reduced or normal levels. Such a characteristic of PEP1 contributes to the development of a therapeutic drug customized for oxidation levels.

Figure 8:
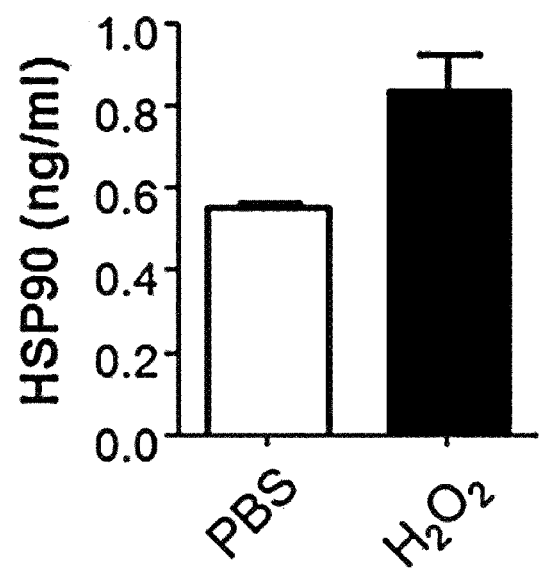
FIG. 8 is a graph showing expression levels (ng/ml) of HSP90 when a Huh7.5 cell line is treated with a type of ROS such as hydrogen peroxide, compared to treatment with a control group (PBS) through ELISA.

Moreover, in the present invention, an experiment was performed to identify a specific antioxidant function of PEP1 in a stress condition due to ROS. Specifically, an experiment was performed to confirm that the administration of a conventional antioxidant leads to a decrease in HSP90 expression, and thus PEP1 has a reduced antioxidative effect when administered with the conventional antioxidant. Since the antioxidative activity of PEP1 is dependent on eHSP90, in the example of the present invention, eHSP secretion from cells was assessed. The stimulation of Huh7.5 cells by H2O2 increased the eHSP90 secretion to a much higher level than the control group (FIG. 8). Meanwhile, when the JFH-1 cells are treated with the antioxidant PDTC, eHSP90 was produced at a lower level than the control group (FIG. 9). Such a result suggests that oxidative stress induces the HSP90 secretion. It is also shown that PEP1 selectively inhibits ROS production in the cells under oxidative stress.

FIGS. 1 to 9 shows that PEP1 inhibits ROS production in the JFH-1 cells via HSP90.

FIGS. 10 to 15 show that eHSP90 and LRP1 are essential for ROS production by PEP1.

4) Role of LRP1 in Antioxidative Effect by PEP1

It has been known that PEP1 enters into the cells in combination with eHSP90, and eHSP90 is accommodated in the cell receptor LRP1. LRP1 is a common receptor for gp96, HSP90, HSP70 and calreticulin, and peptides chaperoned by HSP are bound to these receptors, thereby entering antigen-presenting cells with HSP. An LRP1 complex is coupled with eHSP and acts as an endocytosis and cycling receptor, and it is suggested that LRP1 affects the action of eHSP90 under a pathological or stress condition. Moreover, HSP90 forms a HCV RNA replication complex with FKBP8, which is one of the FK506-binding protein families, and hepatitis C non-structural protein 5A (NS5A). Such a fact suggests that HSP90 can control HCV RNA replication by the expression or activation thereof. HSP90 regulates NOX activity, thereby inducing formation of superoxides. The inventors found that PEP1 binds to the main position of HSP90 to achieve a selective antioxidant action through a method of inhibiting the HSP90 activity, and has a variety of biological influences on cells under oxidative stress.

The inventors assumed that LRP1 under oxidative stress plays a critical role in the antioxidant effect of PEP1. The inventors assumed that, when LRP1 is absent, PEP1 does not enter cells, and therefore cannot inhibit ROS production in the JFH-1 cells.

To prove this, according to the methods described in the experiments and analyses, it was investigated how much PEP1 enters the cells depending on the presence or absence of LRP1, which is the cell receptor of the HSP90. Specifically, the LRP1 activity was inhibited using antibodies against LRP1 and siRNA, and flow cytometry was performed using FITC-conjugated PEP1.

FIGS. 10 to 15 show that eHSP90 and LRP1 are essential for ROS production by PEP1.

First, it was confirmed that, when pre-treated with MbCD, which is a lipid raft-forming inhibitor for inhibiting clathrin-caveolin-, and clathrin/caveolin-dependent entocyto pathways, PEP1 cannot enter JFH-1 cells. As reported previously, MbCD inhibits the entry of FITC-PEP1 into the JFH-1 cells, which is proven by a decreased fluorescence intensity compared with the PBS control group. The entocytosis of FITC-PEP1 was inhibited by LRP1 siRNA as well as anti-LRP1 antibodies, compared with the control group (FIGS. 11 and 12). This shows that LRP1 is a critical receptor in eHSP90-dependent delivery of PEP1.

In addition, to check if the oxidative stress has an influence on penetration of PEP1, PDTC was added to the JFH-1 cells, and H2O2 was added to Huh7.5 cells, thereby producing various oxidative levels. These treating conditions brought about different influences on eHSP secretion depending on ROS levels (FIGS. 8 and 9). In accordance with the assumption by the inventors, PEP1 penetration into the JFH-1 cells was decreased in the presence of PDTC, and PEP1 penetration was increased in the Huh7.5 cells in the presence of H2O2 (FIGS. 13 and 14). This shows that endocytosis and biological activity of PEP1 are dependent on ROS levels in the cells, and thus dependent on eHSP levels.

Afterward, the hypothesis was verified by knocking down LRP1 in the JFH-1 cells and assessing ROS levels. The antioxidative activity of PEP1 in the JFH-1 cells was not observed in the presence of LRP1 siRNA (FIG. 15).

From the experimental results, it can be seen that an antioxidative mechanism of PEP1 is different from that of PDTC, PEP1 has a different level of endocytosis depending on the expression of LRP1, which is the HSP90 receptor, and when LRP1 expression was reduced or inhibited, endocytosis was reduced, indicating the HSP90-dependent entry of PEP1 into the cells.

5) Expression of HSP90 in HCV-Infected Liver Tissue

A histologically anatomical experiment was performed to verify that HSP90 expression was increased when an organ or tissue, not cells, was infected with HCV, different from when infected with HBV or AIH (autoimmune hepatitis (AIH).

According to the methods described in the experiments and analyses, HSP90 expression was compared in HCV, HBV and AIH-infected liver tissue. As a result, compared with HBV and AIH, when infected with HCV, HSP90 expression was increased (gray part, FIG. 20). Interestingly, PEP1 reduced iHSP90 in the JFH-1 cells, and it is considered that this is probably an incidental result according to the reduced ROS levels (FIG. 9). In addition, in HCV-infected liver tissue, when the control group (PBS) is compared with the PEP1-treated group, the PEP1-treated group showed lower HSP90 expression than the control group (gray part, FIG. 21).

FIGS. 20 and 21 show that HSP90 is highly present in the HCV-infected liver cells.

The experimental result shows that HCV infection induces higher levels of ROS in the cells than in normal cells, HSP90 is relatively overexpressed in cells under stress due to accumulated ROS, and PEP1 serves as a therapeutic agent for HCV-infected cells under oxidative stress.

Example 3

Confirmation of PEP1 Effect on HIV

When infected with viruses, it was confirmed that vigorous viral protein production also requires an HSP function, and the list of viruses inhibited by an HSP90 inhibitor is continuously increasing. It is also known that human immunodeficiency virus-1 (HIV-1) infection induces increased HSP90 expression in monocytes. It can be seen that HSP90 acts in various cycles of the life cycle of the virus and thus plays an important role in HIV replication, and in acutely infected cells, the role of HSP90 in HIV transcription and replication is inhibited by the HSP90 inhibitor. Moreover, it was confirmed that HSP90 regulates HIV reactivation from a latent state by regulating NF-κB signaling.

Culture of Cell Lines

The cell lines used in the example relating to the HIV antiviral effect of PEP1 of the present invention were derived from a human T cell leukemia cell line MT-4, an ACH-2 cell line infected with latent HIV-1, and a 1G5 cell line derived from Jurkat and comprising a stably-inserted HIV-LTR-luciferase (luciferase) construct, and these cell lines were obtained from the NIH/AIDS Research and Reference Reagent Program (NIH, Bethesda, Md.). 293FT cells were purchased from Life Technologies (Carlsbad, Calif.). The MT-4 and 1G5 cell lines were maintained in RPMI 1640 supplemented with glutamine (2 mM), 10% bovine fetal serum (FBS) and penicillin-streptomycin. The ACH-2 cells were cultured in RPMI 1640 supplemented with 2 mM glutamine, 10% FBS, penicillin-streptomycin and 5 mM HEPES. The 293FT cell line was cultured in DMEM containing 10% FBS, penicillin-streptomycin, 6 mM L-glutamine, 1 mM sodium pyruvate and 0.1 mM non-essential amino acids.

Reagents and Antibodies

As anti-retro virus drugs, T-20, raltegravir, flavopiridol and ritonavir were obtained from the National Institute of Health (NIH, Bethesda, Md., USA), AIDS division, NIH/AIDS Research and Reference Reagent Program (NIH, Bethesda, Md., USA), and dissolved in D-PBS, DMSO or distilled water as described in the manufacturer's instructions. Azidothymidine (3-azido-3-deoxythymidine, AZT) was purchased from Sigma Aldrich (St. Louis, Mo.). HSP90 (#4877S), phospho-NF-κB (p65, #3033S), IκB (#4814S) and phospho-IκB (#2859S) were obtained from Cell Signaling (Danvers, Mass.), and anti24 antibodies (ab9071) were purchased from Abcam (Cambridge, Mass.). Antibodies against HSP70 (sc32239), antibodies against GFP (sc81045), antibodies against GAPDH (sc25778) and antibodies against NF-κB (p65, sc372) were purchased from Santa Cruz Biotechnology (Santa Cruz, Dallas, Tex.).

Plasmids and Viruses

The pBR43IeG-rcmGBlnef provirus HIV-1 plasmid expressing both of Nef and the enhanced green fluorescent protein (eGFP) from single bicistronic RNA (Cat No. 11371, provided from Dr. Daniel Sauter and Dr. Frank Kirchhoff), and the pSV2tat72 plasmid (Cat. No. 294, provided from Dr. Alan Frankei) producing the Tat protein (residues 1-72) were obtained from the NIH/AIDS Research and Reference Reagent Program (NIH, Bethesda, Md.). To produce HIV-1, 293FT cells were transfected with a pBR_HIV-1_M_NL4-3_IRES_eGFP vector using the Lipofectamine 2000 reagent (Life Technologies) according to the manufacturer's instructions. Forty eight hours after transfection, the virus-containing medium was harvested, followed by brief centrifugation and filtration (0.45 μm). The virus titer was determined using p24 ELISA (ABL, Rockville, Md.). For amplification of infectious HIV-1, MT-4 cells were infected with the produced HIV-1 (MOI=0.5) for 48 hours. After brief centrifugation (1,300 rpm, 3 min), the supernatant was filtered (0.22 μm), and subjected to titration through p24 ELISA.

Assay for Anti-Viral Effect

To evaluate the anti-HIV-1 effect of PEP1, a cell-based anti-virus effect assay was carried out using MT-4 cells. The MT-4 cells ($4 \times 10^5$ cells) were infected with HIV-1 ($4 \times 10^5$ 50% cell culture infective dose ($CCID_{50}$)) for one hour. After washing with D-PBS twice, the infected cells were treated with PEP1 or anti-HIV-1 drugs. After two days of incubation, images of the MT-4 cells expressing eGFP were obtained using a fluorescence microscope before harvesting the cells. To remove cell debris, the collected supernatant was subjected to centrifugation at 13,000 rpm for 3 minutes, and to measure an extracellular viral amount, p24 ELISA or RNA extraction was performed for a reverse transcription-quantitative polymerase chain reaction (RT-qPCR). Meanwhile, the cell pellets were washed with D-PBS twice, and used for a cell viability assay. To investigate the role of HSP90 in the antiviral action of PEP1, MT-4 cells were infected with HIV for one hour, and treated with anti-HSP70 (10 ng), anti-HSP90 (10 ng) (Cell Signaling, Danvers, Mass.) or 17-AAG (1 µM) (Calbiochem, Darmstadt, Germany). HIV-1 replication was analyzed by p24 ELISA, and eGFP was monitored using a fluorescent microscope. In addition, the cell lysate were immunoblotted using anti-GFP antibodies to confirm HIV-LTR-dependent synthesis of eGFP.

Cell Cytotoxicity Assay

MT-4, 1G5 or ACH-2 cells were seeded in a 96-well microplate at a density of $1 \times 10^4$ cells/well, and incubated with increasing concentrations of PEP1 for 5 days. Cell viability was determined by colorimetry using a CellTiter96 Aqueous One Solution assay kit (Promega, Wis.) according to the manufacturer's instructions. To assess the cell protective effect of PEP1 from HIV-1-induced cell death, MT-4 cells ($1 \times 10^4$) were infected with the HIV-1 virus ($4 \times 10^5$ $CCID_{50}$) for 5 days with or without PEP1, and subjected to a cell viability assay.

Measurement of HIV-1 Virus Production

To measure HIV-1 virus titers, HIV-1 p24 antigen capture ELISA (p24 ELISA, ABL) and RT-qPCT assay were performed according to the manufacturer's instructions. HIV-1 RNA genomes were purified from the cell culture supernatants and pellets using a QIAamp Ultrasens Virus kit (Qiagen, Hilden, Germany) according to the manufacturer's instructions. The HIV-1 RNA levels were quantified by RT-qPCR using a primer pair specific to gag of HIV-1. Glyceraldehyde phosphate dehydrogenase (GAPDH) was used as a reference gene for normalization. The following primer pairs were used for qPCR: Gag, 5'-TGC-TATGTCAGTTCCCCTTGGTTCTCT-3' (sense, SEQ ID NO: 5) and 5'-AGTTGGAGGACATCAAGCAGC-CATGCAAAT-3' (antisense, SEQ ID NO: 6); and GAPDH, 5'-AATCCCATCACCATCTTCCA-3' (sense, SEQ ID NO: 7) and 5'-TGGACTCCACGACGTACTCA-3' (antisense, SEQ ID NO: 8). An HIV type 1 Genesig Standard kit (Primerdesign, Southampton, UK) was used to measure virus titers. The concentration of the stocked virus was $2 \times 10^5$ copies/µl.

Results of Experiments

1) Inhibition of HIV-1 Replication by PEP1

On the basis of the findings of the critical role of HSP90 in the HIV-1 life cycle and the interaction between PEP1 and HSP90, the inventors hypothesized that PEP1 is able to inhibit the antiviral activity with respect to HIV-1, and verified this. Prior to investigating the role of PEP1, the cell cytotoxicity of PEP1 was first analyzed to exclude the possibility that PEP1 affects the replication of HIV-1 due to its non-specific cell cytotoxicity.

FIGS. 22 to 27 show the data indicating that PEP1 inhibits HIV-1 replication. PEP1 did not exhibit significant cytotoxicity against MT-4, 1G5 and ACH-2 cells up to 25 µM (FIG. 22). First, the anti-HIV-1 activity of PEP1 was measured by analyzing its effect on HIV-1 replication in MT-4 cells. The MT-4 cells were infected with HIV-1 produced from pBR_HIV-1-M-NL4-3_IRES_eGFP, and treated with various concentrations of PEP1. As determined by p24 ELISA, production of viral particles in MT-4 cells was significantly inhibited by PEP1 in a dose-dependent manner, and the mean 50% inhibitory concentration ($IC_{50}$) value was approximately 0.85 µM (FIG. 23). Additionally, eGFP production, which depends on the activation of HIV-1, was also decreased by treatment with PEP1. Such a result further supports the anti-HIV-1 effect of PEP1 (FIG. 24). Inhibition of viral particle production by PEP1 was further confirmed by measuring HIV-1 genome RNA levels of generated viral particles. PEP1 exhibited a dose-dependent inhibitory effect, and 5 µM PEP1 exhibited a decrease in viral RNA level by approximately 100 times (FIG. 25).

It has been known that apoptosis of HIV-infected cells occurs by an intracellular cell death mechanism. To investigate whether PEP1 has an inhibitory effect on HIV replication and an effect of inhibiting the action by which HIV-infected cells undergo inherent apoptosis, an anti-cytopathic effect assay was performed. In agreement with the inhibition of HIV-1 replication by PEP1, PEP1 shows the cell protective effect in HIV-1-infected MT-4 cells. AZT and PEP1 showed considerable cell protective effects in a dose-dependent manner (FIGS. 26 and 27). Similar to AZT, 5 µM PEP1 exhibits an almost 100% cell protective action from HIV-1-mediated cell death. Such a cell protective effect is inversely proportional to a decreased supernatant p24 level, suggesting that PEP1 is able to protect cells by inhibiting viral replication.

2) Inhibition of HIV-1 Transcription by PEP1

Considering that eGFP production from HIV-1 genomes is under the same control as Nef, a decrease in eGFP expression in HIV-1-infected cells by PEP1 indicates the inhibition of HIV-1 transcription by PEP1 (FIG. 30). To further investigate the mechanisms of HIV-1 inhibition by PEP1, a time-of-addition (TOA) assay was performed using PEP1 and conventional anti-HIV drugs which have been known to act at different stages of the replication. The characteristics of the control anti-HIV drugs have been well known, and inhibition of each drug occurs at a different stage of the HIV replication: AZT inhibits reverse transcription activity, and inhibits HIV proliferation when cells are treated with it between 3 to 4 hours; Raltegravir inhibits integrase activity for inserting HIV DNA into a host DNA genome, and inhibits HIV proliferation when cells are treated with it between 6 to 8 hours; Ritonavir inhibits protease activity to prevent processing of the precursor of a gal-pol polypeptide, thereby generating non-infectious immature HIV particles, and inhibits HIV proliferation when cells are treated with it up to 15 hours; and T-20 inhibits the fusion between a virus and the cell membrane to disturb the entry of the HIV virus into cells, and when cells are further incubated with it for 24 hours, HIV proliferation occurs at a level ⅓ lower than the control drug DMSO which is not a therapeutic agent.

FIGS. 28 to 30 show the inhibition of HIV-1 replication by PEP1 at the transcriptional level. In the TOA assay, the results of each drug have shown that the inhibition of HIV replication was well exhibited at a time point corresponding to the replication targeted by the drug, and the HIV inhibition by PEP1 occurs at a time period between 11 to 13 hours after HIV-infected MT-4 cells were treated with PEP1 (FIG. 28). Analysis of eGFP expression confirmed that the inhibitory activity of PEP1 is weakened when treated for 12 hours after infection (FIG. 29). According to the typical result from TOA, the HIV transcription from the inserted HIV genome occurs between 11 to 13 hours after infection. Such a result suggests that the mode of action of PEP1 in the HIV-infected MT-4 cells is to inhibit HIV proliferation through inhibiting transcription activity, as expected. The hypothesis of the inventors further supported by an analysis at the viral mRNA level. When cells were treated with PEP1 for 9 hours after infection, PEP1 effectively inhibited the viral mRNA production of HIV-1, but when treated for 13 hours after infection, it lost the activity to reduce viral mRNA (FIG. 30). At the same time, there was no significant change in housekeeping host GAPDH mRNA synthesis, suggesting that PEP1 selectively regulates HIV-1 viral transcription.

From the experimental results and the known procedure of HIV proliferation by time periods, it can be seen that the time period when PEP1 exhibits an inhibitory effect on proliferation, from 11 to 13 hours, corresponds to the early stage of the late phase in which HIV DNA is integrated into the nucleus of a cell line, and starts to proliferate using an intracellular transcription factor. This indicates that PEP1 inhibits the virus at the time of transcription occurring within the nucleus of the cell during its life cycle with several steps required for proliferation, and it can be seen that PEP1 can exhibit an excellent effect as an anti-HIV inhibitor.

3) Tat-Dependent Inhibition of HIV-1 Transcription by PEP1

An HIV-1 transactivation protein (Tat) is a regulatory protein dramatically enhancing HIV-1 transcription through the interaction with the tat-transcriptional active region (TAR). Since PEP1 selectively regulates HIV-1 transcription, the inventors conducted an experiment to see if PEP1 affects HIV-1 Tat transactivation. In the present invention, as a Jurkat-derived cell line, 1G5 containing a stably-inserted HIV-LTR-luciferase construct was used. After 1G5 was infected with HIV-1, or transfected with a tat-retrovirus vector (pSV2tat72) in the presence of AZT or PEP1, luciferase activity was analyzed.

The 1G5 cells transfected with the HIV-LTR-luciferase construct were infected with HIV-1, followed by post-treatment with DMSO, AZT or PEP1. Four days after the infection, a luciferase assay was performed to analyze transactivation of the cell lysate HIV-LTR. The 1G5 cells infected with HIV-1 showed a drastic increase in luciferase activity (FIG. 31). The treatment with AZT or PEP1 reduced the effect of HIV-1 infection relative to HIV-LTR-luciferase activity by approximately five times (FIG. 31).

The 1G5 cells were transfected with Tat plasmids. Twelve hours after the infection, the cells were treated with the vehicle (DMSO), AZT or PEP1 as described above. Four days after the infection, the transactivation of HIV-LTR was analyzed through a luciferase assay. Data was expressed as means±SD. *** represents p<0.001 (FIG. 32). In line with the results shown in FIG. 31, PEP1 inhibits the activation of HIV-LTR luciferase activity by ectopic expression of Tat (FIG. 32). However, AZT did not inhibit the HIV-LTR luciferase activity in such an experimental setting. Such a result shows that PEP1 regulates the transactivation role of tat during HIV-1 infection, and thus inhibits the replication of HIV-1.

4) Inhibition of HIV-1 Reactivation from Latency by PEP1

While HIV replication may be successfully inhibited to lower than a detectable level through highly active antiretroviral therapy (HAART), HIV may stay in latently infected cells like resting memory CD4+ T-cells.

Tat acts as a molecular switch to regulate reactivation through the interaction between various types of related proteins.

Based on the fact that PEP1 regulates Tat-dependent transcriptional activity, the role of PEP1 in HIV-1 reactivation was investigated. ACH-2 cells, a human T cell line comprising a single copy of HIV-1 DNA, were treated with phorbol 12-myristate 13-acetate (PMA) along with a vehicle, AZT or PEP1. That is, ACH-2 cells, that is, cells latently-infected with HIV-1, were stimulated with PMA (50 nM) to induce reactivation of HIV-1 for 1 hour. Afterward, the cells were treated with DMSO, AZT, or PEP1 for 24 hours. A production level of viral particles in the supernatant was determined by p24 ELISA. As a result, PMA treatment significantly increased the supernatant p24 level, and PEP1 eliminated almost all of such an effect (FIG. 33, Data was expressed as means±SD. *** represents p<0.001 versus DMSO).

ACH-2 cells were treated with PMA, and then as shown in FIG. 33, AZT or PEP1 with stepwise increasing concentrations. The levels of viral genomic RNA of the produced viral particles were determined by RT-qPCR. As a result, AZT did not change the PMA effect. Such a result suggests that PEP1 inhibits PMA-induced HIV-1 reactivation, and inhibits the production of viral particles. Similarly, HIV-1 RNA genome levels were also considerably reduced in a dose-dependent manner when the PMA-treated cell-derived supernatant was treated with PEP1 (FIG. 34, Data was expressed as means±SD. *** indicates p<0.001 versus DMSO).

5) HSP90-Dependent Anti-HIV-1 Activity of PEP1

It has been suggested that PEP1 interacts with HSP90 and HSP70. The interaction between PEP1 and HSPs results in modulation of the HIF-1α-VEGF signaling axis, indicating that PEP1 can regulate an intracellular signaling pathway through the interaction with HSPs. The inventors investigated whether PEP1 can regulate HIV-1 replication through the interaction with HSPs. Surprisingly, the inhibition of PEP1-mediated HIV-1 production in MT-4 cells was completely restored by treatment with anti-HSP90 neutralization antibodies.

However, there was no influence on AZT-mediated inhibition (FIG. 35). In other words, after infection with HIV-1 for 1 hour, the MT-4 cells were treated with anti-GAPDH, anti-HSP70, anti-HSP90 antibodies or 17AAG for 1 hour, and subsequently treated with DMSO, AZT or PEP1. Several hours after the infection, the production of HIV-1 particles were assessed by p24 ELISA. As a result, the treatment with anti-HSP70-neutralization antibodies resulted in partial restoration, and an isotype control of anti-GAPDH antibodies showed no significant effect. This suggests that the anti-HIV role of PEP1 is mainly caused by the interaction with HSP90 (FIG. 35).

In addition, the HSP inhibitor 17-AAG also eliminated the PEP1 effect, which confirmed that the anti-HIV activity of PEP1 is exhibited through HSP90 (FIG. 35). In addition, the PEP1-mediated inhibition of eGFP expression depending on HIV-1 transactivation was restored by anti-HSP90 antibodies.

MT-4 cells were infected with HIV, and treated with anti-GAPDH and anti-HSP90 antibodies. The cells were treated with DMSO, AZT or PEP1 for 24 hours as described above. To test the eGFP expression, the cells were lysed and then subjected to immunoblotting. As a result, an effect of AZT was not obtained (FIGS. 36 and 37). Such a result shows that PEP1 can regulate HIV-1 transcription activity through the interaction with HSP90.

6) Inhibition of Basal NF-κB Transcriptional Activity by PEP1

NF-κB triggers HIV transcription by interacting with an NF-κB-binding site in HIV-LTR, and increases the activation of TAT-mediated LTR translocation. In addition, Tat can directly activate NF-κB. Recently, there have been studies showing that eHSP90 can regulate various intracellular signaling pathways, including the NF-κB pathway. Since the elimination of the anti-HIV effect of PEP1 by anti-HSP90-blocking antibodies suggests the possibility of involvement of eHSP90 with respect to the anti-HIV function of PEP1, the inventors tested whether PEP1 regulates HIV-1 transcriptional activity by regulating NF-κB activity in an HSP90-associated manner. PEP1 dramatically reduced the basal NF-κB activity regardless of HIV-1 infection in the MT-4 cells (FIG. 38). Meanwhile, AZT exhibited no significant effect on NF-κB activity in the MT-4 cells. AZT shows a medium level of inhibitory effect in the HIV-1-infected MT-4 cells, which is probably because of a low HIV replication level (FIG. 38). The inhibitory effect of PEP1 on the basal NF-κB activity was further confirmed by EMSA (FIG. 39). PEP1-treated cells showed an apparent decrease in p65 NF-κB activation (FIG. 39). This shows that PEP1 inhibits the basal level of NF-κB DNA binding in the nucleus. In addition, the PEP1 treatment results in a decrease in NF-κB (p65) phosphorylation, indicating that PEP1 inhibits cytosolic activation of NF-κB and subsequent nuclear translocation (FIG. 40). A similar result was obtained from ACH-2 cells latently infected with HIV-1 (FIG. 40). As expected, the treatment with PEP1 resulted in a decrease in nuclear translocation of NF-kB(p65) in PMA-treated ACH-2 cells, versus DMSO-treated control cells (FIG. 41). Since the present invention shows that the anti-HIV effect of PEP1 is dependent on HSP90, the inventors tested whether an NF-κB inhibitory effect is dependent on HSP90. Consistent with the anti-HIV activity data, the NF-κB inhibitory effect of PEP1 was completely eliminated by treatment with HSP90 blocking antibodies or HSP inhibitor. Meanwhile, when treated with anti-GAPDH antibodies, there were no significant effects (FIG. 42).

Taken together, the inventors showed that PEP1 inhibits the basal level of NF-κB activity, thereby inhibiting HIV-LTR transactivation. Such a result shows that HSP90 is involved in this activity. In previous research, it has been seen that intracellular HSP90 plays a critical role in HIV reactivation by directly regulating NF-κB. In the present invention, nullification of the PEP1 effect on anti-HSP90 antibodies suggests that the antiviral effect of PEP1 is achieved through NF-κB signaling and HIV-LTR activation by HSP90.

Although HIV replication may be successfully inhibited by HAART, current therapies cannot eradiate latently-infected HIV-1. Viral reactivation is the main cause of the failure of such a therapeutic method. The stability of PEP1 has been already proven in various clinical trials. Therefore, the anti-HIV effect of PEP1 can provide an effective therapeutic method for inhibiting HIV reactivation.

Example 4

Confirmation of PEP1 Effect on HBV

To develop a target agent for liver cancer, various signaling pathways of IL-6/JAK/STAT, Ras/ERK, Wnt, etc., as well as EGFR tyrosine kinase and c-MET kinase, have been studied as target candidates. Among these, from the results of a variety of studies on the IL-6/JAK/STAT signaling pathway, it was confirmed that it can control inflammation and carcinogenesis, and thus can be an efficient target in an HBV-derived disease and HCC treatment. It was confirmed that abnormal activation of STAT3 in 72.4% of HCC tissue was observed, and STAT3 inhibition induces the growth of a liver cancer cell line and growth inhibition in animal models. To inhibit STAT signaling, almost all drugs currently entering or being used in clinical trials are kinase inhibitors. Although some of the drugs that directly inhibit STAT3 have entered a preclinical stage, due to the lack of druggability of the target itself and the selectivity of compounds with respect to a target, it was necessary to perform further studies on them. Particularly, with regard to the blocking of STAT3 signaling by inhibiting JAK2, there is no JAK inhibiting compound which is in a clinical trial targeting HCC. In addition, a compound of inhibiting such a single step has a high probability of resistance. Therefore, the inventors conducted research to develop a new compound which shows an inhibiting activity in several steps of the JAK2/STAT3 signaling pathway and is capable of overall inhibiting the signaling pathway.

Culture of Cell Line

A human HCC Huh7 cell line (American Type Culture Collection (ATCC), Manassas, Va., USA), a Huh7.5 cell line and a human hepatocellular carcinoma (HepG2) cell line (ATCC, Manassas, Va., USA) were cultured in a 5% $CO_2$ incubator at 37° C., and incubated in an RPMI 1640 medium supplemented with 10% bovine fetal serum (Invitrogen, USA), 2 mmol/ml L-glutamine, 100 μg/ml penicillin and 100 units/ml streptomycin.

Inhibition of Virion Production of Whole HBV Containing W4P

Focusing on the fact that liver cancer has a difference in frequency of occurrence according to sex, related research was conducted to find a variant (W4P) that is specifically found in males and associated with liver cirrhosis and liver cancer for the first time in the world. W4P is a novel Pre-S1 substituted W4P variant, which is a translation product obtained by changing wild-type TGG to CCG (underlining indicates the variants) in the $4^{th}$ amino acid, that is, a protein changing tryptophan (W) to proline (P) at the $4^{th}$ amino acid (the $4^{th}$ codon of preS1) of a genetic code encoding an antigen protein. It has been found that such a variant stimulates the occurrence and progression of liver cancer by regulating a JAK2-STAT3 signaling system through IL-6 in males, and was confirmed that higher levels of IL-6 in clinical samples were shown.

To observe virion production of entire HBV containing W4P by PEP1, $2 \times 10^6$ Huh7 cells were seeded into a 100 mm dish, and normal total HVC and HBV containing W4P were co-transiently transfected with a pCMV-β-gal vector including β-galactosidase, and incubated for 3 days. While changing the medium every 24 hours, the supernatant (sup) was collected. To analyze the supernatant, ELISA was performed according to experimental instructions using a generalized Bioelisa HBsAg color ELISA kit (BIOKIT S.A., Spain) and an HBeAg ELISA kit (BIOKIT S.A., Spain) that can detect a Hepatitis B surface antigen (HBsAg) and a Hepatitis B envelope antigen (HBeAg). 100 μl of each of the collected supernatants was added to each well, and reacted at 37° C. for 1 hour. 300 μl of a washing solution to each well for washing three times. 300 μl of a washing solution was added to the diluted conjugate solution for washing three times. 20 μl/ml of TMB was added to a substrate solution, and then 100 μl of the mixture was added to each well of a 96-well plate to allow a reaction for 30 minutes while light was blocked at room temperature. 100 μl of a stop solution was added to stop the reaction. The absorbance was read using an ELISA reader (Beckman, USA) at 450 nm. The ELISA results were calibrated using β-galactosidase used for calibration according to instructions provided by a reporter lysis buffer kit and a β-galactosidase analyzing system (Promega, USA).

Inhibition of Envelope Antigen Expression of Virion of Whole HBV Containing W4P

To confirm the potential to express the envelope antigen of whole HBV containing W4P by PEP1, $2 \times 10^6$ Huh7 cells were seeded into a 100 mm dish for transient transfection of normal whole HBV and whole HBV containing W4P, cultured for three days, cell pellets were collected by changing the medium, and then subjected to immunoprecipitation (IP). Pre-clearing was carried out for two hours at 4° C. by adding 20 μl of a protein A/G plus-agarose immunoprecipitant (Santa Cruz Biotechnology, USA) to the protein. 20 μl of protein A/G plus-agarose immunoprecipitant (Santa Cruz Biotechnology, USA) was added to the proteins in 400 μg of the pre-cleared lysate, and then reacted with 4 μg of primary antibodies for 24 hours at 4° C. Next day, after centrifugation at 2000 rpm and washing, the proteins were resuspended with 50 μl of a protein lysis solution. Western blotting was performed using primary antibodies preS1 and HBs antibodies.

Inhibition of Virion Proliferation of Whole HBV Containing W4P

To observe the potential for virion proliferation of whole HBV containing W4P, virion DNA was extracted from the entire supernatant while the medium was changed every 24 hours by the above-described method, and subjected to real-time quantitative PCR using a Quantitech SYBR Green Master-Mix kit (Qiagen). The entire supernatant was centrifuged using an ultracentrifuge equipped with an SW28 swing rotor at 20,000 rpm for 2 hours to precipitate the virus, and the precipitated viral pellets were suspended with 200 μl of sterilized DW. To extract virion DNA, the viral cells were treated with 100 μg/ml RNase A, 100 μl of a lysis buffer (0.25% SDS, 0.25M Tris, 0.25M EDTA), and 500 μg/ml of proteinase K for 2 hours at 37° C. Afterward, DNA was extracted by a phenol:chloroform extraction method. To see the capacity for viral proliferation, real-time PCR primers SF-Real (5'-TTG ACA AGA ATC CTC ACA ATA CC-3', SEQ ID NO: 9) and SR-Real (5'-GGA GGT TGG GGA CTG CGA AT-3', SEQ ID NO: 10) targeting small surface area regions of HBV were designed. 12.5 μl IQ SYBR Green Supermix (Biorad, Calif., USA), 1.25 μl SF-Real primer, 1.25 μl SR-Real primer, 9 μl distilled water, and 1 μl cDNA were added to a 96-well plate. Real-time PCR was performed at 40 cycles of 5 min at 95° C., 15 sec at 94° C., and 15 sec at 60° C. using the Exicycler™ 96 Real-Time Quantitative Thermal Block System (Bioneer Co., Korea), and the temperature was increased from 53° C. to 90° C. by modulating to 0 sec at 95° C., 30 sec at 53° C. and modulating by 0.1° C. per second to analyze a melting curve.

Transgenic Mice

HBV transgenic mice were prepared by injecting a 1.1-fold HBV base sequence comprising a full open reading frame (ORF) into the fertilized eggs of the mice through microinjection. The base sequence of HBV used in the research was obtained using a pHY92-W4P plasmid. The pHY92-W4P plasmid was digested with EcoRi before injection into the fertilized eggs of the mice, and finally a base sequence of 3.9 kb in length was used for microinjection. Produced subjects were selected through PCR using a specific sequence of HBsAg. PCR-positive subjects were selected according to the concentrations of serum HBsAg and HBeAg, and finally used as PCR-positive, HBsAg-positive, and HBeAg-positive mice in the study. These mice were backcrossed with C57BL/6 mice to produce heterologous HBV transgenic mice. Southern and northern hybridization were performed on mice showing high HBsAg-, HBeAg-positive levels among the offspring to confirm transcription of HBV replication intermediates of liver cells. The HBV transgenic mice showing high transcription with an HBV replication intermediate of the liver cells were used for antiviral research by PEP1.

Animal Test Using Hydrodynamic Injection

From the day after total HBV W4P genomic DNA (1.8 ml solution injected within 5 s into 20 g mice) was injected into C57/BL6 mice, PEP1 (50 μg/kg) was treated twice a week through subcutaneous injection. Blood samples were obtained 1, 3, 7, 10 and 14 days, and 2 weeks after treatment, the whole blood was obtained from the mice after being anesthetized and sacrificed on day 14. Serum was isolated from the blood, and the liver was rapidly dissected and homogenized.

HBsAg Detection, Quantification of HBV Titers and Western Blotting

HBsAg levels in the HBV-transgenic mice were determined using an HBsAg ELISA kit (BIOKIT, Germany). To quantify HBV titers, total DNA was extracted and confirmed by real-time PCR. For western blotting, cells were lysed using the same amount of a protein lysis solution as 8 M urea and separated through electrophoresis to be bound with antibodies, and then the antibodies were confirmed using an enhanced chemiluminescence (ECL) kit (Perkin Elmer, USA).

RNA Extraction and Northern Blotting

Cellular RNA extracted through cell lysis using REzol (PROtech Technologies, Taiwan) was isolated using isopropanol precipitation. The obtained RNA was treated with RNase-free DNase I (Roche, Germany) for 30 minutes at 37° C. to remove remaining DNA plasmids. Afterward, RNA was purified using extraction with phenol/chloroform, ethanol precipitation and resuspension. For northern blotting, the same amount of RNA was isolated through electrophoresis with a 2% formaldehyde gel, transferred to a membrane, and then subjected to staining with P32-labeled HBV full-length probes corresponding to the total bases of HBV. As a loading control, hybridization of P32-labeled GAPDH probes was used on the same membrane.

Isolation and Southern Blotting of HBV Core-Binding DNA

To extract HBV DNA from the liver tissue of a mouse, the following method according to a conventional procedure was used. For cell lysis, 1.2 mL of NET buffer (50 mM Tris-HCl, pH8.0, 1 mM EDTA, pH8.0, 100 mM NaCl, 0.5% NP-40) was added per 10-cm dish, and stirring culture was carried out for one hour at 37° C., and centrifugation (13 k rpm, 10 minutes, 4° C.) was carried out to remove a nucleus. The supernatant was adjusted with 6 mM $CaCl_2$ and incubated with a micrococcal nuclease (Amersham Pharmacia Biotech AB, Sweden) for 30 minutes at 37° C. to lyse cytoplasmic RNA or remaining DNA plasmids. Afterward, enzymes were inactivated using 20 mM EDTA for 15 minutes at 65° C. 200 μg/ml of proteinase K (Sigma) and 0.5% SDS were treated overnight at 50° C. to lyse proteins in the supernatant and extract HBV core-binding DNA. HBV DNA was extracted with phenol/chloroform, and purified using ethanol precipitation and resuspension with a TE buffer solution. For northern blotting, ⅕ of the amount of the purified HBV DNA was subjected to 1.5% electrophoresis, and then transferred to a membrane and stained with P32-labeled-HBV full-length probes.

Analysis of IL6, TNFα Cytokines

To compare IL6 and TNFα levels in mouse sera obtained from PEP1-treated transgenic mice and hydrodynamically-injected models, analyses were performed according to the manufacturer's instructions using an R&D ELISA kit. The absorbance was read using an ELISA reader (Beckman, USA) at 450 nm.

Analysis of RNA Expression

RNA obtained from the liver tissue of mice was used to observe and compare, at the RNA level, inflammation-related cytokines such as IL6, IL1β and TNFα, compare the expression of hepatic fibrosis marker TGFβ, collagenase I and IV, and RNA expression levels of immune cell markers 4/80 and CD68, a chemokine attractant protein and their receptors were determined through real-time PCR. Control group RNA was compared with 18S expression.

Analyzes of Immune Cells in Spleen of Wild-Type and Whole HBV W4P Genome-Injected Mice The spleen was separated from a transgenic mouse, immune cells in the spleen were harvested, and distribution of B cells, T cells (CD8+, CD4+CXCR5+TFH cells), and NKT cells were analyzed using flow cytometry. The splenic cells were incubated with purified wild-type and mutant envelope antigens, and the proliferation of T cells was determined by thymidine uptake. At the same time, the potential for T cell proliferation after mitogen treatment was studied by treating PHA, anti-CD3 antibodies, etc. and determining T cell proliferation by the same method as described above.

Analyses of Immune Cells in Liver of Wild-Type and Whole HBV W4P Genome-Injected Mice After portal venous liver perfusion using a digestion solution containing a collagenase, the liver was homogenized, cells were obtained from the digestion solution, the liver cells were removed through low centrifugation (30 RCF/3 min), and immune cells in the liver were obtained through gradient centrifugation. After Fc-blocking, flow cytometry was performed using anti-CD3, anti-CD4, anti-CD8, anti-NK1.1, anti-CD19, anti-CD11b, and anti-CD11c antibodies to analyze the distribution of immune cells in the liver.

Analysis of T-Cell Activity

After a P815 cell line expressing envelope antigens was prepared to activate the immune cells obtained from the spleen and the liver for 5 days, a degree of the activation of cytotoxic T cells was determined by analyzing cytotoxicity of T cells isolated using P815 cells expressing envelope antigens as target cells. In addition, T cells were also isolated from the immune cells obtained from the spleen and the liver using a T-cell concentration column (R&D) and incubated with the P815 cell line expressing envelope antigens for 16 hours, and then T cells specifically producing γ-interferon were detected using a type 2 Interferon-γ ELISPOT kit.

Statistical Treatment

When a difference between categories was compared using an SPSS 12.0K program, a Fisher's exact test or a Chi-square test was used. When continuous variables were normally distributed, for analysis, a Student's t-test was used, otherwise, a Mann-Whitney U-test was used. When a P value was 0.05 or less, it was determined as statistical significance.

Analysis of Test Results

1) Confirmation of Potential to Inhibit HBsAg Synthesis by PEP1 Peptide in Whole HBV W4P Genome-Injected Huh7, Huh7.5 and HepG2 Cell Lines The effect of PEP1 on HBsAg secretion was observed using the whole HBV W4P genome established by the inventors, which induces the secretion of HBV HBsAg and virions, and various human HCC cell lines. Huh7, Huh7.5 and HepG2 cell lines were transient-transfected with the whole HBV W4P genome, treated with 10 μM PEP1 and 10 μM of a representative anti-viral agent, ramivudine, (hereinafter, referred to as 3TC), and after 48 hours, the pellets and the supernatant (sup) were subjected to ELISA. Consequently, according to the intracellular and extracellular HBsAg levels, it can be seen that PEP1 exhibited inhibitory effects in the HepG2 cell line, and only showed intracellular inhibition but no difference in extracellular inhibition in the Huh7 cell line, whereas neither an intracellular nor extracellular inhibitory effect was observed in the Huh7.5 cell line. While HBV polymerase inhibitor 3TC also exhibited higher inhibitory effects than the control group, it did not have a significant difference, compared to the PEP1-treated group (FIG. 43). For the results, it was proved that the PEP1 peptide has an inhibitory effect on HBsAg synthesis of HBV like the representative anti-viral agent 3TC (SEM of data was obtained from three experiments in duplicate. * P<0.05, **P<0.01).

2) Confirmation of Inhibition of Virion Production by PEP1 Peptide in Whole HBV W4P Genome-Injected Huh7, Huh7.5 and HepG2 Cell Lines To observe the virion production in the supernatant after the inhibition of HBsAg secretion by the PEP1 peptide was observed, virions were collected from the supernatant obtained by the above-described method using PEG 6000, and HBV DNA was obtained using a virus DNA prep kit (Intron, Korea), and then quantified by real-time PCR. As a result, the levels of the virions produced in the supernatant indicated the inhibitory effect by PEP1 like 3TC in both of the HepG2 and Huh7 cell lines, but there was no effect on virion secretion in the Huh7.5 cell line. While the HBV polymerase inhibitor 3TC also showed the inhibitory effect compared to the control group, it showed no significant difference in inhibitory effect, like in the HBsAg synthesis potential, compared to the PEP1-treated group (FIGS. 44a, 44b, 44c, and 44d). From these results, it was proven that, like the representative anti-viral agent 3TC, the PEP1 peptide also has an inhibitory effect in virion production of HBV (SEM of data was obtained from three experiments in duplicate. * P<0.05, P<0.01,*P<0.001).

3) Confirmation of Inhibition of HBsAg Synthesis According to Concentration of PEP1 Peptide in Whole HBV W4P Genome-Injected HepG2 Cell Lines In the experiment for observing the inhibitory effect of the PEP1 peptide on HBsAg synthesis in Huh7, Hu7.5 and HepG2 cell lines, to observe the effect according to PEP1 concentration using the most effective HepG2 cell line, the HepG2 cell line was transfected with the whole HBV W4P genome, treated with the PEP1 peptide at different concentrations of 0.01, 0.1, 1, 10, and 100 μM, and after 48 hours, the pellets and the supernatants were collected and subjected to ELISA. As a control group, the antiviral agent 3TC was also treated in the same manner. As a result, in the pellets, the PEP1 peptide showed inhibitory effects when treated at 0.01 μM or higher, which were slightly different according to concentration. However, in the supernatants, until 10 μM, the PEP1 peptide showed inhibitory effects, but at 100 μM, it showed no effect. In contrast, 3TC showed inhibitory effects according to concentration in both of the pellets and the supernatants. From these results, it was confirmed that the PEP1 peptide showed a concentration-dependent effect on HBsAg synthesis in the pellets (in FIG. 45, SEM of data was obtained from three experiments in duplicate. * P<0.05, P<0.01, *P<0.001).

4) Concentration-Dependent Inhibition of Virion Production According to Concentration of PEP1 Peptide in Whole HBV W4P Genome-Injected HepG2 Cell Lines In the previous experiment, to observe the virion production according to peptide concentration in the supernatant, real-time PCR was performed by harvesting virions from the supernatant. As a result, in the pellet, the PEP1 peptide was not effective at a low concentration of 0.01 μM, showed an approximately 48% reduction effect at 10 μM, but was not effective at a high concentration of 100 either. However, it was observed that 3TC also has an inhibitory effect on virion synthesis according to concentration. From these results, it was confirmed that the PEP1 peptide has a concentration-dependent effect on virion production up to 10 M (in FIG. 46, SEM of data was obtained from three experiments in duplicate. * P<0.05, P<0.01, *P<0.001).

5) Effect of PEP1 Peptide on HNF4αExpression

It is known that the hepatocyte nuclear factor 4α binds to HBV enhancer I and thus plays a critical role in HBV synthesis. Therefore, 48 hours after the whole HBV W4P genome was injected into a HepG2 cell line and treated with 10 μM PEP1, proteins were extracted from the pellets, and subjected to western blotting. As a control group, a mock vector was injected and compared.

As a result, when the whole HBV W4P genome inducing HBV proliferation was injected, increased HNF4α expression was observed, confirming that the HNF4α expression was more effectively reduced by the PEP1 peptide than 3TC. Therefore, it was proved that the anti-HBV effect of the PEP1 peptide results in inhibiting viral proliferation by regulating the expression of HNF4α, which is a transcription factor (FIG. 47).

6) Effect of PEP1 Peptide on Inflammation-Related Cytokines

It has been reported that HBV preS1 W4P variants are closely related to production of IL-6, which is an inflammation regulatory cytokine. Therefore, to observe an anti-inflammatory effect of PEP1 in IL-6-induced cell lines, 48 hours after the whole HBV W4P genome was injected into HepG2 and Huh7 cell lines which were then treated with 10 μM PEP1 and 10 μM 3TC, respectively, IL-6 levels in the culture supernatants were observed through ELISA. As a result, when the whole HBV W4P genome inducing IL-6 proliferation was injected, the IL-6 level was too low to be detected in the HepG2 cell line, and PEP1 showed no IL-6 inhibitory effect in Huh7 cell line. It was similarly observed that the 3TC-treated group exhibited no effect on production of IL-6 cytokine (FIG. 48).

7) Effect of PEP1 on HBsAg Synthesis and Virion Production in Whole HBV W4P Genome-Transgenic Mice To observe an antiviral effect of the PEP1 peptide, HBsAg synthesis was observed using transgenic mice prepared by injecting the whole HBV W4P genome. The PEP1 peptide was injected into the caudal vein of a mouse twice a week at a concentration of 50 μg/kg. As a control group, 500 μg/kg of 3TC, like the PEP1 peptide, was injected in the same manner, and after 4 and 8 weeks, the whole blood was collected from mice and subjected to HBs ELISA to observe an HBsAg level in serum. In addition, HBV virion DNA was obtained from mouse serum and subjected to real-time PCR.

As a result, when treated up to 4 weeks, neither the PEP1 peptide nor 3TC showed a reduction effect on the level of HBsAg in serum, but on week 8, the PEP1 peptide showed an approximately 10% reduction effect, compared to 3TC showing no such effect. In addition, to observe a virion level, virion DNA was obtained from the mouse serum and subjected to real-time PCR. On week 4 after the treatment, the PEP1 peptide and 3TC did not show virion inhibitory effects as with HBsAg, but on week 8, the PEP1 peptide showed an approximately 50% inhibitory effect, and 3TC showed an approximately 52% inhibitory effect. Therefore, it was confirmed that PEP1 inhibited the production and secretion of virions produced in whole HBV W4P variant genome-containing transgenic mice (FIG. 49).

8) Effect of PEP1 Peptide on Protein Expression in Whole HBV W4P Genome-Transgenic Mice To observe a change in protein expression affecting the antiviral effect by the PEP1 peptide, transgenic mice prepared by injecting the whole HBV W4P variant genome were used. The PEP1 peptide was injected into the caudal vein of the mouse at a concentration of 50 μg/kg twice a week. As a control group, 500 μg/kg of 3TC was injected like the PEP1 peptide. On week 8, the whole blood was collected from the mouse, and proteins were extracted from the liver of the mouse and subjected to western blotting to observe expression of the proteins.

As a result, the PEP1 peptide showed no effect on the expression of heat shock protein 90 (HSP 90) closely related to the activity of HBV reverse transcriptase critical to HBV proliferation and superoxide dismutase (SOD) which was increased in activity in patients with chronic hepatitis by HBV. However, it was confirmed that, among ras/raf-mitogen activated protein kinases (MAPKs) closely related to HCC progression caused by HBx serving as a transcriptional activator in various signal pathways, particularly, protein phosphorylation of extracellular signal-regulated protein kinase (ERK) was inhibited by the PEP1 peptide, and JAK2 phosphorylation in Janus kinase/signal transducer and activator of transcription (JAK/STAT) signaling was also regulated by the PEP1 peptide. It was also confirmed that 3TC as a control group inhibited phosphorylation in ERK and JAK2 signaling. Therefore, it was considered that the PEP1 peptide is able to play a critical role in inhibiting HCC progression caused by HBV by regulating HBV proliferation, and the MAPK and JAK/STAT signaling playing critical roles in HCC progression (FIG. 50).

9) Effect of PEP1 Peptide on Distribution of Immune Cells in Whole HBV W4P Genome-Transgenic Mice PEP1 is an HLA Class II-binding peptide derived from telomerase, and a 16-amino acid peptide triggering cytotoxic T-cell and helper T-cell immune responses. Therefore, to observe a change in the distribution of renal immune cells by the PEP1 peptide, transgenic mice were prepared by injecting the whole HBV W4P variant genome, on week 4, the whole blood was collected from the mice, and immune cells were isolated from the kidneys of the mice and then stained with lymphocyte markers (B cells (CD19B), CD4, CD8, NK1.1 cells) and myeloid cell markers (DC (CD11c), a macrophage marker (F4/80), a neutrophil marker (Ly-6G), a monocyte marker (Gr1)) according to an extracellular cell surface staining method for FACS analysis.

As a result, it was confirmed that the PEP1 peptide caused no significant difference among all of the lymphocytes such as B cells, CD4, CD8, and NK1.1 cells, and there was no effect on cell distribution of myeloid-derived cells such as DCs, macrophages, neutrophils, and monocytes, either. It was also confirmed that 3TC, like PEP1, did not have an influence on the distribution of immune cells of the whole HBV W4P genome-transgenic mice (FIGS. 51a to 51h).

10) Effect of PEP1 Peptide on Interferon γ (INFγ) Activity in Whole HBV W4P Genome-Transgenic Mice INF, which is a hormone-like cytokine, is secreted from immune cells against a virus. INFs are present in three types such as α, β and γ, and among these, INFγ is known to be critical for inhibiting the hepatitis B virus (HBV) in humans. Therefore, to observe the activity of INFγ, as an immune response, by the PEP1 peptide, 8 weeks after 50 μg/kg of the PEP1 peptide and 500 μg/kg of 3TC were injected into the caudal vein of each of transgenic mice prepared by injection of the whole HBV W4P variant genome twice a week, the whole blood was collected and a kidney was extracted from the mouse, and then immune cells were isolated and treated with HBsAg for stimulation. Seventy two hours after the stimulation, the INFγ cytokine was accumulated in cells by Brefeldin A and stained by an intracellular staining method for FACS analysis.

As a result, all of the CD4, CD8 and NK1.1 cells did not exhibit INFγ activity by the PEP1 peptide, and also exhibited slightly increased activity by 3TC. However, there was no significant difference in activity (FIGS. 52a to 52g).

11) Effect of PEP1 Peptide on Differentiation of Macrophages in Whole HBV W4P Genome-Transgenic Mice It has been known that an antiviral effect is exhibited as the differentiation of macrophages to M1 leads to the cell death of infected cells. Therefore, to observe if the PEP1 peptide is able to differentiate macrophages to M1, eight weeks after PBS, 50 μg/kg of the PEP1 peptide and 500 μg/kg of 3TC were injected into the caudal vein of each of transgenic mice prepared by injecting the whole HBV W4P variant genome twice a week, the whole blood was collected from the mouse and a kidney of the mouse was extracted, immune cells were isolated and stained with a macrophage marker (F4/80) and M1 marker MHCII through an extracellular cell surface staining method. Afterward, FACS analysis was carried out.

As a result, while the distribution of macrophages among the myeloid-derived cells was significantly increased due to the PEP1 peptide, the number of cells differentiated to M1 was increased, compared to the PBS group, but not significantly. The HBV polymerase inhibitor 3TC did not show a difference between cell distribution and differentiation (FIG. 53).

12) Antiviral Effect of PEP1 Peptide by Blockage of HSP90 in Whole Wild-Type HBV Genome-Transfected Cells PEP1 has been known to pass through a cell membrane from the outside to the inside of the cells in a shuttle method via HSP90. To confirm if the antiviral effect is reduced in cells by blocking the HSP90 activity based on such a mechanism, in this research, a HepG2 cell line was transiently transfected with the whole HBV wild-type genome, treated with anti-GAPDH, anti-HSP (1 ug/ml, blockage of HSP90 activity) and 17-AAG (1 μM) for 1 hour, ant then with PBS (0.5%), entecavir (ETV, 30 nM) and PEP1 (5 μM) for 24 hours. Subsequently, the supernatant was collected and treated with PEG6000 to precipitate the virus, and viral DNA was extracted and subjected to real-time quantitative PCR to observe an antiviral effect. All experiments are independently performed in triplicate, and a statistical significance test was performed using one-way ANOVA through the Tukey's Multiple Comparison Test. ** $p<0.05$ versus PBS, and ## $p<0.05$ versus None.

As a result, it was confirmed that the antiviral effect of PEP1 was statistically more significantly shown in PEP1-treated cells than in untreated cells and when ETV was treated, and the same result was obtained in the GAPDH-blocked group. It was confirmed that, in the group treated with HSP90 and 17-AAG known as an HSP90 inhibitor, there was no statistically significant antiviral effect of PEP1 (FIG. 54). On the other hand, it was confirmed that there was no difference in the antiviral effect of ETV in untreated cells, or cells treated with GAPDH, HSP90 or 17-AAG.

As described above, it was confirmed that the PEP1 peptide binds to an HBV enhancer during HBV transcription to inhibit the expression of HNF4α which is a transcription factor critical for increasing the activity of the enhancer, resulting in reduction of HBV HBsAg and virion production.

In addition, it can be seen that PEP1 plays a critical role in blocking the progression of cells infected with HBV to HCC by inhibiting HBV proliferation through the inhibition of ERK and JAK/STAT signal pathways, which are critical in HCC progression.

When a human body is infected with viruses, immune cells secrete INFs against such viruses. Particularly, INFγ is known to play a crucial role in inhibiting HBV in the human body, and thus it is important to determine the distribution of immune cells when the human body is infected with HBV and a ratio of immune cells exhibiting INFγ secreting activity. Compared with the PBS-treated group as a control group, it was confirmed that immune cells increased in the ratio of immune cells in whole HBV W4P variant genome-containing transgenic mice and the activity of INFγ cytokine due to PEP1 of the present invention did not have any differences. As a result, it is considered that, in the HBV-infected human body, the PEP1 peptide plays crucial roles in inhibiting HBV proliferation by inhibiting the synthesis of HBV mRNA through inhibition of the ERK or JAK/STAT signal pathway or reducing the expression of HNFa, which is a transcription factor acting on an HBV enhancer, rather than regulating an immune system in the human body.

Like this, it can be seen that PEP1 has an antiviral effect against HBV, and the stability of PEP1 has been already proven by various clinical trials. Therefore, the anti-HBV effect of PEP1 can provide a composition for treating an HBV-infected disease, which has neither hepatotoxicity nor nephrotoxicity and is safe, and a method for treating the disease.

According to the examples, it was able to see that PEP1 which is the peptide according to the present invention and a composition containing PEP1 have a viral replication inhibitory effect and an antiviral effect. By using these materials, methods for developing a viral inhibitor and an antiviral therapeutic agent or preventing and treating a virus-related disease are provided.

What is claimed is:

1. A method of reducing human immunodeficiency virus (HIV), hepatitis B virus (HBV), or hepatitis C virus (HCV) replication, transcription, reactivation, or production in a subject, comprising administering a peptide having the amino acid sequence of SEQ ID NO:1 to the subject, wherein the replication, transcription, reactivation, or production of HIV, HBV, or HCV is mediated by heat shock protein 90.

2. The method of claim 1, wherein a concentration of the peptide in the composition is 0.0001 to 100 μM.

3. The method of claim 1, wherein the peptide is administered at a daily dose of 0.01 μg/kg/day to 10 g/kg/day.

4. The method of claim 1, wherein the peptide is contained in a conjugated form with a labeling material.

5. The method of claim 4, wherein the labeling material is a fluorescent material or a contrast material.

6. The method of claim 5, wherein the fluorescent material is FITC.

* * * * *